Figure 1A:
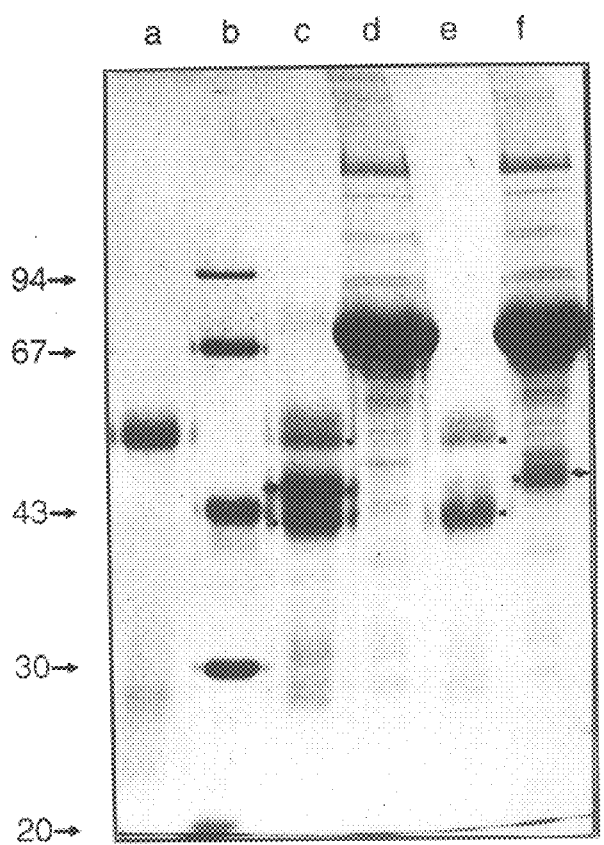

United States Patent [19]
Casterman et al.

[11] Patent Number: 6,015,695
[45] Date of Patent: Jan. 18, 2000

[54] IMMUNOGLOBULINS DEVOID OF LIGHT CHAINS

[75] Inventors: Cecile Casterman; Raymond Hamers, both of Sint-Genesius-Rode, Belgium

[73] Assignee: Vrije Universiteit Brussel, Brussels, Belgium

[21] Appl. No.: 08/468,739

[22] Filed: Jun. 6, 1995

Related U.S. Application Data

[62] Division of application No. 08/106,944, Aug. 17, 1993, abandoned.

[30]    Foreign Application Priority Data

Aug. 21, 1992  [EP]  European Pat. Off. .............. 92402326
May 21, 1993  [EP]  European Pat. Off. .............. 93401310

[51] Int. Cl.[7] .............................. C12N 7/01; C12N 15/63; C12P 21/08; C07H 21/04
[52] U.S. Cl. ..................... 435/69.6; 435/243; 435/320.1; 435/326; 435/348; 435/363; 530/387.3; 536/23.53
[58] Field of Search ..................... 530/387.3; 435/69.6, 435/243, 326, 348, 363, 320.1; 536/23.53

[56]    References Cited

FOREIGN PATENT DOCUMENTS

WO 92/01787  2/1992  WIPO .

OTHER PUBLICATIONS

Webster's II New Riverside University Dictionary, The Riverside Publishing Co./Houghton Mifflin Co., Boston, MA, 1995.

Hamers–Casterman et al., "Nature", 363:446–48 (1993).

Roitt et al., "Immunology", Gower Medical Publishing, London, pp. 1.5 and 5.7 (1985).

Ward et al., "Nature", 341:544–546 (1989).

Blier et al., "A Limited Number of B Cell Lineages Generates The Heterogeneity Of A Secondary Immune Response", *J. Immunology,* vol. 139, No. 12, pp. 3996–4006 (Dec. 15, 1987).

*Primary Examiner*—Frank C. Eisenschenk
*Assistant Examiner*—Evelyn Rabin
*Attorney, Agent, or Firm*—Finnegan, Henderson, Farabow, Garrett & Dunner, L.L.P.

[57]    ABSTRACT

There is provided an isolated immunoglobulin comprising two heavy polypeptide chains sufficient for the formation of a complete antigen binding site or several antigen binding sites, wherein the immunoglobulin is further devoid of light polypeptide chains.

13 Claims, 12 Drawing Sheets

Papaine cleavage sites

```
DR01006  C----------------------------------TCGAG---TCTGGGGGAGG
DR27006  C----------------------------------TCGAG---TCTGGGGGAGG
DR03006  C-------AGGTGA----------AACTGCTCGAG---TCTGGAGGAGG
DR11006  C----------------------------------TCGAG---TCTGGGGGAGG
DR24006  C-------AGGTGA----------AACTGCTCGAG---TCTGGGGGAGG
DR16006  C----------------------------------TCGAG---TCTGGAGGAGG
DR19006  C----------------------------------TCGAG---TCTGGAGGAGG
DR07006  C----------------------------------TCGAG---TCTGGGGGAGG
DR16006  C----------------------------------TCGAG---TCTGGGGGAGG
DR20006  C----------------------------------TCGAG---TCAGGGGGAGG
DR25006  C----------------------------------TCGAG---TCTGGGGGAGG
DR20006  C----------------------------------TCGAG---TCTGGAGGAGG
DR21006  C----------------------------------TCGAG---TCTGGGGGAGG
DR09006  C-------AGGTGA----------AACTGCTCGAG---TCTGGGGGAGG
DR17006  C----------------------------------TCGAG---TCTGGGGGAGG
DR13006  C----------------------------------TCGAG---TCAGGGGGAGG
DR02006  CTCGAGTCAGGTGTCCGGTCTGATGTGCAGCTGGTGGCGTCTGGGGGAGG

DR01006  ATCGGTGCAGGCTGGAGGGTCTCTGAGACTCTC--GTGCG-CAGCCTCTG
DR27006  CTCGGTGCAGGCTGGAGGGTCTCTGAGACTCTCCTGTGCATCTTCTTCTA
DR03006  CTCGGTGCAGACTGGAGGATCTCTGAGACTCTCCTGTGCAGT--C-TCTG
DR11006  GTCGGTGCAGGCTGGAGGGTCTCTGAGACTCTCCTGTAATGT--C-TCTG
DR24006  GTCGGTGCAGGCTGGAGGGTCTCTGAGACTCTCCTGTAATGT--C-TCTG
DR16006  CTCGGCGCAGGCTGGAGGATCTCTGAGACTCTCCTGTGCAGC--CCACGG
DR19006  CTCGGTTCAGGCTGGAGGGTCCCTTAGACTCTCCTGTGCAGC--C-TCTG
DR07006  CTCGGTGCAGGGTGGAGGGTCTCTGAGACTCTCCTGTGCAA---TCTCTG
DR16006  CTCGGTGCAGGCTGGAGGGTCTCTGAGACTCTCCTGTACAG---GCTCTG
DR20006  CTCGGTACAGGTTGGAGGGTCTCTGAGACTCTCCTGTGTAG---CCTCTA
DR25006  CTCGGTACAAACTGGAGGGTCTCTGAGACTCTCTTGCG----AAATCTCTG
DR20006  CTCGGTGCAGGCTGGAGGGTCTCTGAGACTCTCCTGTG---TAGCCTCTG
DR21006  CTCGGTGCAGGTTGGAGGGTCTCTGAAACTCTCCTGTAAAAT---CTCTG
DR09006  CTCGGTGCAGGCTGGGGGGTCTCTGACACTCTCTTGTG---TATACAC--
DR17006  CTCGGTCCAACCTGGAGGATCTCTGACACTCTCCTGTACAGTT---TCTG
DR13006  CTCGGTGGAGGCTGGAGGGTCTCTGAGACTCTCCTGTACAG---CCTCTG
DR02006  CTCGGTGCAGGCTGGAGGCTCTCTGAGACTCTCCTGTACAG---CCTCTG

DR01006  GA--TACAGTAATT---GTCCCCTCACTTG-GAGCTGGTATCGCCAGTTT
DR27006  AA--TATATGCCTT---GCACCTACGACAT-GACCTGGTACCGCCAGGCT
DR03006  GA--TTCTCCTTTA---GTACCAGTTGTAT-GGCCTGGTTCCGCCAGGCT
DR11006  GC--TCTCCCAGTA---GTACTTATTGCCT-GGGCTGGTTCCGCCAGGCT
DR24006  GC--TCTCCCAGTA---GTACTTATTGCCT-GGGCTGGTTCCGCCAGGCT
DR16006  GA--TTCCGC-TCA---ATGGTTACTACAT-CGCCTGGTTCCGTCAGGCT
DR19006  AC--TACACCATCA---CTGATTATTGCAT-GGCCTGGTTCCGCCAGGCT
DR07006  GA--TACACGTACG---GTAGCTTCTGTAT-GGGCTGGTTCCGCGAGGGT
DR16006  GA--TTCCCCTATA---GTACCTTCTGTCT-GGGGTGGTTCCGCCAGGCT
DR20006  CT--CACACCGACA---GTAGCACCTGTAT-AGGCTGGTTCCGCCAGGCT
DR25006  GA--TTGACTTTTG---ATGATTCTGACGT-GGGGTGGTACCGCCAGGCT
DR20006  GA--TTCAATTTCG---AAACTTCTCGTAT-GGCGTGGTACCGCCAGACT
DR21006  GAGGTACCCCAGATCGTGTTCCTAAATCTTTGGCCTGGTTCCGCCAGGCT
DR09006  ------CAACGATACTGGGACCA--------TGGGATGGTTTCGCCAGGCT
DR17006  --GGGCCACCTACA---GTGACTACAGTATTGGA-TGGATCCGCCAGGCT
DR13006  G----------ATACGTAT-CCT----CTATGGCCTGGTTCCGCCAGGTT
DR02006  GAGA----CAGTTTCAGTAGATT--TGCCATGTCTTGGTTCCGCCAGGCT
```

FIG. 7A

```
DR01006  CCAGGAACGGAGCGCGAGTTCGTCTCCAGTATGGATCCGGATGGAAATAC
DR27006  CCAGGCAAGGAGCGCGAATTTGTCTCAAGTATAAATATTGATGGTAAGAC
DR03006  TCAGGAAAGCAGCGTGAGGGGGTCGCAGCCATTAATAGTGGCGGTGGTAG
DR11006  CCAGGGAGGGAGCGTGAGGGGGTCACAGCGATTAA------CACTGATGG
DR24006  CCAGGAAGGAGCGTGAGGGGGTCACAGCGATTAA------CACTGATGG
DR16006  CCTGGGAAGGGCGTGAGGGGGTCGCAACAATTAATGGTGGTCG-------
DR19006  CCAGGGAAGGCGTGAATTGGTCGCAGCGATTCAAGTTGTCCGTAGTGA
DR07006  CAGGCAAGGAACGTGAGGGGATCGCAACTATTCTTAATGGTGGTACTAA
DR16006  CCAGGGAAGGAGCGTGAGGGGGTCGCGGGTATTAATAGTGCAGGAGGTAA
DR20006  CCAGGGAAGGAGCGCGAGGGGGTCGCAAGTATATATTTTGGTGATGGTGG
DR25006  CCAGGGCATGAGTGCAAATTGGTCTCAGGTATTCTGAGTGATGGTACT-C
DR20006  CCAGGAAATGTGTGTGAGTTGGTCTCAAGTATTTACAGTGATGG------
DR21006  CCAGAGAAGGAGCGCGAGGGGATCGCAGTTCTTTCGACTAAGGATGGTAA
DR09006  CCAGGGAAAGAGTGCGAAAGGGTCGCGCATATTACGCCTGATGGTATGA-
DR17006  CCAGGGAAGGACCGTGAAGTAGTCGCAGCCGCTAATACTGGTG-------
DR13006  CCAGGGCAGGAGCGCGAGGGGGTCGCGTTTGTTCAAACGG----------
DR02006  CCAGGGAAGGAGTGCGAATTGGTCTCAAGCATTCAAAGTAATGGAAGGAC

DR01006  CAAGTACA---------------CATACTCCGTGAAGGGCCGCTTCACC
DR27006  AACATACG---------------CAGACTCCGTGAAGGGCCGATTCACC
DR03006  GACATACTA-CAACACATATGTCGCCGAGTCCGTGAAGGGCCGATTCGCC
DR11006  CAGTATCAT-ATACGCA------GCCGACTCCGTGAAGGGCCGATTCACC
DR24006  CAGTGTCAT-ATACGCA------GCCGACTCCGTGAAGGGCCGATTCACC
DR16006  ------CGA-CGTCACATACTACGCCGACTCCGTGACGGGCCGATTTACC
DR19006  TACT--CGC-C-TCACAGACTACGCCGACTCCGTGAAGGACGATTCACC
DR07006  --------------CACATACTATGCCGACTCGGTGAAGGGCCGATTCACC
DR16006  --------------TACTTACTATGCCGACGCCGTGAAGGGCCGATTCACC
DR20006  --------------TACGAATTATCGCGACTCCGTGAAGGGCCGGGTTACC
DR25006  CATATACAAAGAGTGGAGACTATGCTGAGTCTGTGAGGGGCCGGGTTACC
DR20006  CA-AAACATACTACGTCGACC--GCA-------TGAAGGGCCGATTCACC
DR21006  GA-------------CATTCTATGCCGACTCCGTGAAGGGCCGATTCACC
DR09006  ----------------CCTTCATTGATGAACCGTGAAGGGCGATTCACG
DR17006  ------CGACTAGTAAATTCTACGTCGACTTTGTGAAGGGCCGATTCACC
DR13006  --CTGACAAT-AGTGCATTATATGGCGACTCCGTGAAGGGCCGATTCACC
DR02006  AACTGA------------------GGCCGATTCCGTGCAAGGCCGATTCACC

DR01006  ATGTCCCGAGGCAGCACCGAGTACACAGTATTTCTGCAAATGGACAATCT
DR27006  ATCTCCCAAGACAGCGCCAAGAACACGGTGTATCTGCAGATGAACAGCCT
DR03006  ATCTCCCAAGACAACGCCAAGACCACGGTATATCTTGATATGAACAACCT
DR11006  ATCTCCCAAGACACCGCCAAGGAAACGGTACATCTCCAGATGAACAACCT
DR24006  ATCTCCCAAGACACCGCCAAGAAAACGGTATATCTCCAGATGAACAACCT
DR16006  ATCTCCCGAGACAGCCCCAAGAATACGGTGTATCTGCAGATGAACAGCCT
DR19006  ATCTCCCAAGGCAACACCAAGAACACAGTGAATCTGCAAATGAACAGCCT
DR07006  ATCTCCCAAGACAGCACGTTGAAGACGATGTATCTGCTAATGAACAACCT
DR16006  ATCTCCCAAGGGAATGCCAAGAATACGGTGTTTCTGCAAATGGATAACTT
DR20006  ATCTCCCAACTCAACGCCCAGAACACAGTGTATCTGCAAATGAACAGCCT
DR25006  ATCTCCAGAGACAACGCCAAGAACATGATATACCTTCAAATGAACGACCT
DR20006  ATTTCTAGAGAGAATGCCAAGAATACATTGTATCTACAACTGAGCGGCCT
DR21006  ATCTTCTTAGATAATGACAAGACCACTTTCTCCTTACAACTTGATCGACT
DR09006  ATCTCCCGAGACAACGCCCAGAAAACGTTGTCTTTGCGAATGAATAGTCT
DR17006  ATTTCCCAAGACAACGCCAAGAATACGGTATATCTGCAAATGAGCTTCCT
DR13006  ATCTCCCACGACAACGCCAAGAACACGCTGTATCTGCAAATGCGCAACCT
DR02006  ATCTCCCGAGACAATTCCAGGAACACAGTGTATCTGCAAATGAACAGCCT
```

FIG. 7B

```
DR01006  GAAACCTGAGGACACGGCGATGTATTACTGTAAAAC-A---GCCCTAC--
DR27006  GAAACCTGAGGACACGGCGATGTATTACTGTAAAAT-A---GA--TTC--
DR03006  AACCCCTGAAGACACGGCTACGTATTACTGTGCGGCGG---TCCCAGCCC
DR11006  GCAACCTGAGGATACGGCCACCTATTACTGCGCGGCAA---GACTGACGG
DR24006  GCAACCTGAGGATACGGCCACCTATTACTGCGCGGCAA---GACTGACGG
DR16006  GAAACCTGAGGACACGGCCATCTACTTCTGTGCAGCAG---G-----CTC
DR19006  GACACCTGAGGACACGGCCATCTACAGTTGTGCGGCAA---C-----CAG
DR07006  GAAACCTGAAGACACGGGCACCTATTACTGTGCTG-CA---GAACTAAGT
DR16006  GAAACCTGAGGACACGGCCATCTATTACTGCGCGG-CG---GATAGTCCA
DR20006  GAAACCTGAGGACAGCGCCATGTACTACTGTGCAATCA---CTGAAATTG
DR25006  GAAACCTGAGGACACGGCCATGTATTACTGCGCGGTAGATGGTTGGACCC
DR20006  CAAACCTGAGGACACGGCCATGTATTACTGTGCG--------------CC
DR21006  GAACCCGGAGGACACTGCCGACTACTACTGCGCTGCAAATCAATTAGC--
DR09006  GAGGCCTGAGGACACGGCCGTGTATTACTGTGCGGCAGATTG--------
DR17006  GAAACCTGAGGACACGGCCATCTATTACTGTGCGGCAG-----CGGACCC
DR13006  GCAACCTGACGACACTGGCGTGTACTACTGTGCGGCC----------CAA
DR02006  GAAACCCGAGGACACGGCCGTGTATTACTGTGGGGCAGT-----------

DR01006  ------------------------A-AC--CTGGGGGTTATTGTGGGTA-
DR27006  ------------------------GTAC--CCGTGCCATCTCCTTGATG-
DR03006  ACTTGGGACCT-------------GGCG-CCATT------CTTGATTTG
DR11006  AGATGGGGGCTTGTGATGCGAGATGGGCGACCTTAGC--GACAAGGAC-G
DR24006  AGATGGGGGCTTGTGATGCGAGATGGGCGACCTTAGC--GACAAGGAC-G
DR16006  GCGTTTTT-CTAGTCCTGTTGGGAGCACTTC-TAGAC---TCGAAAGTAG
DR19006  TAGTTTTTACTGGTACT-------GCAC--------C---ACG------G
DR07006  GGTGGTAGTTGTGAATTGC---CTTTGC------TATTTGACTA------
DR16006  TGTTACATGCCGACTATGC---CCGCTCCCCCGATACGAGACAGTTTTGG
DR20006  AGTGGTATGGGTGCAATTT---AAGGACTACTTTTACT---C-------G
DR25006  GGAAGGAAG--GGGGAATCGGGTTAC----CCTGGTCGGTCCAATGTGAA
DR20006  GGTTGAA--------------TATC----CTATTGCAGAC--ATGTGTT
DR21006  ---TGGTGGCTGGTATT------TGGACCCGAATTACTGG-CTCTCTGTG
DR09006  ---GAAATACTGGA----CTTGTGGTGC--CCAGA-CTGG--------AG
DR17006  AAGTATATATTATAGTATC--------CTCCNNAT--------------
DR13006  AAGAAGGATCGTA-----CTAGATGGGC--------CGAGCCT-------
DR02006  ------------------------CTCCCTAA--TGGACCGAATTTC

DR01006  --TGGGTANTGCCTCTGGGGCCAGGGGACCCAGGTCACCGTCTCCTCACT
DR27006  --T------------CTGGGGCCAGGGGACCCAGGTCACCGTCTCCTCACT
DR03006  AAAAAGTATAAGTACTGGGGCCAGGGGACCCAGGTCACCGTCTCCTCACT
DR11006  TTTGCGTATAACTACTGGGGCCGGGGGACCCAGGTCACCGTCTCCTCACT
DR24006  TTTGCGTATAACTACTGGGGCCGGGGGACCCAGGTCACCGTCTCCTCACT
DR16006  CGA-CT-ATAACTATTGGGGCCAGGGGATCCAGGTCACCGTCACCTCACT
DR19006  CGC-CTTATAACGTCTGGGGTCAGGGGACCCAGGTCACCGTCTCCTCACT
DR07006  CTGGG-----------GCCAGGGCACCCAGGTCACCGTCTCCTCACT
DR16006  CTGGGATGATTTT-----GGCCAGGGGACCCAGGTCACCGTCTCCTCACT
DR20006  CTGGG-----------GCCAGGGGACCCAGGTCACCGTCTCCTCACT
DR25006  GATGGTTATAACTATTGGGGCCAGGGGACCCAGGTCACCGTCTCCTCAC-
DR20006  CGAGAT----ACG---GCGACCCGGGGACCCAGGTCACCGTCTCCTCAC-
DR21006  GGTGCATATGCCATCTGGGGCCAGGGGACCCAGGTCACCGTCTCCTCAC-
DR09006  GATACTTCGGACAG-TGGGGTCAGGGGGCCCAGGTCACCGTCTCCTCACT
DR17006  --TGAGTATAAGTACTGGGGCCAGGGGACCCAGGTCACCGTCTCCTCA--
DR13006  CGAGAATGGAACAACTGGGGCCAGGGGACCCAGGTCACCGTCTCCTCA--
DR02006  CCAACATGGG--TGCCGGGGCCAGGGAACCCAGGTCACCGTCTCCT----
```

FIG. 7C

```
DR01006    AG----TTACCCGTACGACGTTCCGGACTACGGTTCTTAATAGAATTC
DR27006    AG----TTACCCGTACGAGCTTCCGGACTACGGTTCTTAATAGAATTC
DR03006    AGCTAGTTACCCGTACGACGTTCCGGACTACGGTTCTTAATAGAATTC
DR11006    AG----TTACCCGTACGACGTTCCGGACTACGGTTCTTAATAGAATTC
DR24006    AGCTAGTTACCCGTACGACGTTCCGGACTACGGTTCTTAATAGAATTC
DR16006    ----AGTTACCCGTACGACGTTCCGGACTACGGTTCTTAATAGAATTC
DR19006    ----AGTTACCCGTACGACGTTCCGGACTACGGTTCTTAATAGAATTC
DR07006    ----AGTTACCCGTACGACGTTCCGGACTACGGTTCTTAATAGAATTC
DR16006    ----AGTTACCCGTACGACGTTCCGGACTACGGTTCTTAATAGAATTC
DR20006    ----AGTTACCCGTACGACGTTCCGGACTACGGTTCTTAATAGAATTC
DR25006    ---TAGTTACCCGTACGACGTTCCGGACTACGGTTCTTAATAGAATTC
DR20006    ---TAGTTACCCGTACGACGAACCGGACTACGGTTCTTAATAGAATTC
DR21006    ---TAGTTACCCGTACGACGTTCCGGACTACGGTTCTTAATAGAATTC
DR09006    AGCTAGTTACCCGTACGACGTTCCGGACTACGGTTCTTAATAGAATTC
DR17006    ------------------------------------------------
DR13006    ------------------------------------------------
DR02006    ---------------------------------------------TA
```

FIG. 7D

SEQUENCE LISTING (1) GENERAL INFORMATION:

(iii) NUMBER OF SEQUENCES: 130

(2) INFORMATION FOR SEQ ID NO:1:

(i) SEQUENCE CHARACTERISTICS:
       (A) LENGTH: 22 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Domain
       (B) LOCATION: 1..22
       (D) OTHER INFORMATION: /label= FRAMEWORK 1

(xi) SEQUENCE DESCRIPTION: SEQ ID NO:1:

Gly Gly Ser Val Gln Thr Gly Gly Ser Leu Arg Leu Ser Cys Glu Ile
   1               5                   10                  15

Ser Gly Leu Thr Phe Asp
               20

(2) INFORMATION FOR SEQ ID NO:2:

(i) SEQUENCE CHARACTERISTICS:
       (A) LENGTH: 22 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Domain
       (B) LOCATION: 1..22
       (D) OTHER INFORMATION: /label= FRAMEWORK 1

(xi) SEQUENCE DESCRIPTION: SEQ ID NO:2:

Gly Gly Ser Val Gln Thr Gly Gly Ser Leu Arg Leu Ser Cys Ala Val
   1               5                   10                  15

Ser Gly Phe Ser Phe Ser
               20

(2) INFORMATION FOR SEQ ID NO:3:

(i) SEQUENCE CHARACTERISTICS:
       (A) LENGTH: 22 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Domain
       (B) LOCATION: 1..22
       (D) OTHER INFORMATION: /label= FRAMEWORK 1

(xi) SEQUENCE DESCRIPTION: SEQ ID NO:3:

Gly Gly Ser Glu Gln Gly Gly Ser Leu Arg Leu Ser Cys Ala Ile
   1               5                   10                  15

Ser Gly Tyr Thr Tyr Gly
               20

(2) INFORMATION FOR SEQ ID NO:4:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..22
        (D) OTHER INFORMATION: /label= FRAMEWORK 1

(xi) SEQUENCE DESCRIPTION: SEQ ID NO:4:

Gly Gly Ser Val Gln Pro Gly Gly Ser Leu Thr Leu Ser Cys Thr Val
   1               5                   10                  15

Ser Gly Ala Thr Tyr Ser
               20

(2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..22
        (D) OTHER INFORMATION: /label= FRAMEWORK 1

(xi) SEQUENCE DESCRIPTION: SEQ ID NO:5:

Gly Gly Ser Val Gln Ala Gly Gly Ser Leu Arg Leu Ser Cys Thr Gly
   1               5                   10                  15

Ser Gly Phe Pro Tyr Ser
               20

(2) INFORMATION FOR SEQ ID NO:6:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..21
        (D) OTHER INFORMATION: /label= FRAMEWORK 1

(xi) SEQUENCE DESCRIPTION: SEQ ID NO:6:

Gly Gly Ser Val Gln Ala Gly Gly Ser Leu Arg Leu Ser Cys Val Ala
   1               5                   10                  15

Gly Phe Gly Thr Ser
               20

(2) INFORMATION FOR SEQ ID NO:7:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide

```
    (ix) FEATURE:
          (A) NAME/KEY: Domain
          (B) LOCATION: 1..21
          (D) OTHER INFORMATION: /label= FRAMEWORK 1

(xi) SEQUENCE DESCRIPTION: SEQ ID NO:7:

Gly Gly Ser Val Gln Ala Gly Gly Ser Leu Arg Leu Ser Cys Val Ser
    1               5                   10                  15

Phe Ser Pro Ser Ser
                20

(2) INFORMATION FOR SEQ ID NO:8:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Domain
          (B) LOCATION: 1..11
          (D) OTHER INFORMATION: /label= FRAMEWORK 4

(xi) SEQUENCE DESCRIPTION: SEQ ID NO:8:

Trp Gly Gln Gly Thr Gln Val Thr Val Ser Ser
    1               5                   10

(2) INFORMATION FOR SEQ ID NO:9:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Domain
          (B) LOCATION: 1..11
          (D) OTHER INFORMATION: /label= FRAMEWORK 4

(xi) SEQUENCE DESCRIPTION: SEQ ID NO:9:

Trp Gly Gln Gly Thr Leu Val Thr Val Ser Ser
    1               5                   10

(2) INFORMATION FOR SEQ ID NO:10:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Domain
          (B) LOCATION: 1..11
          (D) OTHER INFORMATION: /label= FRAMEWORK 4

(xi) SEQUENCE DESCRIPTION: SEQ ID NO:10:

Trp Gly Gln Gly Ala Gln Val Thr Val Ser Ser
    1               5                   10

(2) INFORMATION FOR SEQ ID NO:11:

(i) SEQUENCE CHARACTERISTICS:
          (A) LENGTH: 11 amino acids
          (B) TYPE: amino acid
```

```
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..11
        (D) OTHER INFORMATION: /label= FRAMEWORK 4

(xi) SEQUENCE DESCRIPTION: SEQ ID NO:11:

Trp Gly Gln Gly Thr Gln Val Thr Ala Ser Ser
     1               5                  10

(2) INFORMATION FOR SEQ ID NO:12:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..11
        (D) OTHER INFORMATION: /label= FRAMEWORK 4

(xi) SEQUENCE DESCRIPTION: SEQ ID NO:12:

Arg Gly Gln Gly Thr Gln Val Thr Val Ser Leu
     1               5                  10

(2) INFORMATION FOR SEQ ID NO:13:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..14
        (D) OTHER INFORMATION: /label= CDR3

(xi) SEQUENCE DESCRIPTION: SEQ ID NO:13:

Ala Leu Gln Pro Gly Gly Tyr Cys Gly Tyr Gly Xaa Cys Leu Trp Gly
     1               5                  10                  15

Gln Gly Thr Gln Val Thr Val Ser Ser
                 20                  25

(2) INFORMATION FOR SEQ ID NO:14:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..12
        (D) OTHER INFORMATION: /label= CDR3

(xi) SEQUENCE DESCRIPTION: SEQ ID NO:14:

Val Ser Leu Met Asp Arg Ile Ser Gln His Gly Cys Arg Gly Gln Gly
     1               5                  10                  15

Thr Gln Val Thr Val Ser Leu
                 20
```

(2) INFORMATION FOR SEQ ID NO:15:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..18
        (D) OTHER INFORMATION: /label= CDR3

(xi) SEQUENCE DESCRIPTION: SEQ ID NO:15:

Val Pro Ala His Leu Gly Pro Gly Ala Ile Leu Asp Leu Lys Lys Tyr
    1               5                   10                  15

Lys Tyr Trp Gly Gln Gly Thr Gln Val Thr Val Ser Ser
                    20                  25

(2) INFORMATION FOR SEQ ID NO:16:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..15
        (D) OTHER INFORMATION: /label= CDR3

(xi) SEQUENCE DESCRIPTION: SEQ ID NO:16:

Phe Cys Tyr Ser Thr Ala Gly Asp Gly Gly Ser Gly Glu Met Tyr Trp
    1               5                   10                  15

Gly Gln Gly Thr Gln Val Thr Val Ser Ser
                    20                  25

(2) INFORMATION FOR SEQ ID NO:17:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..15
        (D) OTHER INFORMATION: /label= CDR3

(xi) SEQUENCE DESCRIPTION: SEQ ID NO:17:

Glu Leu Ser Gly Gly Ser Cys Glu Leu Pro Leu Leu Phe Asp Tyr Trp
    1               5                   10                  15

Gly Gln Gly Thr Gln Val Thr Val Ser Ser
                    20                  25

(2) INFORMATION FOR SEQ ID NO:18:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide

```
    (ix) FEATURE:
         (A) NAME/KEY: Domain
         (B) LOCATION: 1..17
         (D) OTHER INFORMATION: /label= CDR3

(xi) SEQUENCE DESCRIPTION: SEQ ID NO:18:

Asp Trp Lys Tyr Trp Thr Cys Gly Ala Gln Thr Gly Gly Tyr Phe Gly
    1               5                   10                  15

Gln Trp Gly Gln Gly Ala Gln Val Thr Val Ser Ser
                20                  25

(2) INFORMATION FOR SEQ ID NO:19:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Domain
         (B) LOCATION: 1..24
         (D) OTHER INFORMATION: /label= CDR3

(xi) SEQUENCE DESCRIPTION: SEQ ID NO:19:

Arg Leu Thr Glu Met Gly Ala Cys Asp Ala Arg Trp Ala Thr Leu Ala
    1               5                   10                  15

Thr Arg Thr Phe Ala Tyr Asn Tyr Trp Gly Gln Gly Thr Gln Val Thr
                20                  25                  30

Val Ser Ser
            35

(2) INFORMATION FOR SEQ ID NO:20:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Domain
         (B) LOCATION: 1..16
         (D) OTHER INFORMATION: /label= CDR3

(xi) SEQUENCE DESCRIPTION: SEQ ID NO:20:

Gln Lys Lys Asp Arg Thr Arg Trp Ala Glu Pro Arg Glu Trp Asn Asn
    1               5                   10                  15

Trp Gly Gln Gly Thr Gln Val Thr Ala Ser Ser
                20                  25

(2) INFORMATION FOR SEQ ID NO:21:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Domain
         (B) LOCATION: 1..21
         (D) OTHER INFORMATION: /label= CDR3

(xi) SEQUENCE DESCRIPTION: SEQ ID NO:21:
```

```
   Gly Ser Arg Phe Ser Ser Pro Val Gly Ser Thr Ser Arg Leu Glu Ser
   1               5                   10                  15

Ser Asp Tyr Asn Tyr Trp Gly Gln Gly Thr Gln Val Thr Ala Ser Ser
                   20                  25                  30

(2) INFORMATION FOR SEQ ID NO:22:

(i) SEQUENCE CHARACTERISTICS:
       (A) LENGTH: 27 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Domain
       (B) LOCATION: 1..16
       (D) OTHER INFORMATION: /label= CDR3

(xi) SEQUENCE DESCRIPTION: SEQ ID NO:22:

Ala Asp Pro Ser Ile Tyr Tyr Ser Ile Leu Xaa Ile Glu Tyr Lys Tyr
   1               5                   10                  15

Trp Gly Gln Gly Thr Gln Val Thr Val Ser Ser
                   20                  25

(2) INFORMATION FOR SEQ ID NO:23:

(i) SEQUENCE CHARACTERISTICS:
       (A) LENGTH: 33 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Domain
       (B) LOCATION: 1..22
       (D) OTHER INFORMATION: /label= CDR3

(xi) SEQUENCE DESCRIPTION: SEQ ID NO:23:

Asp Ser Pro Cys Tyr Met Pro Thr Met Pro Ala Pro Pro Ile Arg Asp
   1               5                   10                  15

Ser Phe Gly Trp Asp Asp Phe Gly Gln Gly Thr Gln Val Thr Val Ser
                   20                  25                  30

Ser (2) INFORMATION FOR SEQ ID NO:24:

(i) SEQUENCE CHARACTERISTICS:
       (A) LENGTH: 26 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Domain
       (B) LOCATION: 1..15
       (D) OTHER INFORMATION: /label= CDR3

(xi) SEQUENCE DESCRIPTION: SEQ ID NO:24:

Thr Ser Ser Phe Tyr Trp Tyr Cys Thr Thr Ala Pro Tyr Asn Val Trp
   1               5                   10                  15

Gly Gln Gly Thr Gln Val Thr Val Ser Ser
                   20                  25

(2) INFORMATION FOR SEQ ID NO:25:
```

(i) SEQUENCE CHARACTERISTICS:
            (A) LENGTH: 27 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Domain
            (B) LOCATION: 1..16
            (D) OTHER INFORMATION: /label= CDR3

(xi) SEQUENCE DESCRIPTION: SEQ ID NO:25:

Thr Glu Ile Glu Trp Tyr Gly Cys Asn Leu Arg Thr Thr Phe Thr Arg
       1               5                  10                  15

Trp Gly Gln Gly Thr Gln Val Thr Val Ser Ser
                   20                  25

(2) INFORMATION FOR SEQ ID NO:26:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Domain
            (B) LOCATION: 1..22
            (D) OTHER INFORMATION: /label= CDR3

(xi) SEQUENCE DESCRIPTION: SEQ ID NO:26:

Asn Gln Leu Ala Gly Gly Trp Tyr Leu Asp Pro Asn Tyr Trp Leu Ser
       1               5                  10                  15

Val Gly Ala Tyr Ala Ile Trp Gly Gln Gly Thr His Val Thr Val Ser
                   20                  25                  30

Ser (2) INFORMATION FOR SEQ ID NO:27:

(i) SEQUENCE CHARACTERISTICS:
            (A) LENGTH: 35 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Domain
            (B) LOCATION: 1..24
            (D) OTHER INFORMATION: /label= CDR3

(xi) SEQUENCE DESCRIPTION: SEQ ID NO:27:

Arg Leu Thr Glu Met Gly Ala Cys Asp Ala Arg Trp Ala Thr Leu Ala
       1               5                  10                  15

Thr Arg Thr Phe Ala Tyr Asn Tyr Trp Gly Arg Gly Thr Gln Val Thr
                   20                  25                  30

Val Ser Ser
                   35

(2) INFORMATION FOR SEQ ID NO:28:

(i) SEQUENCE CHARACTERISTICS:
            (A) LENGTH: 35 amino acids
            (B) TYPE: amino acid
            (C) STRANDEDNESS: single
            (D) TOPOLOGY: linear (ii) MOLECULE TYPE: peptide (ix) FEATURE:
              (A) NAME/KEY: Domain
              (B) LOCATION: 1..24
              (D) OTHER INFORMATION: /label= CDR3

(xi) SEQUENCE DESCRIPTION: SEQ ID NO:28:

Asp Gly Trp Thr Arg Lys Glu Gly Gly Ile Gly Leu Pro Trp Ser Val
   1               5                  10                  15

Gln Cys Glu Asp Gly Tyr Asn Tyr Trp Gly Gln Gly Thr Gln Val Thr
                   20                  25                  30

Val Ser Ser
               35

(2) INFORMATION FOR SEQ ID NO:29:

(i) SEQUENCE CHARACTERISTICS:
              (A) LENGTH: 21 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Domain
              (B) LOCATION: 1..10
              (D) OTHER INFORMATION: /label= CDR3

(xi) SEQUENCE DESCRIPTION: SEQ ID NO:29:

Asp Ser Tyr Pro Cys His Leu Leu Asp Val Trp Gly Gln Gly Thr Gln
   1               5                  10                  15

Val Thr Val Ser Ser
                   20

(2) INFORMATION FOR SEQ ID NO:30:

(i) SEQUENCE CHARACTERISTICS:
              (A) LENGTH: 23 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Domain
              (B) LOCATION: 1..12
              (D) OTHER INFORMATION: /label= CDR3

(xi) SEQUENCE DESCRIPTION: SEQ ID NO:30:

Val Glu Tyr Pro Ile Ala Asp Met Cys Ser Arg Tyr Gly Asp Pro Gly
   1               5                  10                  15

Thr Gln Val Thr Val Ser Ser
                   20

(2) INFORMATION FOR SEQ ID NO:31:

(i) SEQUENCE CHARACTERISTICS:
              (A) LENGTH: 27 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Domain
              (B) LOCATION: 1..27
              (D) OTHER INFORMATION: /label= CH2

(xi) SEQUENCE DESCRIPTION: SEQ ID NO:31:

```
    Ala Pro Glu Leu Leu Gly Gly Pro Thr Val Phe Ile Phe Pro Pro Lys
    1               5                   10                  15

Pro Lys Asp Val Leu Ser Ile Thr Leu Thr Pro
                20                  25
```

(2) INFORMATION FOR SEQ ID NO:32:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..27
        (D) OTHER INFORMATION: /label= CH2

(xi) SEQUENCE DESCRIPTION: SEQ ID NO:32:

```
    Ala Pro Glu Leu Pro Gly Gly Pro Ser Val Phe Val Phe Pro Thr Lys
    1               5                   10                  15

Pro Lys Asp Val Leu Ser Ile Ser Gly Arg Pro
                20                  25
```

(2) INFORMATION FOR SEQ ID NO:33:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..27
        (D) OTHER INFORMATION: /label= CH2

(xi) SEQUENCE DESCRIPTION: SEQ ID NO:33:

```
    Ala Pro Glu Leu Pro Gly Gly Pro Ser Val Phe Val Phe Pro Pro Lys
    1               5                   10                  15

Pro Lys Asp Val Leu Ser Ile Ser Gly Arg Pro
                20                  25
```

(2) INFORMATION FOR SEQ ID NO:34:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..27
        (D) OTHER INFORMATION: /label= CH2

(xi) SEQUENCE DESCRIPTION: SEQ ID NO:34:

```
    Ala Pro Glu Leu Leu Gly Gly Pro Ser Val Phe Ile Phe Pro Pro Lys
    1               5                   10                  15

Pro Lys Asp Val Leu Ser Ile Ser Gly Arg Pro
                20                  25
```

(2) INFORMATION FOR SEQ ID NO:35:

(i) SEQUENCE CHARACTERISTICS:

(A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..12
        (D) OTHER INFORMATION: /label= CH3

(xi) SEQUENCE DESCRIPTION: SEQ ID NO:35:

Gly Gln Thr Arg Glu Pro Gln Val Tyr Thr Leu Ala
    1               5                  10

(2) INFORMATION FOR SEQ ID NO:36:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..18
        (D) OTHER INFORMATION: /label= CH3

(xi) SEQUENCE DESCRIPTION: SEQ ID NO:36:

Gly Gln Thr Arg Glu Pro Gln Val Tyr Thr Leu Ala Pro Xaa Arg Leu
    1               5                  10                  15

Glu Leu (2) INFORMATION FOR SEQ ID NO:37:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: 1..12
        (D) OTHER INFORMATION: /label= hinge (xi) SEQUENCE DESCRIPTION: SEQ ID NO:37:

Gly Thr Asn Glu Val Cys Lys Cys Pro Lys Cys Pro
    1               5                  10

(2) INFORMATION FOR SEQ ID NO:38:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: 1..35
        (D) OTHER INFORMATION: /label= hinge (xi) SEQUENCE DESCRIPTION: SEQ ID NO:38:

Glu Pro Lys Ile Pro Gln Pro Gln Pro Lys Pro Gln Pro Gln Pro Gln
    1               5                  10                  15

Pro Gln Pro Lys Pro Gln Pro Lys Pro Glu Pro Glu Cys Thr Cys Pro

```
            20                  25                  30

Lys Cys Pro
         35

(2) INFORMATION FOR SEQ ID NO:39:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..28
        (D) OTHER INFORMATION: /label= CH2

(xi) SEQUENCE DESCRIPTION: SEQ ID NO:39:

Ala Pro Glu Leu Leu Gly Gly Pro Ser Val Phe Val Phe Pro Pro Lys
    1               5                  10                  15

Pro Lys Asp Val Leu Ser Ile Ser Gly Xaa Pro Lys
                20                  25

(2) INFORMATION FOR SEQ ID NO:40:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..28
        (D) OTHER INFORMATION: /label= CH2

(xi) SEQUENCE DESCRIPTION: SEQ ID NO:40:

Ala Pro Glu Leu Pro Gly Gly Pro Ser Val Phe Val Phe Pro Thr Lys
    1               5                  10                  15

Pro Lys Asp Val Leu Ser Ile Ser Gly Arg Pro Lys
                20                  25

(2) INFORMATION FOR SEQ ID NO:41:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..28
        (D) OTHER INFORMATION: /label= CH2

(xi) SEQUENCE DESCRIPTION: SEQ ID NO:41:

Ala Pro Glu Leu Pro Gly Gly Pro Ser Val Phe Val Phe Pro Pro Lys
    1               5                  10                  15

Pro Lys Asp Val Leu Ser Ile Ser Gly Arg Pro Lys
                20                  25

(2) INFORMATION FOR SEQ ID NO:42:

(i) SEQUENCE CHARACTERISTICS:
        (A) LENGTH: 28 amino acids
        (B) TYPE: amino acid
```

```
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..28
        (D) OTHER INFORMATION: /label= CH2

(xi) SEQUENCE DESCRIPTION: SEQ ID NO:42:

Ala Pro Glu Leu Leu Gly Gly Pro Ser Val Phe Ile Phe Pro Pro Lys
   1               5                   10                  15

Pro Lys Asp Val Leu Ser Ile Ser Gly Arg Pro Lys
                   20                  25

(2) INFORMATION FOR SEQ ID NO:43:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

Val Thr Val Ser Ser Gly Thr Asn Glu Val Cys Lys Cys Pro Lys Cys
   1               5                   10                  15

Pro Ala Pro Glu Leu Pro Gly Gly Pro Ser Val Phe Val Phe Pro
                   20                  25                  30

(2) INFORMATION FOR SEQ ID NO:44:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: 1..54
        (D) OTHER INFORMATION: /label= hinge (xi) SEQUENCE DESCRIPTION: SEQ ID NO:44:

Val Thr Val Ser Ser Glu Pro Lys Ile Pro Gln Pro Gln Pro Lys Pro
   1               5                   10                  15

Gln Pro Gln Pro Gln Pro Gln Pro Lys Pro Gln Pro Lys Pro Glu Pro
                   20                  25                  30

Glu Cys Thr Cys Pro Lys Cys Pro Ala Pro Glu Leu Leu Gly Gly Pro
                   35                  40                  45

Ser Val Phe Ile Phe Pro
           50

(2) INFORMATION FOR SEQ ID NO:45:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: 1..14
        (D) OTHER INFORMATION: /label= hinge
```

(ix) FEATURE:
            (A) NAME/KEY: Domain
            (B) LOCATION: 1..14
            (D) OTHER INFORMATION: /label= CH2

(xi) SEQUENCE DESCRIPTION: SEQ ID NO:45:

Ala Pro Glu Leu Pro Gly Gly Pro Ser Val Phe Val Phe Pro
    1               5                   10

(2) INFORMATION FOR SEQ ID NO:46:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Domain
            (B) LOCATION: 1..14
            (D) OTHER INFORMATION: /label= CH2

(xi) SEQUENCE DESCRIPTION: SEQ ID NO:46:

Ala Pro Glu Leu Leu Gly Gly Pro Ser Val Phe Ile Phe Pro
    1               5                   10

(2) INFORMATION FOR SEQ ID NO:47:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other
            (A) DESCRIPTION: DNA (synthetic)

(xi) SEQUENCE DESCRIPTION: SEQ ID NO:47:

CGCCATCAAG GTAACAGTTG A                                              21

(2) INFORMATION FOR SEQ ID NO:48:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Other
            (A) DESCRIPTION: DNA (synthetic)

(ix) FEATURE:
            (A) NAME/KEY: misc_feature
            (B) LOCATION: 12..17
            (D) OTHER INFORMATION: /label= XhoI site
                                   /note= "RESTRICTION SITE"

(xi) SEQUENCE DESCRIPTION: SEQ ID NO:48:

AGGTCCAGCT GCTCGAGTCT GG                                             22

(2) INFORMATION FOR SEQ ID NO:49:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Other
            (A) DESCRIPTION: DNA (synthetic)

(ix) FEATURE:
            (A) NAME/KEY: misc_feature (B) LOCATION: 12..17
        (D) OTHER INFORMATION: /label= XhoI site
                                /note= "Restriction site"

(xi) SEQUENCE DESCRIPTION: SEQ ID NO:49:

AGCTCCAGCT GCTCGAGTCT GG                                                22

(2) INFORMATION FOR SEQ ID NO:50:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other
        (A) DESCRIPTION: DNA (synthetic)

(ix) FEATURE:
        (A) NAME/KEY: misc_feature
        (B) LOCATION: 12..17
        (D) OTHER INFORMATION: /label= XhoI site
                                /note= "restriction site"

(xi) SEQUENCE DESCRIPTION: SEQ ID NO:50:

AGGTCCAGCT TCTCGAGTCT GG                                                22

(2) INFORMATION FOR SEQ ID NO:51:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Other
        (A) DESCRIPTION: DNA (synthetic)

(xi) SEQUENCE DESCRIPTION: SEQ ID NO:51:

TCTTAACTAG TGAGGAGACG GTGACCTG                                          28

(2) INFORMATION FOR SEQ ID NO:52:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other
        (A) DESCRIPTION: DNA (synthetic)

(ix) FEATURE:
        (A) NAME/KEY: misc_feature
        (B) LOCATION: 1..5
        (D) OTHER INFORMATION: /label= SpeI (xi) SEQUENCE DESCRIPTION: SEQ ID NO:52:

CTAGTGCACC ACCATCACCA TCACTAATAG                                        30

(2) INFORMATION FOR SEQ ID NO:53:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other
        (A) DESCRIPTION: DNA (synthetic)

(ix) FEATURE:
        (A) NAME/KEY: misc_feature
        (B) LOCATION: 1..30
        (D) OTHER INFORMATION: /note= "Sequence complementary to

SEQ ID NO: 52"

(ix) FEATURE:
    (A) NAME/KEY: misc_feature
    (B) LOCATION: 26..30
    (D) OTHER INFORMATION: /label= EcoRI (xi) SEQUENCE DESCRIPTION: SEQ ID NO:53:

ACGTGGTGGT AGTGGTAGTG ATTATCTTAA                                30

(2) INFORMATION FOR SEQ ID NO:54:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (vi) ORIGINAL SOURCE:
        (A) ORGANISM: Camelus dromedarius (ix) FEATURE:
        (A) NAME/KEY: Domain
        (B) LOCATION: 1..25
        (D) OTHER INFORMATION: /label= CH2

(ix) FEATURE:
        (A) NAME/KEY: Domain
        (B) LOCATION: 26..43
        (D) OTHER INFORMATION: /label= CH3

(xi) SEQUENCE DESCRIPTION: SEQ ID NO:54:

Leu Pro Gly Gly Pro Ser Val Phe Val Phe Pro Pro Lys Pro Lys Asp
    1               5                   10                  15

Val Leu Ser Ile Xaa Gly Xaa Pro Lys Gly Gln Thr Arg Glu Pro Gln
                20                  25                  30

Val Tyr Thr Leu Ala Pro Xaa Arg Leu Glu Leu
                35                  40

(2) INFORMATION FOR SEQ ID NO:55:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (vi) ORIGINAL SOURCE:
        (A) ORGANISM: Camelus dromedarius (ix) FEATURE:
        (A) NAME/KEY: Domain
        (B) LOCATION: 1..24
        (D) OTHER INFORMATION: /label= CH2
                               /note= "Clone #72/1"

(xi) SEQUENCE DESCRIPTION: SEQ ID NO:55:

Leu Pro Gly Gly Pro Ser Val Phe Val Phe Pro Thr Lys Pro Lys Asp
    1               5                   10                  15

Val Leu Ser Ile Ser Gly Arg Pro
                20

(2) INFORMATION FOR SEQ ID NO:56:

(i) SEQUENCE CHARACTERISTICS:
        (A) LENGTH: 24 amino acids

```
        (B) TYPE: amino acid
        (C) STRANDEDNESS: single
        (D) TOPOLOGY: linear (ii) MOLECULE TYPE: peptide (v) FRAGMENT TYPE: N-terminal (vi) ORIGINAL SOURCE:
        (A) ORGANISM: Camelus dromedarius (ix) FEATURE:
        (A) NAME/KEY: Domain
        (B) LOCATION: 1..24
        (D) OTHER INFORMATION: /label= CH2

(xi) SEQUENCE DESCRIPTION: SEQ ID NO:56:

Leu Pro Gly Gly Pro Ser Val Phe Val Phe Pro Pro Lys Pro Lys Asp
    1               5                   10                  15

Val Leu Ser Ile Ser Gly Arg Pro
                20

(2) INFORMATION FOR SEQ ID NO:57:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (vi) ORIGINAL SOURCE:
        (A) ORGANISM: Camelus dromedarius (ix) FEATURE:
        (A) NAME/KEY: Domain
        (B) LOCATION: 1..24
        (D) OTHER INFORMATION: /label= CH2

(xi) SEQUENCE DESCRIPTION: SEQ ID NO:57:

Leu Leu Gly Gly Pro Ser Val Phe Ile Phe Pro Pro Lys Pro Lys Asp
    1               5                   10                  15

Val Leu Ser Ile Ser Gly Arg Pro
                20

(2) INFORMATION FOR SEQ ID NO:58:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (vi) ORIGINAL SOURCE:
        (A) ORGANISM: Camelus dromedarius (ix) FEATURE:
        (A) NAME/KEY: Domain
        (B) LOCATION: 1..30
        (D) OTHER INFORMATION: /label= Framework 1
                               /note= "CAMEL"

(xi) SEQUENCE DESCRIPTION: SEQ ID NO:58:

Asp Val Gln Leu Val Ala Ser Gly Gly Gly Ser Val Gly Ala Gly Gly
    1               5                   10                  15

Ser Leu Arg Leu Ser Cys Thr Ala Ser Gly Asp Ser Phe Ser
                20                  25                  30
```

(2) INFORMATION FOR SEQ ID NO:59:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Camelus dromedarius (ix) FEATURE:
        (A) NAME/KEY: Domain
        (B) LOCATION: 1..11
        (D) OTHER INFORMATION: /label= Framework 4

(xi) SEQUENCE DESCRIPTION: SEQ ID NO:59:

Trp Gly Arg Gly Thr Gln Val Thr Val Ser Ser
    1             5                  10

(2) INFORMATION FOR SEQ ID NO:60:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Camelus dromedarius (ix) FEATURE:
        (A) NAME/KEY: Domain
        (B) LOCATION: 1..11
        (D) OTHER INFORMATION: /label= Framework 4

(xi) SEQUENCE DESCRIPTION: SEQ ID NO:60:

Trp Gly Gln Gly Thr His Val Thr Val Ser Ser
    1             5                  10

(2) INFORMATION FOR SEQ ID NO:61:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Domain
        (B) LOCATION: 1..11
        (D) OTHER INFORMATION: /label= Framework 4

(xi) SEQUENCE DESCRIPTION: SEQ ID NO:61:

Trp Gly Gln Gly Ile Gln Val Thr Ala Ser Ser
    1             5                  10

(2) INFORMATION FOR SEQ ID NO:62:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Region
        (B) LOCATION: 1..14

(D) OTHER INFORMATION: /label= VH (ix) FEATURE:
         (A) NAME/KEY: Domain
         (B) LOCATION: 1..14
         (D) OTHER INFORMATION: /label= CDR3

(xi) SEQUENCE DESCRIPTION: SEQ ID NO:62:

Ala Leu Gln Pro Gly Gly Tyr Cys Gly Tyr Gly Xaa Cys Leu
    1               5                   10

(2) INFORMATION FOR SEQ ID NO:63:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (vi) ORIGINAL SOURCE:
         (A) ORGANISM: Camelus dromedarius (ix) FEATURE:
         (A) NAME/KEY: Region
         (B) LOCATION: 1..12
         (D) OTHER INFORMATION: /label= VH (ix) FEATURE:
         (A) NAME/KEY: Domain
         (B) LOCATION: 1..12
         (D) OTHER INFORMATION: /label= CDR3

(xi) SEQUENCE DESCRIPTION: SEQ ID NO:63:

Val Ser Leu Met Asp Arg Ile Ser Gln His Gly Cys
    1               5                   10

(2) INFORMATION FOR SEQ ID NO:64:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (vi) ORIGINAL SOURCE:
         (A) ORGANISM: Camelus dromedarius (ix) FEATURE:
         (A) NAME/KEY: Region
         (B) LOCATION: 1..18
         (D) OTHER INFORMATION: /label= VH (ix) FEATURE:
         (A) NAME/KEY: Domain
         (B) LOCATION: 1..18
         (D) OTHER INFORMATION: /label= CDR3

(xi) SEQUENCE DESCRIPTION: SEQ ID NO:64:

Val Pro Ala His Leu Gly Pro Gly Ala Ile Leu Asp Leu Lys Lys Tyr
    1               5                   10                  15

Lys Tyr (2) INFORMATION FOR SEQ ID NO:65:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (vi) ORIGINAL SOURCE:
    (A) ORGANISM: Camelus bactrianus (ix) FEATURE:
    (A) NAME/KEY: Region
    (B) LOCATION: 1..15
    (D) OTHER INFORMATION: /label= VH (ix) FEATURE:
    (A) NAME/KEY: Domain
    (B) LOCATION: 1..15
    (D) OTHER INFORMATION: /label= CDR3

(xi) SEQUENCE DESCRIPTION: SEQ ID NO:65:

```
Phe Cys Tyr Ser Thr Ala Gly Asp Gly Gly Ser Gly Glu Met Tyr
1               5                   10                  15
```

(2) INFORMATION FOR SEQ ID NO:66:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Camelus dromedarius (ix) FEATURE:
        (A) NAME/KEY: Region
        (B) LOCATION: 1..15
        (D) OTHER INFORMATION: /label= VH (ix) FEATURE:
        (A) NAME/KEY: Domain
        (B) LOCATION: 1..15
        (D) OTHER INFORMATION: /label= CDR3

(xi) SEQUENCE DESCRIPTION: SEQ ID NO:66:

```
Glu Leu Ser Gly Gly Ser Cys Glu Leu Pro Leu Leu Phe Asp Tyr
1               5                   10                  15
```

(2) INFORMATION FOR SEQ ID NO:67:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Region
        (B) LOCATION: 1..17
        (D) OTHER INFORMATION: /label= VH (ix) FEATURE:
        (A) NAME/KEY: Domain
        (B) LOCATION: 1..17
        (D) OTHER INFORMATION: /label= CDR3

(xi) SEQUENCE DESCRIPTION: SEQ ID NO:67:

```
Asp Trp Lys Tyr Trp Thr Cys Gly Ala Gln Thr Gly Gly Tyr Phe Gly
1               5                   10                  15

Gln
```

(2) INFORMATION FOR SEQ ID NO:68:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (ix) FEATURE:
             (A) NAME/KEY: Region
             (B) LOCATION: 1..24
             (D) OTHER INFORMATION: /label= VH (ix) FEATURE:
             (A) NAME/KEY: Domain
             (B) LOCATION: 1..24
             (D) OTHER INFORMATION: /label= CDR3

(xi) SEQUENCE DESCRIPTION: SEQ ID NO:68:

Arg Leu Thr Glu Met Gly Ala Cys Asp Ala Arg Trp Ala Thr Leu Ala
        1               5                   10                  15

Thr Arg Thr Phe Ala Tyr Asn Tyr
                    20

(2) INFORMATION FOR SEQ ID NO:69:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: protein (ix) FEATURE:
             (A) NAME/KEY: Region
             (B) LOCATION: 1..16
             (D) OTHER INFORMATION: /label= VH (ix) FEATURE:
             (A) NAME/KEY: Domain
             (B) LOCATION: 1..16
             (D) OTHER INFORMATION: /label= CDR3

(xi) SEQUENCE DESCRIPTION: SEQ ID NO:69:

Gln Lys Lys Asp Arg Thr Arg Trp Ala Glu Pro Arg Glu Trp Asn Asn
        1               5                   10                  15

(2) INFORMATION FOR SEQ ID NO:70:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: protein (ix) FEATURE:
             (A) NAME/KEY: Region
             (B) LOCATION: 1..21
             (D) OTHER INFORMATION: /label= VH (ix) FEATURE:
             (A) NAME/KEY: Domain
             (B) LOCATION: 1..21
             (D) OTHER INFORMATION: /label= CDR3

(xi) SEQUENCE DESCRIPTION: SEQ ID NO:70:

Gly Ser Arg Phe Ser Ser Pro Val Gly Ser Thr Ser Arg Leu Glu Ser
        1               5                   10                  15

Ser Asp Tyr Asn Tyr
                    20

(2) INFORMATION FOR SEQ ID NO:71:

(i) SEQUENCE CHARACTERISTICS:
            (A) LENGTH: 16 amino acids
            (B) TYPE: amino acid
            (C) STRANDEDNESS: single (D) TOPOLOGY: linear (ii) MOLECULE TYPE: protein (ix) FEATURE:
          (A) NAME/KEY: Region
          (B) LOCATION: 1..16
          (D) OTHER INFORMATION: /label= VH (ix) FEATURE:
          (A) NAME/KEY: Domain
          (B) LOCATION: 1..16
          (D) OTHER INFORMATION: /label= CDR3

(xi) SEQUENCE DESCRIPTION: SEQ ID NO:71:

Ala Asp Pro Ser Ile Tyr Tyr Ser Ile Leu Xaa Ile Glu Tyr Lys Tyr
     1               5                   10                  15

(2) INFORMATION FOR SEQ ID NO:72:

(i) SEQUENCE CHARACTERISTICS:
          (A) LENGTH: 22 amino acids
          (B) TYPE: amino acid
          (C) STRANDEDNESS: single
          (D) TOPOLOGY: linear (ii) MOLECULE TYPE: protein (ix) FEATURE:
          (A) NAME/KEY: Region
          (B) LOCATION: 1..22
          (D) OTHER INFORMATION: /label= VH (ix) FEATURE:
          (A) NAME/KEY: Domain
          (B) LOCATION: 1..22
          (D) OTHER INFORMATION: /label= CDR3

(xi) SEQUENCE DESCRIPTION: SEQ ID NO:72:

Asp Ser Pro Cys Tyr Met Pro Thr Met Pro Ala Pro Pro Ile Arg Asp
     1               5                   10                  15

Ser Phe Gly Trp Asp Asp
                 20

(2) INFORMATION FOR SEQ ID NO:73:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: protein (ix) FEATURE:
          (A) NAME/KEY: Region
          (B) LOCATION: 1..15
          (D) OTHER INFORMATION: /label= VH (ix) FEATURE:
          (A) NAME/KEY: Domain
          (B) LOCATION: 1..15
          (D) OTHER INFORMATION: /label= CDR3

(xi) SEQUENCE DESCRIPTION: SEQ ID NO:73:

Thr Ser Ser Phe Tyr Trp Tyr Cys Thr Thr Ala Pro Tyr Asn Val
     1               5                   10                  15

(2) INFORMATION FOR SEQ ID NO:74:

(i) SEQUENCE CHARACTERISTICS:
          (A) LENGTH: 16 amino acids
          (B) TYPE: amino acid
          (C) STRANDEDNESS: single
          (D) TOPOLOGY: linear (ii) MOLECULE TYPE: protein (ix) FEATURE:
              (A) NAME/KEY: Region
              (B) LOCATION: 1..16
              (D) OTHER INFORMATION: /label= VH (ix) FEATURE:
              (A) NAME/KEY: Domain
              (B) LOCATION: 1..16
              (D) OTHER INFORMATION: /label= CDR3

(xi) SEQUENCE DESCRIPTION: SEQ ID NO:74:

Thr Glu Ile Glu Trp Tyr Gly Cys Asn Leu Arg Thr Thr Phe Thr Arg
        1               5                   10                  15

(2) INFORMATION FOR SEQ ID NO:75:

(i) SEQUENCE CHARACTERISTICS:
              (A) LENGTH: 22 amino acids
              (B) TYPE: amino acid
              (C) STRANDEDNESS: single
              (D) TOPOLOGY: linear (ii) MOLECULE TYPE: protein (ix) FEATURE:
              (A) NAME/KEY: Region
              (B) LOCATION: 1..22
              (D) OTHER INFORMATION: /label= VH (ix) FEATURE:
              (A) NAME/KEY: Domain
              (B) LOCATION: 1..22
              (D) OTHER INFORMATION: /label= CDR3

(xi) SEQUENCE DESCRIPTION: SEQ ID NO:75:

Asn Gln Leu Ala Gly Gly Trp Tyr Leu Asp Pro Asn Tyr Trp Leu Ser
        1               5                   10                  15

Val Gly Ala Tyr Ala Ile
                    20

(2) INFORMATION FOR SEQ ID NO:76:

(i) SEQUENCE CHARACTERISTICS:
              (A) LENGTH: 24 amino acids
              (B) TYPE: amino acid
              (C) STRANDEDNESS: single
              (D) TOPOLOGY: linear (ii) MOLECULE TYPE: protein (ix) FEATURE:
              (A) NAME/KEY: Region
              (B) LOCATION: 1..24
              (D) OTHER INFORMATION: /label= VH (ix) FEATURE:
              (A) NAME/KEY: Domain
              (B) LOCATION: 1..24
              (D) OTHER INFORMATION: /label= CDR3

(xi) SEQUENCE DESCRIPTION: SEQ ID NO:76:

Arg Leu Thr Glu Met Gly Ala Cys Asp Ala Arg Trp Ala Thr Leu Ala
        1               5                   10                  15

Thr Arg Thr Phe Ala Tyr Asn Tyr
                    20

(2) INFORMATION FOR SEQ ID NO:77:

(i) SEQUENCE CHARACTERISTICS:
              (A) LENGTH: 24 amino acids
              (B) TYPE: amino acid
              (C) STRANDEDNESS: single
              (D) TOPOLOGY: linear (ii) MOLECULE TYPE: protein (ix) FEATURE:
    (A) NAME/KEY: Region
    (B) LOCATION: 1..24
    (D) OTHER INFORMATION: /label= VH (ix) FEATURE:
    (A) NAME/KEY: Domain
    (B) LOCATION: 1..24
    (D) OTHER INFORMATION: /label= CDR3

(xi) SEQUENCE DESCRIPTION: SEQ ID NO:77:

Asp Gly Trp Thr Arg Lys Glu Gly Gly Ile Gly Leu Pro Trp Ser Val
1               5                   10                  15

Gln Cys Glu Asp Gly Tyr Asn Tyr
            20

(2) INFORMATION FOR SEQ ID NO:78:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Region
        (B) LOCATION: 1..10
        (D) OTHER INFORMATION: /label= VH (ix) FEATURE:
        (A) NAME/KEY: Domain
        (B) LOCATION: 1..10
        (D) OTHER INFORMATION: /label= CDR3

(xi) SEQUENCE DESCRIPTION: SEQ ID NO:78:

Asp Ser Tyr Pro Cys His Leu Leu Asp Val
1               5                   10

(2) INFORMATION FOR SEQ ID NO:79:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Region
        (B) LOCATION: 1..12
        (D) OTHER INFORMATION: /label= VH (ix) FEATURE:
        (A) NAME/KEY: Domain
        (B) LOCATION: 1..12
        (D) OTHER INFORMATION: /label= CDR3

(xi) SEQUENCE DESCRIPTION: SEQ ID NO:79:

Val Glu Tyr Pro Ile Ala Asp Met Cys Ser Arg Tyr
1               5                   10

(2) INFORMATION FOR SEQ ID NO:80:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (vi) ORIGINAL SOURCE:
         (A) ORGANISM: Camelus dromedarius (xi) SEQUENCE DESCRIPTION: SEQ ID NO:80:

Glu Val Gln Leu Val Glu Ser Gly Gly Leu Val Gln Pro Gly Gly
    1               5                  10                  15

Ser Leu Arg Leu Ser Cys Ala Ala Ser Gly
                20                  25

(2) INFORMATION FOR SEQ ID NO:81:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: protein (vi) ORIGINAL SOURCE:
         (A) ORGANISM: Camelus dromedarius (xi) SEQUENCE DESCRIPTION: SEQ ID NO:81:

Trp Val Arg Gln Ala Pro Gly Lys Gly Leu Glu Trp Val Ser
    1               5                  10

(2) INFORMATION FOR SEQ ID NO:82:

(i) SEQUENCE CHARACTERISTICS:
         (A) LENGTH: 32 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:82:

Arg Phe Thr Ile Ser Arg Asp Asn Ser Lys Asn Thr Leu Tyr Leu Gln
    1               5                  10                  15

Met Asn Ser Leu Arg Ala Glu Asp Thr Ala Val Tyr Tyr Cys Ala Arg
                20                  25                  30

(2) INFORMATION FOR SEQ ID NO:83:

(i) SEQUENCE CHARACTERISTICS:
         (A) LENGTH: 37 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:83:

Trp Gly Gln Gly Thr Leu Val Thr Val Ser Ser Gly Thr Asn Glu Val
    1               5                  10                  15

Cys Lys Cys Pro Lys Cys Pro Ala Pro Glu Leu Pro Gly Gly Pro Ser
                20                  25                  30

Val Phe Val Phe Pro
                35

(2) INFORMATION FOR SEQ ID NO:84:

(i) SEQUENCE CHARACTERISTICS:
         (A) LENGTH: 18 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:84:

Gly Gly Ser Val Gln Gly Gly Gly Ser Leu Arg Leu Ser Cys Ala Ile
1               5                   10                  15

Ser Gly (2) INFORMATION FOR SEQ ID NO:85:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:85:

Trp Phe Arg Glu Gly Pro Gly Lys Glu Arg Glu Gly Ile Ala
1               5                   10

(2) INFORMATION FOR SEQ ID NO:86:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:86:

Arg Phe Thr Ile Ser Gln Asp Ser Thr Leu Lys Thr Met Tyr Leu Leu
1               5                   10                  15

Met Asn Asn Leu Lys Pro Glu Asp Thr Gly Thr Tyr Tyr Cys Ala Ala
                20                  25                  30

(2) INFORMATION FOR SEQ ID NO:87:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:87:

Trp Gly Gln Gly Thr Gln Val Thr Val Ser Ser Glu Pro Lys Ile Pro
1               5                   10                  15

Gln Pro Gln Pro Lys Pro Gln Pro Gln Pro Gln Pro Gln Pro Lys Pro
                20                  25                  30

Gln Pro Lys Pro Glu Pro Glu Cys Thr Cys Pro Lys Cys Pro Ala Pro
            35                  40                  45

Glu Leu Leu Gly Gly Pro Ser Val Phe Ile Phe Pro
        50                  55                  60

(2) INFORMATION FOR SEQ ID NO:88:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:88:

Gly Gly Ser Val Gln Ala Gly Gly Ser Leu Arg Leu Ser Cys Ala Ser
1               5                   10                  15

Ser Ser (2) INFORMATION FOR SEQ ID NO:89:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:89:

```
Trp Tyr Arg Gln Ala Pro Gly Lys Glu Arg Glu Phe Val Ser
 1               5                  10
```

(2) INFORMATION FOR SEQ ID NO:90:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:90:

```
Arg Phe Thr Ile Ser Gln Asp Ser Ala Lys Asn Thr Val Tyr Leu Gln
 1               5                  10                  15

Met Asn Ser Leu Lys Pro Glu Asp Thr Ala Met Tyr Tyr Cys Lys Ile
                20                  25                  30
```

(2) INFORMATION FOR SEQ ID NO:91:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:91:

```
Trp Gly Gln Gly Thr Gln Val Thr Val Ser Ser Gly Thr Asn Glu Val
 1               5                  10                  15

Cys Lys Cys Pro Lys Cys Pro Ala Pro Glu Leu Pro Gly Gly Pro Ser
                20                  25                  30

Val Phe Val Phe Pro
                35
```

(2) INFORMATION FOR SEQ ID NO:92:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:92:

```
CTCGAGTCTG GGGGAGGATC GGTGCAGGCT GGAGGGTCTC TGAGACTCTC GTGCGCAGCC      60

TCTGGATACA GTAATTGTCC CCTCACTTGG AGCTGGTATC GCCAGTTTCC AGGAACGGAG     120

CGCGAGTTCG TCTCCAGTAT GGATCCGGAT GGAAATACCA AGTACACATA CTCCGTGAAG     180

GGCCGCTTCA CCATGTCCCG AGGCAGCACC GAGTACACAG TATTTCTGCA AATGGACAAT     240

CTGAAACCTG AGGACACGGC GATGTATTAC TGTAAAACAG CCCTACAACC TGGGGGTTAT     300

TGTGGGTATG GGTANTGCCT CTGGGGCCAG GGGACCCAGG TCACCGTCTC CTCACTAGTT     360
```

ACCCGTACGA CGTTCCGGAC TACGGTTCTT AATAGAATTC                             400

(2) INFORMATION FOR SEQ ID NO:93:

(i) SEQUENCE CHARACTERISTICS:
        (A) LENGTH: 391 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:93:

CTCGAGTCTG GGGGAGGCTC GGTGCAGGCT GGAGGGTCTC TGAGACTCTC CTGTGCATCT          60

TCTTCTAAAT ATATGCCTTG CACCTACGAC ATGACCTGGT ACCGCCAGGC TCCAGGCAAG         120

GAGCGCGAAT TTGTCTCAAG TATAAATATT GATGGTAAGA CAACATACGC AGACTCCGTG         180

AAGGGCCGAT TCACCATCTC CCAAGACAGC GCCAAGAACA CGGTGTATCT GCAGATGAAC         240

AGCCTGAAAC CTGAGGACAC GGCGATGTAT TACTGTAAAA TAGATTCGTA CCCGTGCCAT         300

CTCCTTGATG TCTGGGGCCA GGGGACCCAG GTCACCGTCT CCTCACTAGT TACCCGTACG         360

AGCTTCCGGA CTACGGTTCT TAATAGAATT C                                       391

(2) INFORMATION FOR SEQ ID NO:94:

(i) SEQUENCE CHARACTERISTICS:
        (A) LENGTH: 443 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:94:

CAGGTGAAAC TGCTCGAGTC TGGAGGAGGC TCGGTGCAGA CTGGAGGATC TCTGAGACTC          60

TCCTGTGCAG TCTCTGGATT CTCCTTTAGT ACCAGTTGTA TGGCCTGGTT CCGCCAGGCT         120

TCAGGAAAGC AGCGTGAGGG GGTCGCAGCC ATTAATAGTG GCGGTGGTAG GACATACTAC         180

AACACATATG TCGCCGAGTC CGTGAAGGGC CGATTCGCCA TCTCCCAAGA CAACGCCAAG         240

ACCACGGTAT ATCTTGATAT GAACAACCTA ACCCCTGAAG ACACGGCTAC GTATTACTGT         300

GCGGCGGTCC CAGCCCACTT GGGACCTGGC GCCATTCTTG ATTTGAAAAA GTATAAGTAC         360

TGGGGCCAGG GGACCCAGGT CACCGTCTCC TCACTAGCTA GTTACCCGTA CGACGTTCCG         420

GACTACGGTT CTTAATAGAA TTC                                                443

(2) INFORMATION FOR SEQ ID NO:95:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:95:

CTCGAGTCTG GGGGAGGGTC GGTGCAGGCT GGAGGGTCTC TGAGACTCTC CTGTAATGTC          60

TCTGGCTCTC CCAGTAGTAC TTATTGCCTG GGCTGGTTCC GCCAGGCTCC AGGGAGGGAG         120

CGTGAGGGGG TCACAGCGAT TAACACTGAT GGCAGTATCA TATACGCAGC CGACTCCGTG         180

AAGGGCCGAT TCACCATCTC CCAAGACACC GCCAAGGAAA CGGTACATCT CCAGATGAAC         240

AACCTGCAAC CTGAGGATAC GGCCACCTAT TACTGCGCGG CAAGACTGAC GGAGATGGGG         300

GCTTGTGATG CGAGATGGGC GACCTTAGCG ACAAGGACGT TGCGTATAA CTACTGGGGC         360

CGGGGGACCC AGGTCACCGT CTCCTCACTA GTTACCCGTA CGACGTTCCG GACTACGGTT    420

CTTAATAGAA TTC    433

(2) INFORMATION FOR SEQ ID NO:96:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:96:

CAGGTGAAAC TGCTCGAGTC TGGGGGAGGG TCGGTGCAGG CTGGAGGGTC TCTGAGACTC    60

TCCTGTAATG TCTCTGGCTC TCCCAGTAGT ACTTATTGCC TGGGCTGGTT CCGCCAGGCT    120

CCAGGGAAGG AGCGTGAGGG GGTCACAGCG ATTAACACTG ATGGCAGTGT CATATACGCA    180

GCCGACTCCG TGAAGGGCCG ATTCACCATC TCCCAAGACA CCGCCAAGAA AACGGTATAT    240

CTCCAGATGA ACAACCTGCA ACCTGAGGAT ACGGCCACCT ATTACTGCGC GGCAAGACTG    300

ACGGAGATGG GGCTTGTGA TGCGAGATGG GCGACCTTAG CGACAAGGAC GTTTGCGTAT     360

AACTACTGGG GCCGGGGAC CCAGGTCACC GTCTCCTCAC TAGCTAGTTA CCCGTACGAC     420

GTTCCGGACT ACGGTTCTTA ATAGAATTC    449

(2) INFORMATION FOR SEQ ID NO:97:

(i) SEQUENCE CHARACTERISTICS:
        (A) LENGTH: 424 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:97:

CTCGAGTCTG GAGGAGGCTC GGCGCAGGCT GGAGGATCTC TGAGACTCTC CTGTGCAGCC    60

CACGGGATTC CGCTCAATGG TTACTACATC GCCTGGTTCC GTCAGGCTCC TGGGAAGGGG    120

CGTGAGGGGG TCGCAACAAT TAATGGTGGT CGCGACGTCA CATACTACGC CGACTCCGTG    180

ACGGGCCGAT TTACCATCTC CCGAGACAGC CCCAAGAATA CGGTGTATCT GCAGATGAAC    240

AGCCTGAAAC CTGAGGACAC GGCCATCTAC TTCTGTGCAG CAGGCTCGCG TTTTTCTAGT    300

CCTGTTGGGA GCACTTCTAG ACTCGAAAGT AGCGACTATA ACTATTGGGG CCAGGGGATC    360

CAGGTCACCG TCACCTCACT AGTTACCCGT ACGACGTTCC GGACTACGGT TCTTAATAGA    420

ATTC    424

(2) INFORMATION FOR SEQ ID NO:98:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:98:

CTCGAGTCTG GAGGAGGCTC GGTTCAGGCT GGAGGGTCCC TTAGACTCTC CTGTGCAGCC    60

TCTGACTACA CCATCACTGA TTATTGCATG GCCTGGTTCC GCCAGGCTCC AGGGAAGGAG    120

CGTGAATTGG TCGCAGCGAT TCAAGTTGTC CGTAGTGATA CTCGCCTCAC AGACTACGCC    180

GACTCCGTGA AGGGACGATT CACCATCTCC CAAGGCAACA CCAAGAACAC AGTGAATCTG    240

```
CAAATGAACA GCCTGACACC TGAGGACACG GCCATCTACA GTTGTGCGGC AACCAGTAGT    300

TTTTACTGGT ACTGCACCAC GGCGCCTTAT AACGTCTGGG GTCAGGGGAC CCAGGTCACC    360

GTCTCCTCAC TAGTTACCCG TACGACGTTC CGGACTACGG TTCTTAATAG AATTC         415
```

(2) INFORMATION FOR SEQ ID NO:99:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:99:

```
CTCGAGTCTG GGGGAGGCTC GGTGCAGGGT GGAGGGTCTC TGAGACTCTC CTGTGCAATC     60

TCTGGATACA CGTACGGTAG CTTCTGTATG GGCTGGTTCC GCGAGGGTCC AGGCAAGGAA    120

CGTGAGGGGA TCGCAACTAT TCTTAATGGT GGTACTAACA CATACTATGC CGACTCGGTG    180

AAGGGCCGAT TCACCATCTC CAAGACAGC ACGTTGAAGA CGATGTATCT GCTAATGAAC     240

AACCTGAAAC CTGAAGACAC GGGCACCTAT TACTGTGCTG CAGAACTAAG TGGTGGTAGT    300

TGTGAATTGC CTTTGCTATT TGACTACTGG GGCCAGGGCA CCCAGGTCAC CGTCTCCTCA    360

CTAGTTACCC GTACGACGTT CCGGACTACG GTTCTTAATA GAATTC                   406
```

(2) INFORMATION FOR SEQ ID NO:100:

(i) SEQUENCE CHARACTERISTICS:
        (A) LENGTH: 427 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:100:

```
CTCGAGTCTG GGGGAGGCTC GGTGCAGGCT GGAGGGTCTC TGAGACTCTC CTGTACAGGC     60

TCTGGATTCC CCTATAGTAC CTTCTGTCTG GGGTGGTTCC GCCAGGCTCC AGGGAAGGAG    120

CGTGAGGGGG TCGCGGGTAT TAATAGTGCA GGAGGTAATA CTTACTATGC CGACGCCGTG    180

AAGGGCCGAT TCACCATCTC CAAGGGAAT GCCAAGAATA CGGTGTTTCT GCAAATGGAT     240

AACTTGAAAC CTGAGGACAC GGCCATCTAT TACTGCGCGG CGGATAGTCC ATGTTACATG    300

CCGACTATGC CCGCTCCCCC GATACGAGAC AGTTTTGGCT GGGATGATTT TGGCCAGGGG    360

ACCCAGGTCA CCGTCTCCTC ACTAGTTACC CGTACGACGT TCCGGACTAC GGTTCTTAAT    420

AGAATTC                                                              427
```

(2) INFORMATION FOR SEQ ID NO:101:

(i) SEQUENCE CHARACTERISTICS:
        (A) LENGTH: 409 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:101:

```
CTCGAGTCAG GGGGAGGCTC GGTACAGGTT GGAGGGTCTC TGAGACTCTC CTGTGTAGCC     60

TCTACTCACA CCGACAGTAG CACCTGTATA GGCTGGTTCC GCCAGGCTCC AGGGAAGGAG    120

CGCGAGGGGG TCGCAAGTAT ATATTTTGGT GATGGTGGTA CGAATTATCG CGACTCCGTG    180

AAGGGCCGAT TCACCATCTC CCAACTCAAC GCCCAGAACA CAGTGTATCT GCAAATGAAC    240
```

```
AGCCTGAAAC CTGAGGACAG CGCCATGTAC TACTGTGCAA TCACTGAAAT TGAGTGGTAT        300

GGGTGCAATT TAAGGACTAC TTTTACTCGC TGGGGCCAGG GGACCCAGGT CACCGTCTCC        360

TCACTAGTTA CCCGTACGAC GTTCCGGACT ACGGTTCTTA ATAGAATTC                    409
```

(2) INFORMATION FOR SEQ ID NO:102:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:102:

```
CTCGAGTCTG GGGGAGGCTC GGTACAAACT GGAGGGTCTC TGAGACTCTC TTGCGAAATC         60

TCTGGATTGA CTTTTGATGA TTCTGACGTG GGGTGGTACC GCCAGGCTCC AGGGGATGAG        120

TGCAAATTGG TCTCAGGTAT TCTGAGTGAT GGTACTCCAT ATACAAAGAG TGGAGACTAT        180

GCTGAGTCTG TGAGGGGCCG GGTTACCATC TCCAGAGACA ACGCCAAGAA CATGATATAC        240

CTTCAAATGA ACGACCTGAA ACCTGAGGAC ACGGCCATGT ATTACTGCGC GGTAGATGGT        300

TGGACCCGGA AGGAAGGGGG AATCGGGTTA CCCTGGTCGG TCCAATGTGA AGATGGTTAT        360

AACTATTGGG GCCAGGGGAC CCAGGTCACC GTCTCCTCAC TAGTTACCCG TACGACGTTC        420

CGGACTACGG TTCTTAATAG AATTC                                             445
```

(2) INFORMATION FOR SEQ ID NO:103:

(i) SEQUENCE CHARACTERISTICS:
        (A) LENGTH: 394 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:103:

```
CTCGAGTCTG GAGGAGGCTC GGTGCAGGCT GGAGGGTCTC TGAGACTCTC CTGTGTAGCC         60

TCTGGATTCA ATTTCGAAAC TTCTCGTATG GCGTGGTACC GCCAGACTCC AGGAAATGTG        120

TGTGAGTTGG TCTCAAGTAT TTACAGTGAT GGCAAAACAT ACTACGTCGA CCGCATGAAG        180

GGCCGATTCA CCATTTCTAG AGAGAATGCC AAGAATACAT TGTATCTACA ACTGAGCGGC        240

CTCAAACCTG AGGACACGGC CATGTATTAC TGTGCGCCGG TTGAATATCC TATTGCAGAC        300

ATGTGTTCGA GATACGGCGA CCCGGGGACC CAGGTCACCG TCTCCTCACT AGTTACCCGT        360

ACGACGAACC GGACTACGGT TCTTAATAGA ATTC                                   394
```

(2) INFORMATION FOR SEQ ID NO:104:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:104:

```
CTCGAGTCTG GGGGAGGCTC GGTGCAGGTT GGAGGGTCTC TGAAACTCTC CTGTAAAATC         60

TCTGGAGGTA CCCCAGATCG TGTTCCTAAA TCTTTGGCCT GGTTCCGCCA GGCTCCAGAG        120

AAGGAGCGCG AGGGGATCGC AGTTCTTTCG ACTAAGGATG GTAAGACATT CTATGCCGAC        180

TCCGTGAAGG GCCGATTCAC CATCTTCTTA GATAATGACA AGACCACTTT CTCCTTACAA        240
```

```
CTTGATCGAC TGAACCCGGA GGACACTGCC GACTACTACT GCGCTGCAAA TCAATTAGCT      300

GGTGGCTGGT ATTTGGACCC GAATTACTGG CTCTCTGTGG GTGCATATGC CATCTGGGGC      360

CAGGGGACCC AGGTCACCGT CTCCTCACTA GTTACCCGTA CGACGTTCCG GACTACGGTT      420

CTTAATAGAA TTC                                                        433
```

(2) INFORMATION FOR SEQ ID NO:105:

(i) SEQUENCE CHARACTERISTICS:
        (A) LENGTH: 416 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:105:

```
CAGGTGAAAC TGCTCGAGTC TGGGGGAGGC TCGGTGCAGG CTGGGGGGTC TCTGACACTC       60

TCTTGTGTAT ACACCAACGA TACTGGGACC ATGGGATGGT TTCGCCAGGC TCCAGGGAAA      120

GAGTGCGAAA GGGTCGCGCA TATTACGCCT GATGGTATGA CCTTCATTGA TGAACCCGTG      180

AAGGGGCGAT TCACGATCTC CCGAGACAAC GCCCAGAAAA CGTTGTCTTT GCGAATGAAT      240

AGTCTGAGGC CTGAGGACAC GGCCGTGTAT TACTGTGCGG CAGATTGGAA ATACTGGACT      300

TGTGGTGCCC AGACTGGAGG ATACTTCGGA CAGTGGGGTC AGGGGGCCCA GGTCACCGTC      360

TCCTCACTAG CTAGTTACCC GTACGACGTT CCGGACTACG GTTCTTAATA GAATTC         416
```

(2) INFORMATION FOR SEQ ID NO:106:

(i) SEQUENCE CHARACTERISTICS:
        (A) LENGTH: 361 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:106:

```
CTCGAGTCTG GGGGAGGCTC GGTCCAACCT GGAGGATCTC TGACACTCTC CTGTACAGTT       60

TCTGGGGCCA CCTACAGTGA CTACAGTATT GGATGGATCC GCCAGGCTCC AGGGAAGGAC      120

CGTGAAGTAG TCGCAGCCGC TAATACTGGT GCGACTAGTA AATTCTACGT CGACTTTGTG      180

AAGGGCCGAT TCACCATTTC CAAGACAAC GCCAAGAATA CGGTATATCT GCAAATGAGC       240

TTCCTGAAAC CTGAGGACAC GGCCATCTAT TACTGTGCGG CAGCGGACCC AAGTATATAT      300

TATAGTATCC TCCATTGAGT ATAAGTACTG GGGCCAGGGG ACCCAGGTCA CCGTCTCCTC      360

A                                                                     361
```

(2) INFORMATION FOR SEQ ID NO:107:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:107:

```
CTCGAGTCAG GGGGAGGCTC GGTGGAGGCT GGAGGGTCTC TGAGACTCTC CTGTACAGCC       60

TCTGGATACG TATCCTCTAT GGCCTGGTTC CGCCAGGTTC CAGGGCAGGA GCGCGAGGGG      120

GTCGCGTTTG TTCAAACGGC TGACAATAGT GCATTATATG GCGACTCCGT GAAGGGCCGA      180

TTCACCATCT CCCACGACAA CGCCAAGAAC ACGCTGTATC TGCAAATGCG CAACCTGCAA      240
```

```
CCTGACGACA CTGGCGTGTA CTACTGTGCG GCCCAAAAGA AGGATCGTAC TAGATGGGCC      300

GAGCCTCGAG AATGGAACAA CTGGGGCCAG GGGACCCAGG TCACCGTCTC CTCA            354
```

(2) INFORMATION FOR SEQ ID NO:108:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:108:

```
CTCGAGTCAG GTGTCCGGTC TGATGTGCAG CTGGTGGCGT CTGGGGGAGG CTCGGTGCAG       60

GCTGGAGGCT CTCTGAGACT CTCCTGTACA GCCTCTGGAG ACAGTTTCAG TAGATTTGCC      120

ATGTCTTGGT TCCGCCAGGC TCCAGGGAAG GAGTGCGAAT TGGTCTCAAG CATTCAAAGT      180

AATGGAAGGA CAACTGAGGC CGATTCCGTG CAAGGCCGAT TCACCATCTC CCGAGACAAT      240

TCCAGGAACA CAGTGTATCT GCAAATGAAC AGCCTGAAAC CCGAGGACAC GGCCGTGTAT      300

TACTGTGGGG CAGTCTCCCT AATGGACCGA ATTTCCCAAC ATGGGTGCCG GGGCCAGGGA      360

ACCCAGGTCA CCGTCTCCTT A                                                 381
```

(2) INFORMATION FOR SEQ ID NO:109:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:109:

```
Gly Gln Pro Arg Glu Pro Gln Val Tyr Thr Leu Pro Pro Ser Arg Asp
 1               5                  10                  15

Glu Leu
```

(2) INFORMATION FOR SEQ ID NO:110:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:110:

```
Gly Gln Pro Arg Glu Pro Gln Val Tyr Thr Leu Pro Pro Ser Arg Glu
 1               5                  10                  15

Glu Met
```

(2) INFORMATION FOR SEQ ID NO:111:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:111:

```
Gly Gln Pro Arg Glu Pro Gln Val Tyr Thr Leu Pro Pro Ser Gln Glu
 1               5                  10                  15

Glu Met
```

(2) INFORMATION FOR SEQ ID NO:112:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:112:

Leu Leu Gly Gly Pro Ser Val Phe Leu Phe Pro Pro Lys Pro Lys Asp
    1               5                   10                  15

Thr Leu Met Ile Ser Arg Thr Pro
                20

(2) INFORMATION FOR SEQ ID NO:113:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:113:

Val Ala Gly Pro Ser Val Phe Leu Phe Pro Pro Lys Pro Lys Asp Thr
    1               5                   10                  15

Leu Met Ile Ser Arg Thr Pro
                20

(2) INFORMATION FOR SEQ ID NO:114:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:114:

Phe Leu Gly Gly Pro Ser Val Phe Leu Phe Pro Pro Lys Pro Lys Asp
    1               5                   10                  15

Thr Leu Met Ile Ser Arg Thr Pro
                20

(2) INFORMATION FOR SEQ ID NO:115:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:115:

Lys Gly Gln Pro Arg Glu Pro Gln Val Tyr Thr Leu Pro Pro Ser Arg
    1               5                   10                  15

Asp Glu Leu (2) INFORMATION FOR SEQ ID NO:116:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:116:

```
Lys Gly Gln Pro Arg Glu Pro Gln Val Tyr Thr Leu Pro Pro Ser Arg
1               5                   10                  15

Glu Glu Met
```

(2) INFORMATION FOR SEQ ID NO:117:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:117:

```
Lys Gly Gln Pro Arg Glu Pro Gln Val Tyr Thr Leu Pro Pro Ser Gln
1               5                   10                  15

Glu Glu Met
```

(2) INFORMATION FOR SEQ ID NO:118:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:118:

```
Glu Val Lys Leu Val Glu Ser Gly Gly Gly Leu Val Glu Pro Gly Gly
1               5                   10                  15

Ser Leu Arg Leu Ser Cys Ala Thr Ser Gly Phe Thr Phe Ser
            20                  25                  30
```

(2) INFORMATION FOR SEQ ID NO:119:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (xi) SEQUENCE DESCRIPTION: SEQ ID NO:119:

```
Glu Val Gln Leu Leu Ser Gly Gly Gly Leu Val Gln Pro Gly Gly Ser
1               5                   10                  15

Leu Arg Leu Ser Cys Ala Ala Ser Gly Phe Thr Phe Ser
            20                  25
```

(2) INFORMATION FOR SEQ ID NO:120:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:120:

```
Trp Gly Gln Gly Thr Thr Val Thr Val Ser Ser
1               5                   10
```

(2) INFORMATION FOR SEQ ID NO:121:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:121:

Trp Gly Gln Gly Thr Met Val Thr Val Ser Ser
1               5                   10

(2) INFORMATION FOR SEQ ID NO:122:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:122:

Trp Gly Gln Gly Thr Thr Leu Thr Val Ser Ser
1               5                   10

(2) INFORMATION FOR SEQ ID NO:123:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:123:

Trp Gly Gln Gly Thr Ser Val Thr Val Ser Ala
1               5                   10

(2) INFORMATION FOR SEQ ID NO:124:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:124:

Trp Gly Ala Gly Thr Thr Val Thr Val Ser Ser
1               5                   10

(2) INFORMATION FOR SEQ ID NO:125:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:125:

Asp Tyr Tyr Gly Ser Ser Tyr Phe Asp Val Trp Gly Ala Gly Thr Thr
1               5                   10                  15

Val Thr Val Ser Ser
            20

(2) INFORMATION FOR SEQ ID NO:126:

(i) SEQUENCE CHARACTERISTICS:
        (A) LENGTH: 67 amino acids
        (B) TYPE: amino acid
        (D) TOPOLOGY: linear (ii) MOLECULE TYPE: peptide (xi) SEQUENCE DESCRIPTION: SEQ ID NO:126:

Lys Val Asp Lys Arg Val Glu Leu Lys Thr Pro Leu Gly Asp Thr Thr
1               5                   10                  15

His Thr Cys Pro Arg Cys Pro Glu Pro Lys Cys Ser Asp Thr Pro Pro
              20                  25                  30

Pro Cys Pro Arg Cys Pro Glu Pro Lys Ser Cys Asp Thr Pro Pro Pro
              35                  40                  45

Cys Pro Arg Cys Pro Ala Pro Glu Leu Leu Gly Gly Pro Ser Val Phe
              50                  55                  60

Leu Phe Pro
65

(2) INFORMATION FOR SEQ ID NO:127:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:127:

Lys Val Asp Lys Lys Ala Glu Pro Lys Ser Cys Asp Lys Thr His Thr
1               5                   10                  15

Cys Pro Pro Cys Pro Ala Pro Glu Leu Leu Gly Gly Pro Ser Val Phe
              20                  25                  30

Leu Phe Pro
        35

(2) INFORMATION FOR SEQ ID NO:128:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:128:

Lys Val Lys Val Thr Val Glu Arg Lys Cys Cys Val Glu Cys Pro Pro
1               5                   10                  15

Cys Pro Ala Pro Pro Val Ala Gly Pro Ser Val Phe Leu Phe Pro
              20                  25                  30

(2) INFORMATION FOR SEQ ID NO:129:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:129:

Lys Val Asp Lys Arg Val Glu Ser Lys Tyr Gly Pro Pro Cys Pro Ser
1               5                   10                  15

Cys Pro Ala Pro Glu Phe Leu Gly Gly Pro Ser Val Phe Leu Phe Pro
              20                  25                  30

(2) INFORMATION FOR SEQ ID NO:130:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:130:

Trp Gly Arg Gly Thr Leu Val Thr Val Ser Ser
1               5                   10

IMMUNOGLOBULINS DEVOID OF LIGHT CHAINS

This is a division of application Ser. No. 08/106,944, filed Aug. 17, 1993, now abandoned.

The invention relates to new isolated immunoglobulins which are devoid of light polypeptide chains. These immunoglobulins do not consist in the degradation products of immunoglobulins composed of both heavy polypeptide and light polypeptide chains but to the contrary, the invention defines a new member of the family of the immunoglobulins, especially a new type of molecules capable of being involved in the immune recognition. Such immunoglobulins can be used for several purposes, especially for diagnosis or therapeutical purposes including protection against pathological agents or regulation of the expression or activity of proteins.

Up to now the structure proposed for immunoglobulins consists of a four-chain model referring to the presence of two identical light polypeptide chains (light chains) and two identical heavy polypeptide chains (heavy chains) linked together by disulfide bonds to form a y- or T-shaped macromolecules. These chains are composed of a constant region and a variable region, the constant region being subdivided in several domains. The two heavy polypeptide chains are usually linked by disulphide bounds in a so-called "hinge region" situated between the first and second domains of the constant region.

Among the proteins forming the class of the immunoglobulins, most of them are antibodies and accordingly present an antigen binding site or several antigen binding sites.

According to the four-chain model, the antigen binding site of an antibody is located in the variable domains of each of the heavy and light chains, and requires the association of the heavy and the light chains variable domains.

For the definition of these four-chain model immunoglobulins, reference is made to Roitt. I et al (Immunology-second-Edition Gower Medical Publishing USA, 1989). Reference is especially made to the part concerning the definition of the four-chain immunoglobulins, their polypeptidic and genetic structures, the definition of their variable and constant regions and the obtention of the fragments produced by enzymatic degradation according to well known techniques.

The inventors have surprisingly established that different molecules can be isolated from animals which naturally produce them, which molecules have functional properties of immunoglobulins these functions being in some cases related to structural elements which are distinct from those involved in the function of four-chain immunoglobulins due for instance to the absence of light chains.

The invention relates to two-chain model immunoglobulins which neither correspond to fragments obtained for instance by the degradation in particular the enzymatic degradation of a natural four-chain model immunoglobulin, nor correspond to the expression in host cells, of DNA coding for the constant or the variable region of a natural four-chain model immunoglobulin or a part of these regions, nor correspond to antibodies produced in lymphopaties for example in mice, rats or human.

E. S. Ward et al (1) have described some experiments performed on variable domains of heavy polypeptide chains ($V_H$) or/and light polypeptide chains ($V_K/F_V$) to test the ability of these variable domains, to bind specific antigens. For this purpose, a library of $V_H$ genes was prepared from the spleen genomic DNA of mice previously immunized with these specific antigens.

Ward et al have described in their publication that $V_H$ domains are relatively sticky, presumably due to the exposed hydrophobic surface normally capped by the $V_K$ or $V_\lambda$ domains. They consequently envisage that it should be possible to design $V_H$ domains having improved properties and further that $V_H$ domains with binding activities could serve as the building blocks for making variable fragments (Fv fragments) or complete antibodies.

The invention does not start from the idea that the different fragments (light and heavy chains) and the different domains of these fragments of four-chain model immunoglobulin can be modified to define new or improved antigen binding sites or a four-chain model immunoglobulin.

The inventors have determined that immunoglobulins can have a different structure than the known four-chain model and that such different immunoglobulins offer new means for the preparation of diagnosis reagents, therapeutical agents or any other reagent for use in research or industrial purposes.

Thus the invention provides new immunoglobulins which are capable of showing functional properties of four-chain model immunoglobulins although their structure appears to be more appropriate in many circumstances for their use, their preparation and in some cases for their modification. Moreover these molecules can be considered as lead structures for the modification of other immunoglobulins. The advantages which are provided by these immunoglobulins comprise the possibility to prepare them with an increased facility.

The invention accordingly relates to immunoglobulins characterized in that they comprise two heavy polypeptide chains sufficient for the formation of a complete antigen binding site or several antigen binding sites, these immunoglobulins being further devoid of light polypeptide chains. In a particular embodiment of the invention, these immunoglobulins are further characterized by the fact that they are the product of the expression in a prokaryotic or in a eukaryotic host cell, of a DNA or of a cDNA having the sequence of an immunoglobulin devoid of light chains as obtainable from lymphocytes or other cells of Camelids.

The immunoglobulins of the invention can be obtained for example from the sequences which are described in FIG. 7.

The immunoglobulins of the invention, which are devoid of light chains are such that the variable domains of their heavy chains have properties differing from those of the four-chain immunoglobulin $V_H$. The variable domain of a heavy-chain immunoglobulin of the invention has no normal interaction sites with the $V_L$ or with the $C_H1$ domain which do not exist in the heavy chain immunoglobulins. it is hence a novel fragment in many of its properties such as solubility and position of the binding site. For clarity reasons we will call it $V_{HH}$ in this text to distinguish it from the classical $V_H$ of four-chain immunoglobulins.

By "a complete antigen binding site" it is meant according to the invention, a site which will alone allow the recognition and complete binding of an antigen. This could be verified by any known method regarding the testing of the binding affinity.

These immunoglobulins which can be prepared by the technique of recombinant DNA, or isolated from animals, will be sometimes called "heavy-chain immunoglobulins" in the following pages. In a preferred embodiment of the invention, these immunoglobulins are in a pure form.

In a first embodiment, the immunoglobulins of the invention are obtainable in prokaryotic cells, especially in *E.coli* cells by a process comprising the steps of:

a) cloning in a Bluecript vector of a DNA or cDNA sequence coding for the $V_{HH}$ domain of an immunoglobulin devoid of light chain obtainable for instance from lymphocytes of Camelids, b) recovering the cloned fragment after amplification using a 5' primer containing an Xho site and a 3' primer containing the Spe site having the following sequence TC TTA ACT AGT GAG GAG ACG GTG ACC TG, SEQ ID NO:51, c) cloning the recovered fragment in phase in the immuno PBS vector after digestion of the vector with Xho and Spe restriction enzymes, d) transforming host cells, especially *E.coli* by transfection with the recombinant immuno PBS vector of step c, e) recovering the expression product of the $V_{HH}$ coding sequence, for instance by using antibodies raised against the dromadary $V_{HH}$ domain.

In another embodiment the immunoglobulins are heterospecific immunoglobulins obtainable by a process comprising the steps of:

obtaining a first DNA or cDNA sequence coding for a $V_{HH}$ domain or part thereof having a determined specificity against a given antigen and comprised between Xho and Spe sites, obtaining a second DNA or cDNA sequence coding for a $V_{HH}$ domain or part thereof, having a determined specificity different from the specificity of the first DNA or cDNA sequence and comprised between the Spe and EcoRI sites, digesting an immuno PBS vector with EcoRI and XhoI restriction enzymes, ligating the obtained DNA or cDNA sequences coding for $V_{HH}$ domains, so that the DNA or cDNA sequences are serially cloned in the vector, transforming a host cell, especially *E.coli* cell by transfection, and recovering the obtained immunoglobulins.

In another embodiment, the immunoglobulins are obtainable by a process comprising the steps of:

obtaining a DNA or cDNA sequence coding for a $V_{HH}$ domain or part thereof, having a determined specific antigen binding site, amplifying the obtained DNA or cDNA, using a 5' primer containing an initiation codon and a HindIII site, and a 3' primer containing a termination codon having a XhoI site, recombining the amplified DNA or cDNA into the HindIII (position 2650) and XhoI (position 4067) sites of a plasmid pMM984, transfecting permissive cells especially NB-E cells with the recombinant plasmid, recovering the obtained products.

Successful expression can be verified with antibodies directed against a region of a $V_{HH}$ domain, especially by an ELISA assay.

According to another particular embodiment of this process, the immunoglobulins are cloned in a parvovirus.

In another example these immunoglobulins are obtainable by a process comprising the further cloning of a second DNA or cDNA sequence having another determined antigen binding site, in the pMM984 plasmid.

Such an Immunoglobulin can be further characterized in that it is obtainable by a process wherein the vector is Yep 52 and the transformed recombinant cell is a yeast especially *S.cerevisiae*.

A particular Imunoglobulin is characterized in that it has a catalytic activity, especially in that it is directed against an antigen mimicking an activiated state of a given substrate. These catalytic antibodies can be modified at the level of their biding site, by random or directed mutagenesis in order to increase oe modify their catalytic function. Reference may be made to the publication of Lerner et al (TIBS November 1987. 427–430) for the general technique for the preparation of such catalytic immunoglobulins.

According to a preferred embodiment, the immunoglobulins of the invention are characterized in that their variable regions contain in position 45, an amino-acid which is different from leucine, proline or glutamine residue.

Moreover the heavy-chain immunoglobulins are not products characteristic of lymphocytes of animals nor from lymphocytes of a human patient suffering from lymphopathies. Such immunoglobulins produced in lymphopathies are monoclonal in origin and result from pathogenic mutations at the genomic level. They have apparently no antigen binding site.

The two heavy polypeptide chains of these immunoglobulins can be linked by a hinge region according to the definition of Roitt et al.

In a particular embodiment of the invention, immunoglobulins corresponding to the above-defined molecules are capable of acting as antibodies.

The antigen binding site(s) of the immunoglobulins of the invention are located in the variable region of the heavy chain.

In a particular group of these immunoglobulins each heavy polypeptide chain contains one antigen binding site on its variable region, and these sites correspond to the same amino-acid sequence.

In a further embodiment of the invention the immunoglobulins are characterized in that their heavy polypeptide chains contain a variable region ($V_{HH}$) and a constant region ($C_H$) according to the definition of Roitt et al, but are devoid of the first domain of their constant region. This first domain of the constant region is called $C_H1$.

These immunoglobulins having no $C_H1$ domain are such that the variable region of their chains is directly linked to the hinge region at the C-terminal part of the variable region.

The immunoglobulins of the type described hereabove can comprise type G immunoglobulins and especially immunoglobulins which are defined as immunoglobulins of class 2 (IgG2) or immunoglobulins of class 3 (IgG3).

The absence of the light chain and of the first constant domain lead to a modification of the nomenclature of the immunoglobulin fragments obtained by enzymatic digestion, according to Roitt et al.

The terms Fc and pFc on the one hand, Fc' and pFc' on the other hand corresponding respectively to the papain and pepsin digestion fragments are maintained.

The terms Fab F(ab)$_2$ F(ab')$_2$ Fabc, Fd and Fv are no longer applicable in their original sense as these fragments have either a light chain, the variable part of the light chain or the C$_H$1 domain.

The fragments obtained by papain digestion and composed of the V$_{HH}$ domain and the hinge region will be called FV$_{HH}$h or F(V$_{HH}$h)$_2$ depending upon whether or not they remain linked by the disulphide bonds.

In another embodiment of the invention, immunoglobulins replying to the hereabove given definitions can be originating from animals especially from animals of the camelid family. The inventors have found out that the heavy-chain immunoglobulins which are present in camelids are not associated with a pathological situation which would induce the production of abnormal antibodies with respect to the four-chain immunoglobulins. On the basis of a comparative study of old world camelids (*Camelus bactrianus* and *Camelus dromaderius*) and new world camelids (for example *Lama Paccos, Lama Glama,* and *Lama Vicugna*) the inventors have shown that the immunoglobulins of the invention, which are devoid of light polypeptide chains are found in all species. Nevertheless differences may be apparent in molecular weight of these immunoglobulins depending on the animals. Especially the molecular weight of a heavy chain contained in these immunoglobulins can be from approximately 43 kd to approximately 47 kd, in particular 45 kd.

Advantageously the heavy-chain immunoglobulins of the invention are secreted in blood of camelids.

Immunoglobulins according to this particular embodiment of the invention are obtainable by purification from serum of camelids and a process for the purification is described in details in the examples. In the case where the immunoglobulins are obtained from Camelids, the invention relates to immunoglobulins which are not in their natural biological environment.

According to the invention immunoglobulin IgG2 as obtainable by purification from the serum of camelids can be characterized in that:

it is not adsorbed by chromatography on Protein G Sepharose column, it is adsorbed by chromatography on Protein A Sepharose column, it has a molecular weight of around 100 kd after elution with a pH 4.5 buffer (0.15 M NaCl, 0.58% acetic acid adjusted to pH 4.5 by NaOH), it consists of heavy γ2 polypeptide chains or a molecular weight of around 46 kd preferably 45 after reduction.

According to a further embodiment of the invention another group of immunoglobulins corresponding to IgG3, as obtainable by purification from the serum of Camelids is characterized in that the immunoglobulin:

is adsorbed by chromatography on a Protein A Sepharose column, has a molecular weight of around 100 kd after elution with a pH 3.5 buffer (0.15 M NaCl, 0.58% acetic acid), is adsorbed by chromatography on a Protein G Sepharose column and eluted with pH 3.5 buffer (0.15 M NaCl, 0.58% acetic acid).

consists of heavy γ3 polypeptide chains of a molecular weight of around 45 Kd in particular between 43 and 47 kd after reduction.

The immunoglobulins of the invention which are devoid of light chains, nevertheless comprise on their heavy chains a constant region and a variable region. The constant region comprises different domains.

The variable region of immunoglobulins of the invention comprises frameworks (FW) and complementarity determining regions (CDR), especially 4 frameworks and 3 complementarity regions. It is distinguished from the four-chain immunoglobulins especially by the fact that this variable region can itself contain an antigen binding site or several, without contribution of the variable region of a light chain which is absent.

The amino-acid sequences of frameworks 1 and 4 comprise among others respectively amino-acid sequences which can be selected from the following:

for the framework 1 domain

```
G G S V Q T G G S L R L S C E I S G L T F D   SEQ ID NO:1
G G S V Q T G G S L R L S C A V S G F S F S   SEQ ID NO:2
G G S E Q G G G S L R L S C A I S G Y T Y G   SEQ ID NO:3
G G S V Q P G G S L T L S C T V S G A T Y S   SEQ ID NO:4
G G S V Q A G G S L R L S C T G S G F P Y S   SEQ ID NO:5
G G S V Q A G G S L R L S C V A G F G T S     SEQ ID NO:6
G G S V Q A G G S L R L S C V S F S P S S     SEQ ID NO:7
``` for the framework 4 domain

W G Q G T Q V T V S S  SEQ ID NO:8

W G Q G T L V T V S S  SEQ ID NO:9

W G Q G A Q V T V S S  SEQ ID NO:10

W G Q G T Q V T A S S  SEQ ID NO:11

R G Q G T Q V T V S L  SEQ ID NO:12 for the CDR3 domain

A L Q P G G Y C G Y G X - - - - - - - - - - C L  SEQ ID NO:62

V S L M D R I S Q H - - - - - - - - - - - - G C  SEQ ID NO:63

V P A H L G P G A I L D L K K Y - - - - - - K Y  SEQ ID NO:64

F C Y S T A G D G G S G E - - - - - - - - - M Y  SEQ ID NO:65

E L S G G S C E L P L L F - - - - - - - - - D Y  SEQ ID NO:66

D W K Y W T C G A Q T G G Y F - - - - - - - G Q  SEQ ID NO:67

R L T E M G A C D A R W A T L A T R T F A Y N Y  SEQ ID NO:68

Q K K D R T R W A E P R E W - - - - - - - - N N  SEQ ID NO:69

G S R F S S P V G S T S R L E S - S D Y - - N Y  SEQ ID NO:70

A D P S I Y Y S I L X I E Y - - - - - - - - K Y  SEQ ID NO:71

D S P C Y M P T M P A P P I R D S F G W - - D D  SEQ ID NO:72

T S S F Y W Y C T T A P Y - - - - - - - - - N V  SEQ ID NO:73

T E I E W Y G C N L R T T F - - - - - - - - T R  SEQ ID NO:74

N Q L A G G W Y L D P N Y W L S V G A Y - - A I  SEQ ID NO:75

R L T E M G A C D A R W A T L A T R T F A Y N Y  SEQ ID NO:76

D G W T R K E G G I G L P W S V Q C E D G Y N Y  SEQ ID NO:77

D S Y P C H L L - - - - - - - - - - - - - - D V  SEQ ID NO:78

V E Y P I A D M C S - - - - - - - - - - - - R Y  SEQ ID NO:79

As stated above, the immunoglobulins of the invention are preferably devoid of the totality of their $C_H1$ domain.

Such immunoglobulins comprise $C_H2$ and $C_H3$ domains in the C-terminal region with respect to the hinge region.

According to a particular embodiment of the invention the constant region of the immunoglobulins comprises $C_H2$ and $C_H3$ domains comprising an amino-acid sequence selected from the following:

for the $C_H2$ domain:

| | |
|---|---|
| APELLGGPTVFIFPPKPKDVLSITLTP | SEQ ID NO:31 |
| APELPGGPSVFVFPTKPKDVLSISGRP | SEQ ID NO:32 |
| APELPGGPSVFVFPPKPKDVLSISGRP | SEQ ID NO:33 |
| APELLGGPSVFIFPPKPKDVLSISGRP | SEQ ID NO:34 | for the $C_H3$ domain:

| | |
|---|---|
| GQTREPQVYTLA | SEQ ID NO:35 |
| GQTREPQVYTLAPXRLEL | SEQ ID NO:36 |
| GQPREPQVYTLPPSRDEL | SEQ ID NO:109 |
| GQPREPQVYTLPPSREEM | SEQ ID NO:110 |
| GQPREPQVYTLPPSQEEM | SEQ ID NO:111 |

Interestingly the inventors have shown that the hinge region of the immunoglobulins of the invention can present variable lengths. When these immunoglobulins act as antibodies, the length of the hinge region will participate to the determination of the distance separating the antigen binding sites.

Preferably an immunoglobulin according to the invention is characterized in that its hinge region comprises from 0 to 50 amino-acids.

Particular sequences of hinge region of the immunoglobulins of the invention are the following.

GTNEVCKCPKCP SEQ ID NO:37
or,
EPKIPQPQPKPQPQPQPQPKPQPKPEPECTCPKCP SEQ ID NO:38

The short hinge region corresponds to an IgG3 molecule and the long hinge sequence corresponds to an IgG2 molecule.

Isolated $V_{HH}$ derived from heavy chain immunoglobulins or $V_{HH}$ libraries corresponding to the heavy chain immunoglobulins can be distinguished from $V_{HH}$ cloning of four-chain model immunoglobulins on the basis of sequence features characterizing heavy chain immunoglobulins.

The camel heavy—chain immunoglobulin $V_{HH}$ region shows a number of differences with the $V_{HH}$ regions derived from 4-chain immunoglobulins from all species examined. At the levels of the residues involved in the $V_{HH}/V_L$ interactions, an important difference is noted at the level of position 45 (FW) which is practically always leucine in the 4-chain immunoglobulins (98%), the other amino acids at this position being proline (1%) or glutamine (1%).

In the camel heavy-chain immunoglobulin, in the sequences examined at present, leucine at position 45 is only found once. It could originate from a four-chain immunoglobulin. In the other cases, it is replaced by arginine, cysteine or glutamic acid residue. The presence of charged amino acids at this position should contribute to making the $V_{HH}$ more soluble.

The replacement by camelid specific residues such as those of position 45 appears to be interesting for the construction of engineered $V_{HH}$ regions derived from the $V_{HH}$ repertoire of 4-chain immunoglobulins.

A second feature specific of the camelid $V_{HH}$ domain is the frequent presence of a cysteine in the $CDR_3$ region associated with a cysteine in the $CDR_1$ position 31 or 33 or $FW_2$ region at position 45. The possibility of establishing a disulphide bond between the $CDR_3$ region and the rest of the variable domain would contribute to the stability and positioning of the binding site.

With the exception of a single pathogenic myeloma protein (DAW) such a disulphide bond has never been encountered in immunoglobulin V regions derived from 4 chain immunoglobulins.

The heavy-chain immunoglobulins of the invention have further the particular advantage of being not sticky. Accordingly these immunoglobulins being present in the serum, aggregate much less than isolated heavy chains of a four-chain immunoglobulins. The immunoglobulins of the invention are soluble to a concentration above 0.5 mg/ml, preferably above 1 mg/ml and more advantageously above 2 mg/ml.

These immunoglobulins further bear an extensive antigen binding repertoire and undergo affinity and specificity maturation in vivo. Accordingly they allow the isolation and the preparation of antibodies having defined specificity, regarding determined antigens.

Another interesting property of the immunoglobulins of the invention is that they can be modified and especially humanized. Especially it is possible to replace all or part of the constant region of these immunoglobulins by all or part of a constant region of a human antibody. For example the $C_H2$ and/or $C_H3$ domains of the immunoglobulin could be replaced by the $C_H2$ and/or $C_H3$ domains of the IgG γ3 human immunoglobulin.

In such humanized antibodies it is also possible to replace a part of the variable sequence, namely one or more of the framework residues which do not intervene in the binding site by human framework residues, or by a part of a human antibody.

Conversely features (especially peptide fragments) of heavy-chain immunoglobulin $V_{HH}$ regions, could be introduced into the $V_H$ or $V_L$ regions derived from four-chain immunoglobulins with for instance the aim of achieving greater solubility of the immunoglobulins.

The invention further relates to a fragment of an immunoglobulin which has been described hereabove and especially to a fragment selected from the following group:

a fragment corresponding to one heavy polypeptide chain of an immunoglobulin devoid of light chains, fragments obtained by enzymatic digestion of the immunoglobulins of the invention, especially those obtained by partial digestion with papain leading to the Fc fragment (constant fragment) and leading to $FV_{HH}h$ fragment (containing the antigen binding sites of the heavy chains) or its dimer $F(V_{HH}h)_2$, or a fragment obtained by further digestion with papain of the Fc fragment, leading to the pFc fragment corresponding to the C-terminal part of the Fc fragment, homologous fragments obtained with other proteolytic enzymes, a fragment of at least 10 preferably 20 amino acids of the variable region of the immunoglobulin, or the complete variable region, especially a fragment corresponding to the isolated $V_{HH}$ domains or to the $V_{HH}$ dimers linked to the hinge disulphide, a fragment corresponding to the hinge region of the immunoglobulin, or to at least 6 amino acids of this hinge region, a fragment of the hinge region comprising a repeated sequence of Pro-X, a fragment corresponding to at least 10 preferably 20 amino acids of the constant region or to the complete constant region of the immunoglobulin.

The invention also relates to a fragment comprising a repeated sequence, Pro-X which repeated sequence contains at least 3 repeats of Pro-X, X being any amino-acid and preferably Gln (glutamine), Lys (lysine) or Glu (acide glutamique); a particular repeated fragment is composed of a 12-fold repeat of the sequence Pro-X.

Such a fragment can be advantageously used as a link between different types of molecules.

The amino-acids of the Pro-X sequence are chosen among any natural or non natural amino-acids.

The fragments can be obtained by enzymatic degradation of the immunoglobulins. They can also be obtained by expression in cells or organisms, of nucleotide sequence coding for the immunoglobulins, or they can be chemically synthesized.

The invention also relates to anti-idiotypes antibodies belonging to the heavy chain immunoglobulin classes. Such anti-idiotypes can be produced against human or animal idiotypes. A property of these anti-idiotypes is that they can be used as idiotypic vaccines, in particular for vaccination against glycoproteins or glycolipids and where the carbohydrate determines the epitope.

The invention also relates to anti-idiotypes capable of recognizing idiotypes of heavy-chain immunoglobulins.

Such anti-idiotype antibodies can be either syngeneic antibodies or allogenic or xenogeneic antibodies.

The invention also concerns nucleotide sequences coding for all or part of a protein which amino-acid sequence comprises a peptide sequence selected from the following:

| | |
|---|---|
| G G S V Q T G G S L R L S C E I S G L T F D | SEQ ID NO:1 |
| G G S V Q T G G S L R L S C A V S G F S F S | SEQ ID NO:2 |
| G G S E Q G G G S L R L S C A I S G Y T Y G | SEQ ID NO:3 |
| G G S V Q P G G S L T L S C T V S G A T Y S | SEQ ID NO:4 |
| G G S V Q A G G S L R L S C T G S G F P Y S | SEQ ID NO:5 |
| G G S V Q A G G S L R L S C V A G F G T S | SEQ ID NO:6 |
| G G S V Q A G G S L R L S C V S F S P S S | SEQ ID NO:7 |
| W G Q G T Q V T V S S | SEQ ID NO:8 |
| W G Q G T L V T V S S | SEQ ID NO:9 |
| W G Q G A Q V T V S S | SEQ ID NO:10 |
| W G Q G T Q V T A S S | SEQ ID NO:11 |
| R G Q G T Q V T V S L | SEQ ID NO:12 |
| A L Q P G G Y C G Y G X - - - - - - - - - - C L | SEQ ID NO:62 |
| V S L M D R I S Q H - - - - - - - - - - - G C | SEQ ID NO:63 |
| V P A H L G P G A I L D L K K Y - - - - - - K Y | SEQ ID NO:64 |
| F C Y S T A G D G G S G E - - - - - - - - - M Y | SEQ ID NO:65 |
| E L S G G S C E L P L L F - - - - - - - - - D Y | SEQ ID NO:66 |
| D W K Y W T C G A Q T G G Y F - - - - - - - G Q | SEQ ID NO:67 |
| R L T E M G A C D A R W A T L A T R T F A Y N Y | SEQ ID NO:68 |
| Q K K D R T R W A E P R E W - - - - - - - - N N | SEQ ID NO:69 |
| G S R F S S P V G S T S R L E S - S D Y - - N Y | SEQ ID NO:70 |
| A D P S I Y Y S I L X I E Y - - - - - - - - K Y | SEQ ID NO:71 |
| D S P C Y M P T M P A P P I R D S F G W - - D D | SEQ ID NO:72 |
| T S S F Y W Y C T T A P Y - - - - - - - - - N V | SEQ ID NO:73 |
| T E I E W Y G C N L R T T F - - - - - - - - T R | SEQ ID NO:74 |
| N Q L A G G W Y L D P N Y W L S V G A Y - - A I | SEQ ID NO:75 |
| R L T E M G A C D A R W A T L A T R T F A Y N Y | SEQ ID NO:76 |
| D G W T R K E G G I G L P W S V Q C E D G Y N Y | SEQ ID NO:77 |
| D S Y P C H L L - - - - - - - - - - - - - - D V | SEQ ID NO:78 |
| V E Y P I A D M C S - - - - - - - - - - - R Y | SEQ ID NO:79 |
| APELLGGPSVFVFPPKPKDVLSISGXPK | SEQ ID NO:39 |
| APELPGGPSVFVFPTKPKDVLSISGRPK | SEQ ID NO:40 |
| APELPGGPSVFVFPPKPKDVLSISGRPK | SEQ ID NO:41 |
| APELLGGPSVFIFPPKPKDVLSISGRPK | SEQ ID NO:42 |
| GQTREPQVYTLAPXRLEL | SEQ ID NO:36 |
| GQPREPQVYTLPPSRDEL | SEQ ID NO:109 |
| GQPREPQVYTLPPSREEM | SEQ ID NO:110 |
| GQPREPQVYTLPPSQEEM | SEQ ID NO:111 |
|                VTVSSGTNEVCKCPKCPAPELPGGPSVFVFP | SEQ ID NO:43 | or,

| | |
|---|---|
| VTVSSEPKIPQPQPKPQPQPQPQPKPQPKPEPECTCPKCPAPELLGGPSVFIFP | SEQ ID NO:44 |

| | |
|---|---|
| GTNEVCKCPKCP | SEQ ID NO:37 |
| APELPGGPSVFVFP | SEQ ID NO:45 |
| EPKIPQPQPKPQPQPQPQPKPQPKPEPECTCPKCP | SEQ ID NO:38 |
| APELLGGPSVFIFP | SEQ ID NO:46 |

Such nucleotide sequences can be deduced from the amino-acid sequences taking into account the deneneracy of the genetic code. They can be synthesized or isolated from cells producing immunoglobulins of the invention.

A procedure for the obtention of such DNA sequences is described in the examples.

The invention also contemplates RNA, especially mRNA sequences corresponding to these DNA sequences, and also corresponding cDNA sequences.

The nucleotide sequences of the invention can further be used for the preparation of primers appropriate for the detection in cells or screening of DNA or cDNA libraries to isolate nucleotide sequences coding for immunoglobulins of the invention.

Such nucleotide sequences can be used for the preparation of recombinant vectors and the expression of these sequences contained in the vectors by host cells especially prokaryotic cells like bacteria or also eukaryotic cells and for example CHO cells, insect cells, simian cells like Vero cells, or any other mammalian cells. Especially the fact that the immunoglobulins of the invention are devoid of light chains permits to secrete them in eukaryotic cells since there is no need to have recourse to the step consisting in the formation of the BIP protein which is required in the four-chain immunoglobulins.

The inadequacies of the known methods for producing monoclonal antibodies or immunoglobulins by recombinant DNA technology comes from the necessity in the vast majority of cases to clone simultaneously the $V_H$ and $V_L$ domains corresponding to the specific binding site of 4 chain immunoglobulins. The animals and especially camelids which produce heavy-chain immunoglobulins according to the invention, and possibly other vertebrate species are capable of producing heavy-chain immunoglobulins of which the binding site is located exclusively in the $V_{HH}$ domain. Unlike the few heavy-chain immunoglobulins produced in other species by chain separation or by direct cloning, the camelid heavy-chain immunoglobulins have undergone extensive maturation in vivo. Moreover their V region has naturally evolved to function in absence of the $V_L$. They are therefore ideal for producing monoclonal antibodies by recombinant DNA technology. As the obtention of specific antigen binding clones does not depend on a stochastic process necessitating a very large number of recombinant cells, this allows also a much more extensive examination of the repertoire.

This can be done at the level of the non rearranged $V_{HH}$ repertoire using DNA derived from an arbitrarily chosen tissue or cell type or at the level of the rearranged $V_{HH}$ repertoire, using DNA obtained from B lymphocytes. More interesting however is to transcribe the mRNA from antibody producing cells and to clone the cDNA with or without prior amplification into an adequate vector. This will result in the obtention of antibodies which have already undergone affinity maturation.

The examination of a large repertoire should prove to be particularly useful in the search for antibodies with catalytic activities.

The invention thus provides libraries which can be generated in a way which includes part of the hinge sequence, the identification is simple as the hinge is directly attached to the $V_{HH}$ domain.

These libraries can be obtained by cloning cDNA from lymphoid cells with or without prior PCR amplification. The PCR primers are located in the promoter, leader or framework sequences of the $V_{HH}$ for the 5' primer and in the hinge, $CH_2$, $CH_3$, 3' untranslated region or polyA tail for the 3' primer. A size selection of amplified material allows the construction of a library limited to heavy chain immunoglobulins.

In a particular example, the following 3' primer in which a KpnI site has been constructed and which corresponds to amino-acids 313 to 319 (CGC CAT CAA GGT AAC AGT TGA SEQ ID NO:47) is used in conjunction with mouse $V_{HH}$ primers described by Sestry et al and containing a Xho site

AG GTC CAG CTG CTC GAG TCT GG SEQ ID NO:48

AG CTC CAG CTG CTC GAG TCT GG SEQ ID NO:49

AG GTC CAG CTT <u>CTC GAG</u> TCT GG SEQ ID NO:50
               XhoI site

These primers yield a library of camelid heavy chain immunoglobulins comprising the $V_{HH}$ region (related to mouse or human subgroup III), the hinge and a section of $CH_2$.

In another example, the cDNA is polyadenylated at its 5' end and the mouse specific $V_{HH}$ primers are replaced by a poly T primer with an inbuilt XhoI site, at the level of nucleotide 12.

$CTCGAGT_{12}$.

The same 3' primer with a KpnI site is used.

This method generates a library containing all subgroups of immunoglobulins.

Part of the interest in cloning a region encompassing the hinge-$CH_2$ link is that in both γ2 and γ3, a Sac site is present immediately after the hinge. This site allows the grafting of the sequence coding for the $V_{HH}$ and the hinge onto the Fc region of other immunoglobulins, in particular the human $IgG_1$ and $IgG_3$ which have the same amino acid sequence at this site ($Glu_{246}$ $Leu_{247}$)

As an example, the invention contemplates a cDNA library composed of nucleotide sequences coding for a heavy-chain immunoglobulin, such as obtained by performing the following steps:

a) treating a sample containing lymphoid cells, especially periferal, lymphocytes, spleen cells, lymph nodes or another lyphoid tissue from a healthy animal, especially selected among the Camelids, in order to separate the lymphoid cells, b) separating polyadenylated RNA from the other nucleic acids and components of the cells, c) reacting the obtained RNA with a reverse transcriptase in order to obtain the corresponding cDNA, d) contacting the cDNA of step c) with 5' primers corresponding to mouse $V_H$ domain of four-chain immunoglobulins, which primer contains a determined restriction site, for example an XhoI site and with 3' primers corresponding to the N-terminal part of a $C_H2$ domain containing a KpnI site, e) amplifying the DNA, f) cloning the amplified sequence in a vector, especially in a bluescript vector, g) recovering the clones hybridizing with a probe corresponding to the sequence coding for a constant domain from an isolated heavy-chain immunoglobulin.

This cloning gives rise to clones containing DNA sequences including the sequence coding for the hinge. It thus permits the characterization of the subclass of the immunoglobulin and the SacI site useful for grafting the $FV_{HH}h$ to the Fc region.

The recovery of the sequences coding for the heavy-chain inmunoglobulins can also be achieved by the selection of clones containing DNA sequences having a size compatible with the lack of the $C_H1$ domain.

It is possible according to another embodiment of the invention, to add the following steps between steps c) and d) of the above process:

in the presence of a DNA polymerase and of deoxyribonucleotide triphosphates, contacting said cDNA with oligonucleotide degenerated primers, which sequences are capable of coding for the hinge region and N-terminal $V_{HH}$ domain of an immunoglobulin, the primers being capable of hybridizing with the cDNA and capable of initiating the extension of a DNA sequence complementary to the cDNA used as template, recovering the amplified DNA.

The clones can be expressed in several types of expression vectors. As an example using a commercially available vector Immuno PBS (Huse et al: Science (1989) 246, 1275), clones produced in Bluescript® according to the above described procedure, are recovered by PCR using the same XhoI containing 5' primer and a new 3' primer, corresponding to residues 113–103 in the framework of the immunoglobulins, in which an Spe site has been constructed: TC TTA ACT AGT GAG GAG ACG GTG ACC TG SEQ ID NO:51. This procedure allows the cloning of the $V_{HH}$ in the Xho/Spe site of the Immuno PBS vector. However, the 3' end of the gene is not in phase with the identification "tag" and the stop codon of the vector. To achieve this, the construct is cut with Spe and the 4 base overhangs are filled in, using the Klenow fragment after which the vector is religated. A further refinement consists in replacing the marker ("tag") with a poly histidine so that metal purification of the cloned $V_{HH}$ can be performed. To achieve this a Spe/EcoRI double stranded oligonucleotide coding for 6 histidines and a termination codon is first constructed by synthesis of both strands followed by heating and annealing:

CTA GTG CAC CAC CAT CAC CAT CAC TAA* TAG* SEQ ID NO:52

AC GTG GTG GTA GTG GTA GTG ATT ATC TTA A SEQ ID NO:53

The vector containing the insert is then digested with SpeI and EcoRI to remove the resident "tag" sequence which can be replaced by the poly-His/termination sequence. The produced $V_{HH}$ can equally be detected by using antibodies raised against the dromedary $V_{HH}$ regions. Under laboratory conditions, $V_{HH}$ regions are produced in the Immuno PBS vector in mg amounts per liter.

The invention also relates to a DNA library composed of nucleotide sequences coding for a heavy-chain immunoglobulin, such as obtained from cells with rearranged immunoglobulin genes.

In a preferred embodiment of the invention, the library is prepared from cells from an animal previously immunized against a determined antigen. This allows the selection of antibodies having a preselected specificity for the antigen used for immunization.

In another embodiment of the invention, the amplification of the cDNA is not performed prior to the cloning of the cDNA.

The heavy-chain of the four-chain immunoglobulins remains sequestered in the cell by a chaperon protein (BIP) until it has combined with a light chain. The binding site for the chaperon protein is the $C_H1$ domain. As this domain is absent from the heavy chain immunoglobulins, their secretion is independent of the presence of the BIP protein or of the light chain. Moreover the inventors have shown that the obtained immunoglobulins are not sticky and accordingly will not abnormally aggregate.

The invention also relates to a process for the preparation of a monoclonal antibody directed against a determined antigen, the antigen binding site of the antibody consisting of heavy polypeptide chains and which antibody is further devoid of light polypeptide chains, which process comprises:

immortalizing lymphocytes, obtained for example from the peripheral blood of Camelids previously immunized with a determined antigen, with an immortal cell and preferably with myeloma cells, in order to form a hybridoma, culturing the immortalized cells (hybridoma) formed and recovering the cells producing the antibodies having the desired specificity.

The preparation of antibodies can also be performed without a previous immunization of Camelids.

According to another process for the preparation of antibodies, the recourse to the technique of the hybridoma cell is not required.

According to such process, antibodies are prepared in vitro and they can be obtained by a process comprising the steps of:

cloning into vectors, especially into phages and more particularly filamentous bacteriophages, DNA or cDNA sequences obtained from lymphocytes especially PBLs of Camelids previously immunized with determined antigens, transforming prokaryotic cells with the above vectors in conditions allowing the production of the antibodies, selecting the antibodies for their heavy-chain structure and further by subjecting them to antigen-affinity selection, recovering the antibodies having the desired specificity, In another embodiment of the invention the cloning is performed in vectors, especially into plasmids coding for bacterial membrane proteins. Procaryotic cells are then transformed with the above vectors in conditions allowing the expression of antibodies in their membrane.

The positive cells are further selected by antigen affinity selection.

The heavy chain antibodies which do not contain the $C_H1$ domain present a distinct advantage in this respect. Indeed, the $C_H1$ domain binds to BIP type chaperone proteins present within eukaryotic vectors and the heavy chains are not transported out of the endocytoplasmic reticulum unless light chains are present. This means that in eukaryotic cells, efficient cloning of 4-chain immunoglobulins in non mammalian cells such as yeast cells can depend on the properties of the resident BIP type chaperone and can hence be very difficult to achieve. In this respect the heavy chain antibodies of the invention which lack the $CH_1$ domain present a distinctive advantage.

In a preferred embodiment of the invention the cloning can be performed in yeast either for the production of antibodies or for the modification of the metabolism of the yeast. As example, Yep 52 vector can be used. This vector has the origin of replication (ORI) $2\mu$ of the yeast together with a selection marker Leu 2.

The cloned gene is under the control of gal1 promoter and accordingly is inducible by galactose. Moreover, the expression can be repressed by glucose which allows the obtention of very high concentration of cells before the induction.

The cloning between BamHI and SalI sites using the same strategy of production of genes by PCR as the one described above, allows the cloning of camelid immunoglobulin genes in *E. coli*. As example of metabolic modulation which can be obtained by antibodies and proposed for the yeast, one can site the cloning of antibodies directed against cyclins, that is proteins involved in the regulation of the cellular cycle of the yeast (TIBS 16 430 J. D. Mc Kinney, N. Heintz 1991). Another example is the introduction by genetic engineering of an antibody directed against $CD_{28}$, which antibody would be inducible (for instance by gal1), within the genome of the yeast. The $CD_{28}$ is involved at the level of the initiation of cell division, and therefore the expression of antibodies against this molecule would allow an efficient control of multiplication of the cells and the optimization of methods for the production in bioreactors or by means of immobilized cells.

In yet another embodiment of the invention, the cloning vector is a plasmid or a eukaryotic virus vector and the cells to be transformed are eukaryotic cells, especially yeast cells, mammalian cells for example CHO cells or simian cells such as Vero cells, insect cells, plant cells, or protozoan cells.

For more details concerning the procedure to be applied in such a case, reference is made to the publication of Marks et al, J. Mol. Biol. 1991, 222:581–597.

Furthermore, starting from the immunoglobulins of the invention, or from fragments thereof, new immunoglobulins or derivatives can be prepared.

Accordingly immunoglobulins replying to the above given definitions can be prepared against determined antigens. Especially the invention provides monoclonal or polyclonal antibodies devoid of light polypeptide chains or antisera containing such antibodies and directed against determined antigens and for example against antigens of pathological agents such as bacteria, viruses or parasites. As example of antigens or antigenic determinants against which antibodies could be prepared, one can cite the envelope glycoproteins of viruses or peptides thereof, such as the external envelope glycoprotein of a HIV virus, the surface antigen of the hepatitis B virus.

Immunoglobulins of the invention can also be directed against a protein, hapten, carbohydrate or nucleic acid.

Particular antibodies according to the invention are directed against the galactosyl$\alpha$-1-3-galactose epitope.

The immunoglobulins of the invention allow further the preparation of combined products such as the combination of the heavy-chain immunoglobulin or a fragment thereof with a toxin, an enzyme, a drug, a hormone.

As example one can prepare the combination of a heavy-chain immunoglobulin bearing an antigen binding site recognizing a myeloma immunoglobulin epitope with the abrin or mistletoe lectin toxin. Such a construct would have its uses in patient specific therapy.

Another advantageous combination is that one can prepare between a heavy-chain immunoglobulins recognizing an insect gut antigen with a toxin specific for insects such as the toxins of the different serotypes of *Bacillus thuringiensis* or *Bacillus sphaericus*. Such a construct cloned into plants can be used to increase the specificity or the host range of existing bacterial toxins.

The invention also proposes antibodies having different specificities on each heavy polypeptide chains. These multifunctional, especially bifunctional antibodies could be prepared by combining two heavy chains of immunoglobulins of the invention or one heavy chain of an immunoglobulin of the invention with a fragment of a four-chain model immunoglobulin.

The invention also provides hetero-specific antibodies which can be used for the targetting of drugs or any biological substance like hormones. In particular they can be used to selectively target hormones or cytokines to a limited category of cells. Examples are a combination of a murine or human antibody raised against interleukin 2 ($IL_2$) and a heavy-chain antibody raised against $CD_4$ cells. This could be used to reactivate $CD_4$ cells which have lost their $IL_2$ receptor.

The heavy-chain immunoglobulins of the invention can also be used for the preparation of heterospecific antibodies. These can be achieved either according to the above described method by reduction of the bridges between the different chains and reoxydation, according to the usual techniques, of two antibodies having different specificities, but it can also be achieved by serial cloning of two antibodies for instance in the Immuno pBS vector.

In such a case, a first gene corresponding to the $V_{HH}$ domain comprised between Xho site and a Spe site is prepared as described above. A second gene is then prepared through an analogous way by using as 5' extremity a primer containing a Spe site, and as 3' extremity a primer containing a termination codon and an EcoRI site. The vector is then digested with EcoRI and XhoI and further both $V_{HH}$ genes are digested respectively by Xho/Spe and by Spe/EcoRI.

After ligation, both immunoglobulin genes are serially cloned. The spacing between both genes can be increased by the introduction of addition codons within the 5' SpeI primer.

In a particular embodiment of the invention, the hinge region of IgG2 immunoglobulins according to the invention is semi-rigid and is thus appropriate for coupling proteins. In such an application proteins or peptides can be linked to various substances, especially to ligands through the hinge region used as spacer. Advantageously the fragment comprises at least 6 amino acids.

According to the invention it is interesting to use a sequence comprising a repeated sequence Pro-X, X being any amino-acid and preferably Gln, Lys or Glu, especially a fragment composed of at least a 3-fold repeat and preferably of a 12-fold repeat, for coupling proteins to ligand, or for assembling different protein domains.

The hinge region or a fragment thereof can also be used for coupling proteins to ligands or for assembling different protein domains.

Usual techniques for the coupling are appropriate and especially reference may be made to the technique of protein engineering by assembling cloned sequences.

The antibodies according to this invention could be used as reagents for the diagnosis in vitro or by imaging techniques. The immunoglobulins of the invention could be labelled with radio-isotopes, chemical or enzymatic markers or chemiluminescent markers.

As example and especially in the case of detection or observation with the immunoglobulins by imaging techniques, a label like technetium, especially technitium 99 is advantageous. This label can be used for direct labelling by a coupling procedure with the immunoglobulins or fragments thereof or for indirect labelling after a step of preparation of a complex with the technitium.

Other interesting radioactive labels are for instance indium and especially indium 111, or iodine, especially $I^{131}$, $I^{125}$ and $I^{123}$.

For the description of these techniques reference is made to the FR patent application published under number 2649488.

In these applications the small size of the $V_{HH}$ fragment is a definitive advantage for penetration into tissue.

The invention also concerns monoclonal antibodies reacting with anti-idiotypes of the above-described antibodies.

The invention also concerns cells or organisms in which heavy-chain immunoglobulins have been cloned. Such cells or organisms can be used for the purpose of producing heavy-chain immunoglobulins having a desired preselected specificity, or corresponding to a particular repertoire. They can also be produced for the purpose of modifying the metabolism of the cell which expresses them. In the case of modification of the metabolism of cells transformed with the sequences coding for heavy-chain immunoglobulins, these produced heavy-chain immunoglobulins are used like antisense DNA. Antisense DNA is usually involved in blocking the expression of certain genes such as for instance the variable surface antigen of trypanosomes or other pathogens. Likewise, the production or the activity of certain proteins or enzymes could be inhibited by expressing antibodies against this protein or enzyme within the same cell.

The invention also relates to a modified 4-chain immunoglobulin or fragments thereof, the $V_H$ regions of which has been partialy replaced by specific sequences or amino acids of heavy chain immunoglobulins, especially by sequences of the $V_{HH}$ domain. A particular modified $V_H$ domain of a four-chain immunoglobulin, is characterized in that the leucine, proline or glutamine in position 45 of the $V_H$ regions has been replaced by other amino acids and preferably by arginine, glutamic acid or cysteine.

A further modified $V_H$ or $V_L$ domain of a four-chain immunoglobulin, is characterized by linking of CDR loops together or to FW regions by the introduction of paired cysteines, the CDR region being selected between the $CDR_1$ and the $CDR_3$, the FW region being the $FW_2$ region, and especially in which one of the cysteines introduced is in position 31, 33 of the $CDR_1$ or 45 of $FW_2$ and the other in $CDR_3$.

Especially the introduction of paired cysteines is such that the $CDR_3$ loop is linked to the FW2 or CDR1 domain and more especially the cysteine of the CDR3 of the $V_H$ is linked to a cysteine in position 31, 33 of the $CDR_1$ or in position 45 of $FW_2$.

In another embodiment of the invention, plant cells can be modified by the heavy-chain immunoglobulins according to the invention, in order that they acquire new properties or increased properties.

The heavy-chain immunoglobulins of the invention can be used for gene therapy of cancer for instance by using antibodies directed against proteins present on the tumor cells.

In such a case, the expression of one or two $V_{HH}$ genes can be obtained by using vectors derived from parvo or adeno viruses. The parvo viruses are characterized by the fact that they are devoid of pathogenicity or almost not pathogenic for normal human cells and by the fact that they are capable of easily multiplying in cancer cells (Russel S. J. 1990, Immunol. Today II. 196–200).

The heavy-chain immunoglobulins are for instance cloned within HindIII/XbaI sites of the infectious plasmid of the murine MVM virus (pMM984). (Merchlinsky et al, 1983, J. Virol. 47, 227–232) and then placed under the control of the MVM38 promoter.

The gene of the $V_{HH}$ domain is amplified by PCR by using a 5' primer containing an initiation codon and a HindIII site, the 3' primer containing a termination codon and a XbaI site.

This construct is then inserted between positions 2650 (HindIII) and 4067 (XbaI) within the plasmid.

The efficiency of the cloning can be checked by transfection. The vector containing the antibody is then introduced in permissive cells (NB-E) by transfection.

The cells are recovered after two days and the presence of $V_{HH}$ regions is determined with an ELISA assay by using rabbit antiserum reacting with the $V_{HH}$ part.

The invention further allows the preparation of catalytic antibodies through different ways. The production of antibodies directed against components mimicking activated states of substrates (as example vanadate as component mimicking the activated state of phosphate in order to produce their phosphoesterase activities, phosphonate as compound mimicking the peptidic binding in order to produce proteases) permits to obtain antibodies having a catalytic function. Another way to obtain such antibodies consists in performing a random mutagenesis in clones of antibodies for example by PCR, in introducing abnormal bases during the amplification of clones. These amplified fragments obtained by PCR are then introduced within an appropriate vector for cloning. Their expression at the surface of the bacteria permits the detection by the substrate of clones having the enzymatic activity. These two approaches can of course be combined. Finally, on the basis of the data available on the structure, for example the data obtained by XRay crystallography or NMR, the modifications can be directed. These modifications can be performed by usual techniques of genetic engineering or by complete synthesis. One advantage of the $V_{HH}$ of the heavy chain immunoglobulins of the invention is the fact that they are sufficiently soluble.

The heavy chain immunoglobulins of the invention can further be produced in plant cells, especially in transgenics plants. As example the heavy chain immunoglobulins can be produced in plants using the pMon530 plasmid (Roger et al. Meth Enzym 153 1566 1987) constitutive plant expression vector as has been described for classical four chain antibodies (Hiat et al. Nature 342 76–78, 1989) once again using the appropriate PCR primers as described above, to generate a DNA fragment in the right phase.

Other advantages and characteristics of the invention will become apparent in the examples and figures which follow.

FIGURES

FIG. 1(A), (B) and (C)

Characterisation and purification of camel IgG by affinity chromatography on Protein A and Protein G sepharose (Pharmacia)

FIG. (A) shows, after reduction, the SDS-PAGE protein profile of the adsorbed and non adsorbed fractions of *Camelus dromedarius* serum. The fraction adsorbed on Protein A and eluted with NaCl 0.15 M acetic acid 0.58% show upon reduction (lane c) three heavy chain components of respectively 50, 46 and 43 Kd and light chain (rabbit IgG in lane a). The fractions adsorbed on a Protein G Sepharose (Pharmacia) derivative which has been engineered to delete the albumin binding region (lane e) and eluted with 0.1 M gly HCl pH 2.7 lacks the 46 Kd heavy chain which is recovered in the non adsorbed fraction (lane f). None of these components are present in the fraction non adsorbed on Protein A (lane d), lane b contains the molecular weight markers.

FIGS. (B) and (C) By differential elution, immunoglobulin fractions containing the 50 and 43 Kd heavy chain can be separated. 5 ml of *C. dromadarius* serum is adsorbed onto a 5 ml Protein G sepharose column and the column is extensively washed with 20 mM phosphate buffer, pH 7.0. Upon elution with pH 3.5 buffer (0.15 M NaCl, 0.58% acetic acid) a 100 Kd component is eluted which upon reduction yields a 43 Kd heavy chain, (lane 1). After column eluant absorbance has fallen to background level a second immunoglobulin component of 170 Kd can be eluted with pH 2.7 buffer (0.1 M glycine HC). This fraction upon reduction yields a 50 Kd heavy chain and a board light chain band (lane 2). The fraction non adsorbed on Protein G is then brought on a 5 ml Protein A Sepharose column. After washing and elution with pH 3.5 buffer (0.15 M NaCl, 0.58% acetic acid) a third immunoglobulin of 100 Kd is obtained which consists solely of 46 Kd heavy chains (lane 3).

FIG. 2(A) and (B)

Immunoglobulins of *Camelus bactrianus, Lama vicugna, Lama glama* and *Lama pacos* to Protein A (A lanes) and to Protein G (G lanes) analyzed on SDS-PAGE before FIG. (A) and after reduction FIG. (B)

10 µl of serum obtained from the different species were added to Eppendorf® tubes containing 10 mg of Protein A or Protein G sepharose suspended in 400 µl of pH 8.3 immunoprecipitation buffer (NaCl 0.2. M, Tris 0.01 M; EDTA 0.01 M, Triton X100 1%, ovalbumin 0.1%). The tubes were slowly rotated for 2 hours at 4° C. After centrifugation the pellets were washed 3 times in buffer and once in buffer in which the Triton and ovalbumin had been ommitted. The pellets were then resuspended in the SDS-PAGE sample solution 70 µl per pellet with or without dithiotreitol as reductant. After boiling for 3 min at 100° C., the tubes were centrifuged and the supernatants analysed.

In all species examined the unreduced fractions FIG. (A) contain in addition to molecules of approximately 170 Kd also smaller major components of approximately 100 Kd. In the reduced sample FIG. (B) the constituant heavy and light chains are detected. In all species a heavy chain component (marked by an asterisk *) is present in the material eluted from the Protein A but absent in the material eluted from the Protein G.

FIG. 3(A) and (B)

$IgG_1$, $IgG_2$ and $IgG_3$ were prepared from serum obtained from healthy or *Trypanosama evansi* infected *Camelus dromedarius* (CATT titer 1/160 (3) and analysed by radioimmunopreci- pitation or Western Blotting for anti trypanosome activity FIG. (A) $^{35}S$ methionine labelled *Trypanosome evansi* antigens lysate (500.000 counts) was added to Eppendorf tubes containing 10 µl of serum or, 20 µg of $IgG_1$, $IgG_2$ or $IgG_3$ in 200 µl of pH 8.3 immunoprecipitation buffer containing 0.1 M TLCK as proteinase inhibitor and slowly rotated at 4° C. during one hour. The tubes were then supplemented with 10 mg of Protein A Sepharose suspended in 200 µl of the same pH 8.3 buffer and incubated at 4° C. for an additional hour.

After washing and centrifugation at 15000 rpm for 12 s, each pellet was resuspended in 75 µl SDS-PAGE sample solution containing DTT and heated for 3 min. at 100° C. After centrifugation in an Eppendorf minifuge at 15000 rpm for 30 s, 5 µl of the supernatant was saved for radioactivity determination and the reminder analysed by SDS-PAGE and fluorography. The counts/5 µl sample are inscribed on for each line.

FIG. (B) 20 µg of $IgG_1$, $IgG_2$ and $IgG_3$ from healthy and trypanosome infected animals were separated by SDS-PAGE without prior reduction or heating. The separated samples were then electro transferred to a nitrocellulose membrane, one part of the membrane was stained with Ponceau Red to localise the protein material and the reminder incubated with 1% ovalbumin in TST buffer (Tris 10 mM, NaCl 150 mM, Tween 0.05%) to block protein binding sites.

After blocking, the membrane was extensively washed with TST buffer and incubated for 2 hours with $^{35}$S-labelled trypanosome antigen. After extensive washing, the membrane was dried and analysed by autoradiography. To avoid background and unspecific binding, the labelled trypanosome lysate was filtered through a 45 μ millipore filter and incubated with healthy camel immunoglobulin and ovalbumin adsorbed on a nitrocellulose membrane.

FIG. 4(A) and (B)

Purified IgG3 of the camel, by affinity chromatography on Protein A Sepharose are partially digested with papain and separated on Protein A sepharose.

14 mg of purified IgG3 were dissolved in 0.1 M phosphate buffer pH 7.0 containing 2 mM EDTA. They were digested by 1 hour incubation at 37° C. with mercurypapain (1% enzyme to protein ratio) activated by $5.10^4$ M cysteine. The digestion was blocked by the addition of excess iodoacetamide $(4.10^2 M)(13)$. After centrifugation of the digest in an ependorf centrifuge for 5 min at 15000 rpm, the papain fragments were separated on a protein A Sepharose column into binding (B) and non binding (NB) fractions. The binding fraction was eluted from the column with 0.1M glycine HCl buffer pH 1.7.

FIG. 5

Schematic presentation of a model for IgG3 molecules devoid of light chains

FIG. 6

Schematic representation of immunoglobulins having heavy polypeptide chains and devoid of light chains, regarding conventional four-chain model immunoglobulin. Representation of a hinge region

FIG. 7

Alignement of 17 $V_{HH}$ DNA sequences of Camel heavy chain immunoglobulins SEQ ID NOS:92–108

FIG. 8

Expression and purification of the camel $V_{HH}21$ protein from *E.coli*

I HEAVY CHAIN ANTIBODIES IN CAMELIDS

Figure 1B:
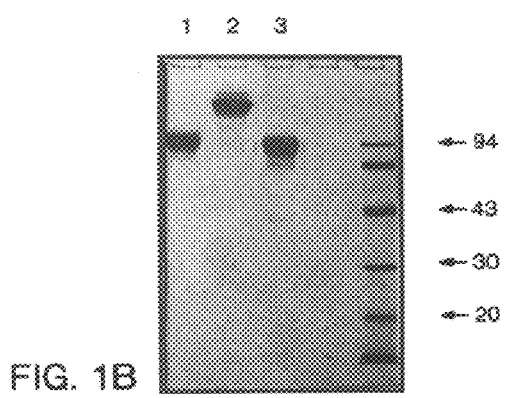
Figure 1C:
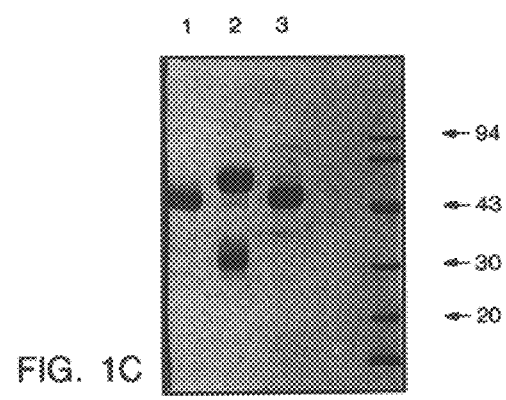

When *Camelus dromedarius* serum is adsorbed on Protein G sepharose, an appreciable amount (25–35%) of immunoglobulins (Ig) remains in solution which can then be recovered by affinity chromatography on Protein A sepharose (FIG. 1A). The fraction adsorbed on Protein G can be differentially eluted into a tightly bound fraction (25%) consisting of molecules of an unreduced apparent molecular weight (MW) of 170 Kd and a more weakly bound fraction (30–45%) having an apparent molecular weight of 100 Kd (FIG. 1B). The 170 Kd component when reduced yields 50 Kd heavy chains and large 30 Kd light chains. The 100 Kd fraction is totally devoid of light chains and appears to be solely composed of heavy chains which after reduction have on apparent MW of 43 Kd (FIG. 1C). The fraction which does not bind to Protein G can be affinity purified and eluted from a Protein A column as a second 100 Kd component which after reduction appears to be composed solely of 46 Kd heavy chains.

The heavy chain immoglobulins devoid of light chains total up to 75% of the molecules binding to Protein A.

As all three immunoglobulins bind to Protein A we refer to them as IgG: namely $IgG_1$ (light chain and heavy chain γ1 (50 Kd) binding to Protein G, $IgG_2$ (heavy chain γ2 (46 Kd) non binding to Protein G and $IgG_3$ (heavy chain γ3 (43 Kd) binding to Protein G. There is a possibility that these three sub(classes) can be further subdivided.

Figure 2A:
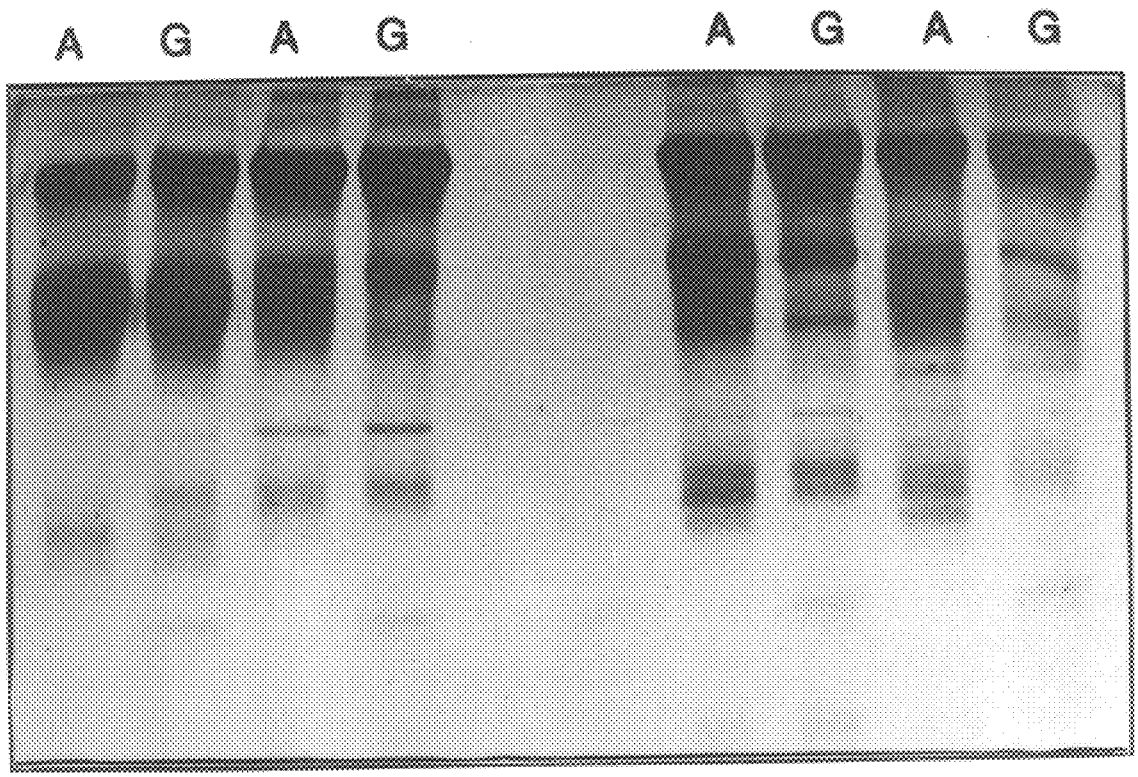
Figure 2B:
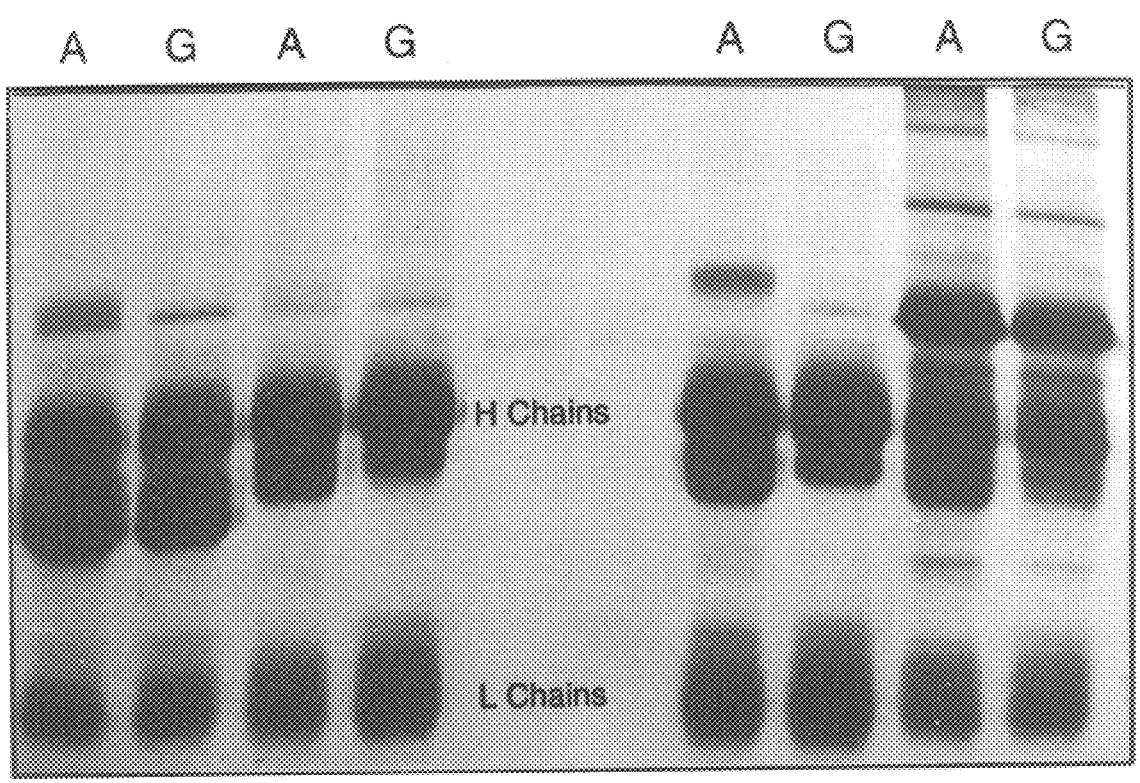

A comparative study of old world camelids (*Camelus bactrianus* and *Camelus dromedarius*) and new world camelids (*lama pacos, lama glama, lama vicugna*) showed that heavy chain immunoglobulins are found in all species examined, albeit with minor differences in apparent molecular weight and proportion. The new world camelids differs from the old world camelids in having a larger $IgG_3$ molecule (heavy chain immunoglobulin binding to Protein G) in which the constituent heavy chains have an apparent molecular weight of 47 Kd (FIG. 2A and B).

The abundance of the heavy chain immunoglobulins in the serum of camelids raises the question of what their role is in the immune response and in particular whether they bear antigen binding specificity and if so how extensive is the repertoire. This question could be answered by examining the immunoglobulins from *Trypanosoma evansi* infected camels (*Camelus dromedarius*).

Figure 3A:
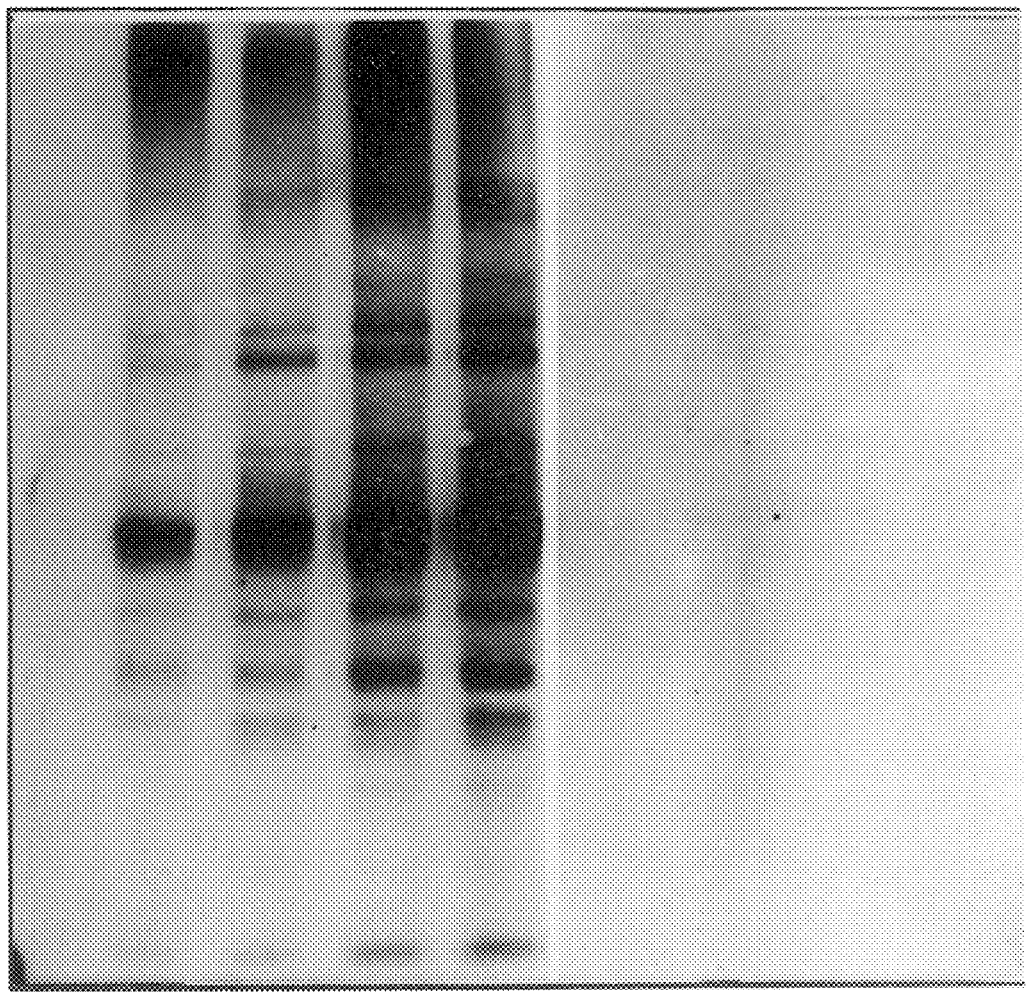

For this purpose, the corresponding fractions of $IgG_1$, $IgG_2$, $IgG_3$ were prepared from the serum of a healthy camel and from the serum of camels with a high antitrypanosome titer, measured by the Card Agglutination Test (3). In radioimmunoprecipitation, $IgG_1$, $IgG_2$ and $IgG_3$ derived from infected camel indicating extensive repertoire heterogeneity and complexity (FIG. 3A) were shown to bind a large number of antigens present in a $^{35}$S methionine labelled trypanosome lysate.

Figures 3B, 3C:
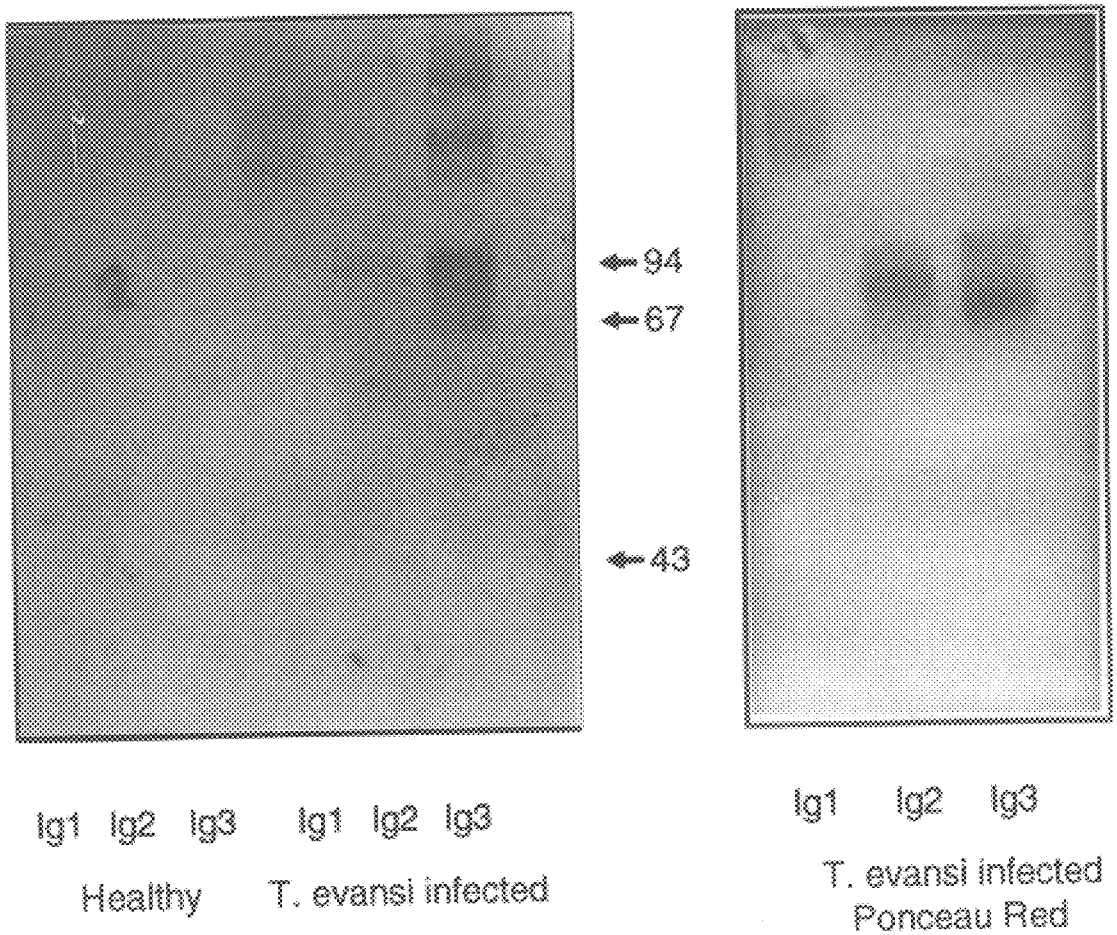

In blotting experiments $^{35}$S methionine labelled trypanosome lysate binds to SDS PAGE separated $IgG_1$, $IgG_2$ and $IgG_3$ obtained from infected animals (FIG. 3B).

This leads us to conclude that the camelid heavy chain $IgG_2$ and $IgG_3$ are bona fide antigen binding antibodies.

An immunological paradigm states that an extensive antibody repertoire is generated by the combination of the light and heavy chain variable V region repertoires (6). The heavy chain immunoglobulins of the camel seem to contradict this paradigm.

Immunoglobulins are characterized by a complex I.E.F. (isoelectric focussing) pattern reflecting their extreme heterogeneity. To determine whether the two heavy chains constituting the $IgG_2$ and $IgG_3$ are identical or not, the isoelectric focussing (I.E.F.) pattern were observed before and after chain separation by reduction and alkylation using iodoacetamide as alkylating agent.

As this alkylating agent does not introduce additional charges in the molecule, the monomers resulting from the reduction and alkylation of a heavy chain homodimer will have practically the same isolectric point as the dimer, whereas if they are derived from a heavy chain heterodimer, the monomers will in most cases differ sufficiently in isoelectric point to generate a different pattern in I.E.F.

Upon reduction, and alkylation by iodoacetamide the observed pattern is not modified for the *Camelus dromedarius* $IgG_2$ and $IgG_3$ indicating that these molecules are each composed of two identical heavy chains which migrate to the same position as the unreduced molecule they originated from.

In contrast, the I.E.F. pattern of $IgG_1$ is completely modified after reduction as the isoelectric point of each molecule is determined by the combination of the isoelectric points of the light and heavy chains which after separation will each migrate to a different position.

These findings indicate that the heavy chains alone can generate an extensive repertoire and question the contribution of the light chain to the useful antibody repertoire. If this necessity be negated, what other role does the light chain play.

Normally, isolated heavy chain from mammalian immunoglobulins tend to aggregate considerably but are only solubilized by light chains (8, 9) which bind to the $C_H1$ domain of the heavy chain.

In humans and in nice a number of spontaneous or induced myelomas produce a pathological immunoglobulin solely composed of heavy chains (heavy chain disease). These myeloma protein heavy chains carry deletions in the $C_H1$ and $V_{HH}$ domains (10). The reason why full lenght heavy chains do not give rise to secreted heavy chain in such pathological immunoglobulins seems to stem from the fact that the synthesis of Ig involves a chaperoning protein, the immunoglobulin heavy chain binding protein or BIP (11), which normally is replaced by the light chain (12). It is possible that the primordial role of the light chain in the four-chain model immunoglobulins is that of a committed heavy chain chaperon and that the emergence of light chain repertoires has just been an evolutionary bonus.

The camelid γ2 and γ3 chains are considerably shorter than the normal mammalian γ chain. This would suggest that deletions have occurred in the $C_H1$ domain. Differences in sizes of the γ2 and γ3 immunoglobulins of old and new world camelids suggests that deletions occurred in several evolutionary steps especially in the $C_H1$ domain.

II THE HEAVY CHAIN IMMUNOGLOBULINS OF THE CAMELIDS LACK THE $C_H1$ DOMAIN

The strategy followed for investigating the heavy chain immunoglobulin primary structure is a combination of protein and cDNA sequencing; the protein sequencing is necessary to identify sequence streches characteristic of each immunoglobulin. The N-terminal of the immunoglobulin being derived from the heavy chain variable region repertoire only yields information on the $V_{HH}$ subgroups (variable region of the heavy chain) and cannot be used for class or subclass identification. This means that sequence data had to be obtained from internal enzymatic or chemical cleavage sites.

A combination of papain digestion and Protein A affinity chromatography allowed the separation of various fragments yielding information on the general structure of IgG3.

Figure 4A:
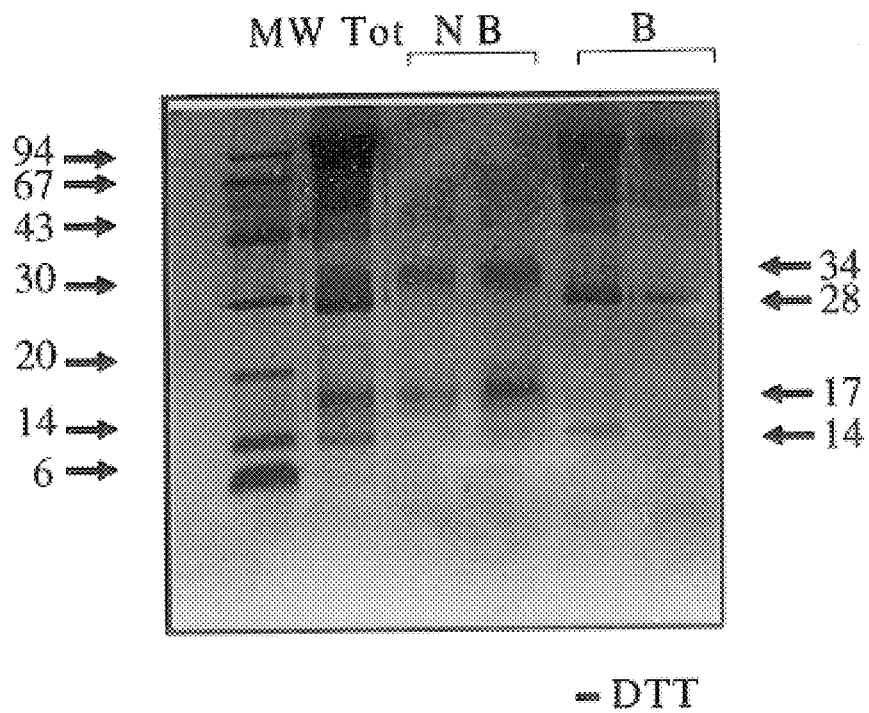
Figure 4B:
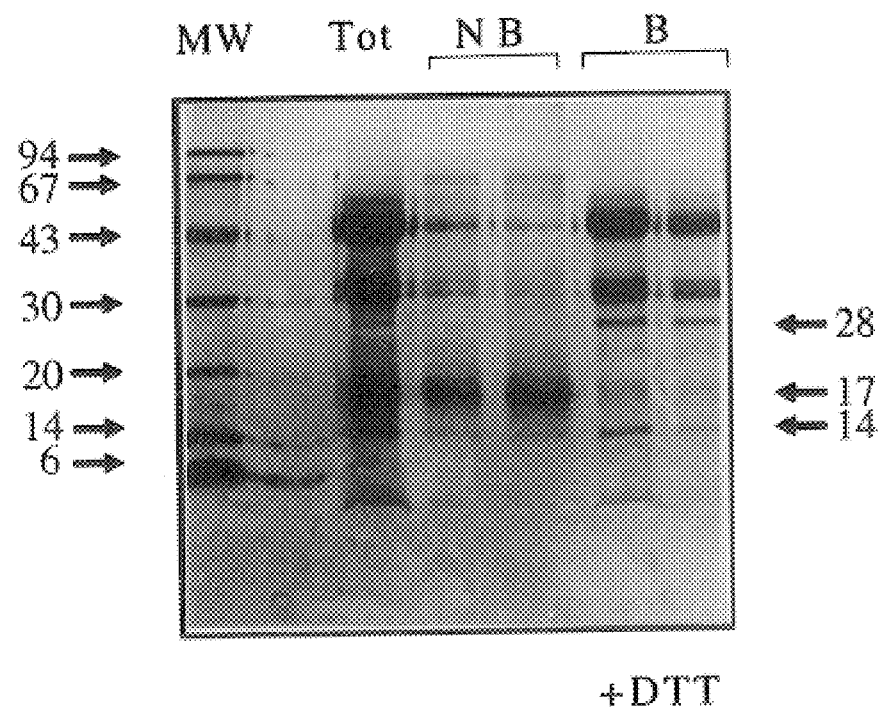

The IgG3 of the camel (*Camelus dromedarius*) purified by affinity chromatography on Protein A Sepharose were partially digested with papain and the digest was separated on Protein A Sepharose into binding and non binding fractions. These fractions were analysed by SDS PAGE under reducing and non reducing conditions (FIG. 4A and B).

The bound fraction contained two components, one of 28 Kd and one of 14.4 Kd, in addition to uncleaved or partially cleaved material. They were well separated by gel electrophoresis (from preparative 19% SDS-PAGE gels) under non reducing conditions and were further purified by electroelution (in 50 nM amonium bicarbonate, 0.1% (w/v) SDS using a BioRad electro-eluter). After lyophilization of these electroeluted fractions, the remaining SDS was eliminated by precipitating the protein by the addition of 90% ethanol, mixing and incubating the mixture overnight at −20° C. (14). The precipitated protein was collected in a pellet by centrifuging (15000 rpm, 5 min) and was used for protein sequencing. N-terminal sequencing was performed using the automated Edman chemistry of an Applied Biosystem 477A pulsed liquid protein sequencer. Amino acids were identified as their phenylthiohydantoin (PTH) derivatives using an Applied Biosystem 120 PTH analyser. All chemical and reagents were purchased from Applied Biosystems. Analysis of the chromatographic data was performed using Applied Biosystems software version 1.61. In every case the computer aided sequence analysis was cofirmed by direct inspection of the chromatograms from the PTH analyser. Samples for protein sequencing were dissolved in either 50% (v/v) trifluoroacetic acid(TFA) (28 Kd fragment) or 100% TFA (14 Kd fragment). Samples of dissolved protein equivalent to 2000 pmol (28 Kd fragment) or 500 pmol (14 Kd fragment) were applied to TFA-treated glass fibre discs. The glass fibre discs were coated with BioBrene (3 mg) and precycled once before use.

N-terminal sequencing of the 28 Kd fragment yields a sequence homologous to the N-terminal part of γ $C_H2$ domain and hence to the N-terminal end of the Fc fragment. The N-terminal sequence of the 14.4 Kd fragment corresponds to the last lysine of a γ $C_H2$ and the N-terminal end of a γ $C_H3$ domain (Table 1). The molecular weight (MW) of the papain fragments and the identification of their N-terminal sequences led us to conclude that the $C_H2$ and $C_H3$ domains of the γ3 heavy chains are normal in size and that the deletion must occur either in the $C_H1$ or in the $V_{HH}$ domain to generate the shorted γ3 chain. The fractions which do not bind to Protein A Sepharose contain two bands of 34 and 17 Kd which are more diffuse is SDS PAGE indicating that they originate from the variable N-terminal part of the molecule (FIG. 4A and B).

Upon reduction, a single diffuse band of 17 Kd is found indicating that the 34 Kd is a disulfide bonded dimer of the 17 Kd component. The 34 Kd fragment apparently contains the hinge and the N-terminal domain $V_{HH}$.

The protein sequence data can be used to construct degenerate oligonucleotide primers allowing PCR amplification of cDNA or genomic DNA.

It has been shown that the cells from camel spleen imprint cells reacted with rabbit and anti camel immunoglobulin sera and that the spleen was hence a site of synthesis of at least one immunoglobulin class. cDNA was therefore synthetised from camel spleen mRNA. The conditions for the isolation of RNA were the following: total RNA was isolated from the dromedary spleen by the guanidium isothiocyanate method (15). mRNA was purified with oligo T-paramagnetic beads.

cDNA synthesis is obtained using 1 μg mRNA template, an oligodT primer and reverse transcriptase (BOERHINGER MAN). Second strand cDNA is obtained using RNAse H and E coli DNA polymerase I according to the condition given by the supplier.

Relevant sequences were amplified by PCR: 5 ng of cDNA was amplified by PCR in a 100 μl reaction mixture (10 mM Tris-HCl pH 8.3, 50 mM KCl, 15 mM $MgCl_2$, 0.01% (w/v) gelatine, 200 μM of each dNTP and 25 pmoles of each primer) overlaid with mineral oil (Sigma).

Degenerate primers containing EcoRI and KpnI sites and further cloned into pUC 18. After a round of denaturing and annealing (94° C. for 5 min and 54° C. for 5 min), 2 units of Taq DNA polymerase were added to the reaction mixture before subjecting it to 35 cycles of amplification: 1 min at 94° C. (denature) 1 min at 54° C. (anneal), 2 min at 72° C. (elongate). To amplify DNA sequences between $V_{HH}$ and $C_H2$ domains, (#72 clones), the PCR was performed in the same conditions with the exception that the annealing temperature was increased to 60° C.

One clone examined (#56/36) had a sequence corresponding to the N-terminal part of a $C_H2$ domain identical to the sequence of the 28 Kd fragment. The availability of this sequence data allowed the construction of an exact 3' primer and the cloning of the region between the N-terminal end of the $V_{HH}$ and the $C_H2$ domain.

5' primers corresponding to the mouse $V_{HH}$ (16) and containing a XhoI restriction site were used in conjunction with the 3' primer in which a KpnI site had been inserted and the amplified sequences were cloned into pBluescript®. Clone #56/36 which displayed two internal HaeIII sites was digested with this enzyme to produce a probe to identify PCR positive clones.

After amplification the PCR products were checked on a 1.2% (w/v) agarose gel. Cleaning up of the PCR products included a phenol-chloroform extractio followed by further purification by HPLC (GEN-PAC FAX column, Waters) and finally by using the MERMAID or GENECLEAN II kit, BIO 101, Inc) as appropriate. After these purification steps, the amplified cDNA was then digested with EcoRI and KpnI for series #56 clones and with XhoI and KpnI for series #72 clones. A final phenol-chloroform extraction preceded the ligation into pUC 18 (series #56 clones) or into pBluescript® (series #72 clones).

All the clones obtained were smaller that the 860 base pairs to be expected if they possessed a corplet $V_{HH}$ and $C_H1$ region. Partial sequence data corresponding to the N-terminal of the $V_{HH}$ region reveals that out of 20 clones, 3 were identical and possibly not independent. The sequences obtained ressemble the human subgroup III and the murine subgroups IIIa and IIIb (Table 2).

Clones corresponding to two different sets of $C_H2$ protein sequences were obtained. A first set of sequences (#72/41) had a N-terminal $C_H2$ region identical to the one obtained by protein sequencing of the 28 Kd papain fragments of the γ3 heavy chain, a short hinge region containing 3 cysteines and a variable region corresponding to the framework (FR4) residues encoded by the J minigenes adjoining the hinge. The $C_H1$ domain is entirely lacking. This cDNA corresponds to the γ3 chain (Table 4).

In one closely related sequence (#72/1) the proline in position 259 is replaced by threonine.

The sequence corresponding to the $C_H3$ and the remaining part of the $C_H2$ was obtained by PCR of the cDNA using as KpnI primer a poly T in which a KpnI restriction site had been inserted at the 5' end. The total sequence of the γ3 chain corresponds to a molecular weight (MW) which is in good agreement with the data obtained from SDS PAGE electrophoresis.

The sequence of this γ3 chain presents similarities with other γ chains except that it lacks the $C_H1$ domain, the $V_{HH}$ domain being adjacent to the hinge.

One or all three of the cysteines could be probably responsible for holding the two γ3 chains together.

Figure 5:
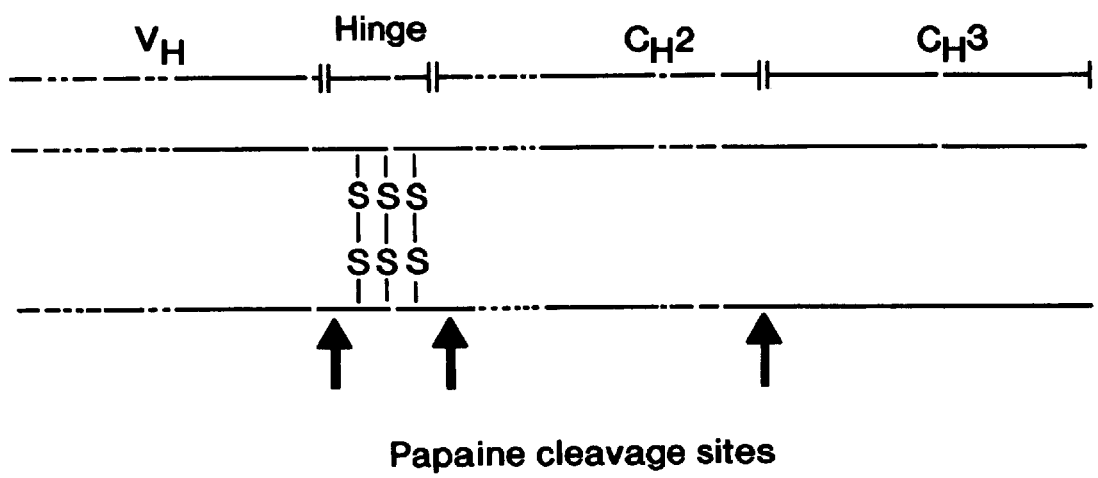

These results have allowed us to define a model for the IgG3 molecule based on sequence and papain cleavage (FIG. 5).

Papain can cleave the molecule on each side of the hinge disulfides and also between $C_H2$ and $C_H3$. Under non reducing conditions the $V_{HH}$ domains of IgG3 can be isolated as disulfide linked dimer or as monomer depending on the site of papain cleavage.

A second set of clones #72/29 had a slightly different sequence for the $C_H2$ and was characterized by a very long hinge immediately preceded by the variable domain. This hinge region has 3 cysteines at its C-terminal end in a sequence homologeous to the γ3 hinge. Such second set of clones could represent the IgG2 subclass. For the constant part of the γ3 and also for the putative γ2, most clones are identical showing the γ2 or γ3 specific sequences. A few clones such as #72/1 however show minor differences. For instance in the case of clones #72/1 two nucleotide differences are detected.

Several $V_{HH}$ regions cDNA's have now been totally or partially sequenced with the exception of a short stretch at the N-terminal end which is primer derived.

Upon translation the majority shows the characteristic heavy chain $Ser_{21}$ $CyS_{22}$ and $Tyr_{90}$ $Tyr_{91}$ $Cys_{92}$ sequences, of the intra $V_{HH}$ region disulfide bridge linking residues 22 and 92. All these clones have a sequence corresponding to the framework 4 (FR4) residues of the variable region immediately preceding the postulated hinge sequence (Table 3). This sequence is generated by the J minigenes and is in the majority of cases similar to the sequence encoded by the human and murine J minigenes. The sequence length between region $CYS_{92}$ and the C-terminal end of the $V_{HH}$ regions is variable and, in the sequences determined, range from 25 to 37 amino-acids as one might expect from the rearrangements of J and D minigenes varying in length.

Several important questions are raised by the sole existence of these heavy chain immunoglobulins in a non pathological situation. First of all, are they bonafide antibodies? The heavy chain immunoglobulins obtained from trypanosome infected camels react with a large number of parasite antigens as shown in part I of these examples. This implies that the camelid immune system generates an extensive number of binding sites composed of single $V_{HH}$ domains. This is confirmed by the diversity of the $V_{HH}$ regions of the heavy chain immunogobulins obtained by PCR.

The second question is "how are they secreted ?". The secretion of immunoglobulin heavy chains composing four-chain model immunoglobulins does not occur under normal conditions. A chaperoning protein, the heavy chain binding protein, or BIP protein, prevents heavy chains from being secreted. It is only when the light chain dispplaces the BIP protein in the endoplasmatic reticulum that secretion can occur (13).

The heavy chain dimer found in the serum of human or mice with the so-called "heavy chain disease" lack the $C_H1$ domains thought to harbour the BIP site (14). In the absence of thi domain the BIP protein can no longer bind and prevent the transport of the heavy chains.

The presence in camels of a IgG1 class composed of heavy and light chains making up between 25% and 50% of the total IgG molecules also raises the problem as to how maturation and class switching occurs and what the role of the light chain is. The camelid light chain appears unusually large and heterogeneous when examined in SDS PAGE.

Figure 6:
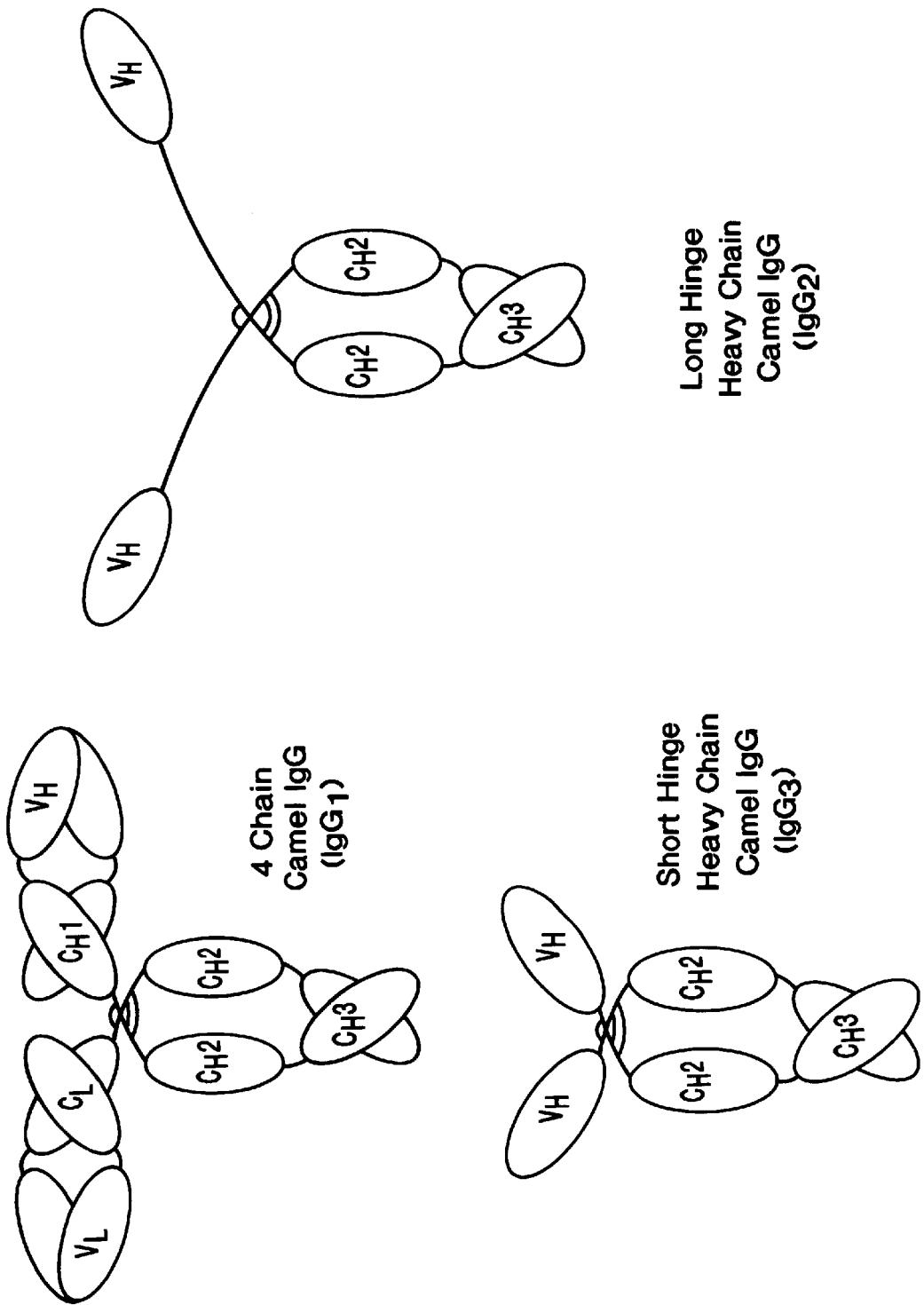

The largest dimension of an isolated domain is 40 Å and the maximum attainable span between binding sites of a conventional IgG with $C_H1$ and $V_{HH}$ will be of the order of 160 Å ($2V_{HH}+2C_H1$)(19). The deletion of $C_H1$ domain in the two types of heavy chain antibodies devoid of light chains, already sequenced has, as a result, a modification of this maximum span (FIG. 6). In the IgG3 the extreme distance between the extremities of the $V_{HH}$ regions will be of the order of 80 Å ($2V_{HH}$). This could be a severe limitation for agglutinating or cross linking. In the IgG2 this is compensated by the extremely long stretch of hinge, composed of a 12-fold repeat of the sequence Pro-X (where X is Gln, Lys or Glu) and located N-terminal to the hinge disulfide bridges. In contrast, in the human IgG3, the very long hinge which also apparently arose as the result of sequence duplication does not contribute to increase the distance spanning the two binding sites as this hinge is inter-spersed with disulfide bridges.

The single $V_{HH}$ domain could also probably allow considerably rotational freedom of the binding site versus the Fc domain.

Unlike myeloma heavy chains which result probably from $C_H1$ deletion in a single antibody producing cell, or heavy chain antibodies produced by expression cloning (15); the camelid heavy chain antibodies (devoid of light chains) have emerged in a normal immunological environment and it is expected that they will have undergone the selective refinement in specificity and affinity accompanying B cell maturation.

EXPRESSION AND PURIFICATION OF THE CAMEL $V_{HH}21$ (DR21 ON FIG. 7) PROTEIN FROM E.coli The clones can be expressed in several types of expression vectors. As an example using a commercially available vector Immuno PBS (Huse et al: Science (1989) 246, 1275), clones produced in Bluescript® according to the above described procedure, have been recovered by PCR using the same XhoI containing 5' primer and a new 3' primer, corresponding to residues 113–103 in the framework of the immunoglobulins, in which an Spe site has been constructed: TC TTA ACT AGT GAG GAG ACG GTG ACC TG SEQ ID NO:51. This procedure allowed the cloning of the $V_{HH}$ in the Xho/Spe site of the Immuno PBS vector. However, the 3' end of the gene was not in phase with the identification "tag" and the stop codon of the vector. To achieve this, the construct was cut with Spe and the 4 base overhangs were filled in, using the Klenow fragment after which the vector was religated.

The expression vector plasmid ipBS (immunopBS) (Stratacyte) contains a pel B leader sequence which is used for immunoglobulin chain expression in E.coli under the promotor pLAC control, a ribosome binding site, and stop codons. In addition, it contains a sequence for a c-terminal decapeptide tag.

E.coli JM101 harboring the ipBS-$V_{HH}21$ plasmid was grown in 1 l of TB medium with 100 µg/ml ampicillin and 0.1% glucose at 32° C. Expression was induced by the addition of 1 mM IPTG (final concentration) at an $OD_{550}$ of 1.0. After overnight induction at 28° C., the cells were harvested by centrifugation at 4.000 g for 10 min (4° C.) and resuspended in 10 ml TES buffer (0.2 M Tris-HCL pH 8.0, 0.5 mM EDTA, 0.5 M sucrose). The suspension was kept on ice for 2 hours. Periplasmic proteins were removed by osmotic shock by addition of 20 ml TES buffer diluted 1:4 v/v with water, kept on ice for one hour and subsequently centrifugated at 12.000 g for 30 min. at 4° C. The supernatant periplasmic fraction was dialysed against Tris-HCl pH 8.8, NaCl 50 mM, applied on a fast Q Sepharose flow (Pharmacia) column, washed with the above buffer prior and eluted with a linear gradient of 50 mM to 1 M NaCl in buffer.

Fractions containing the $V_{HH}$ protein were further purified on a Superdex 75 column (Pharmacia) equilibrated with PBS buffer (0.01 M phosphate pH 7.2, 0.15 M NaCl). The yield of purified $V_{HH}$ protein varies from 2 to 5 mg/l cell culture.

Fractions were analyzed by SDS-PAGE(I). Positive identification of the camel $V_{HH}$ antibody fragment was done by Western Blot analysis using antibody raised in rabbits against purified camel $IgGH_3$ and an anti-rabbit IgG-alkaline phosphatase conjugate (II).

Figures 8A, 8B:
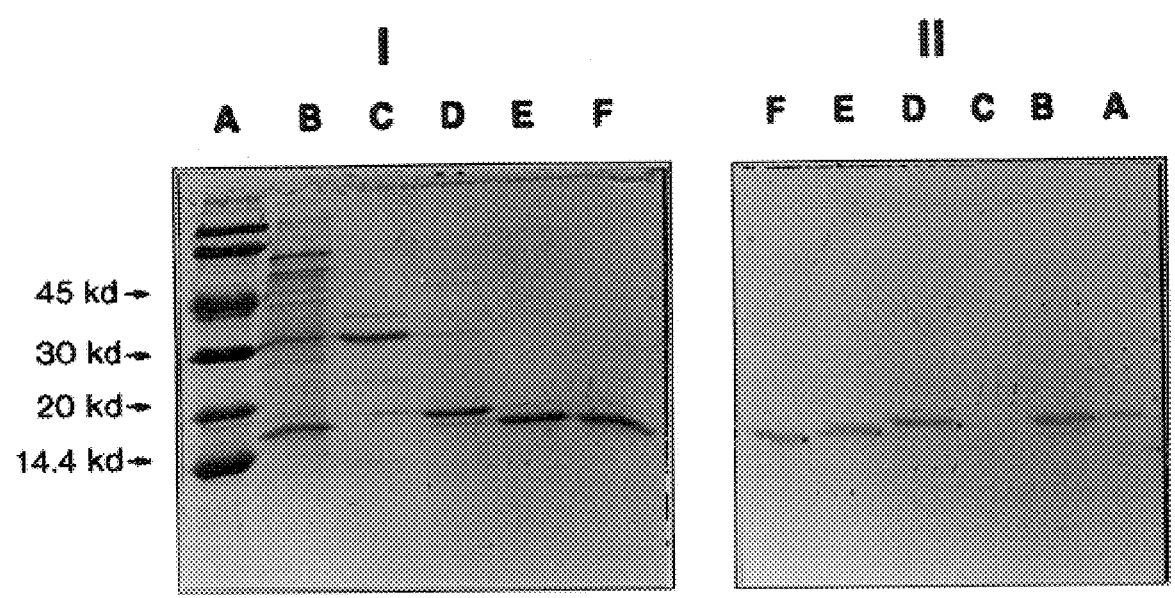

As protein standards (Pharmacia) periplasmic proteins prepared from 1 ml of IPTG-induced JM101/ipBS $V_{HH}21$ were used. FIG. 8 shows: C,D:fractions from fast S Sepharose column chromatography (C:Eluted at 650 mM NaCl D:Eluted at 700 mM NaCl) E,F:fractions from Superdex 75 column chromatography.

As can be seen, the major impurity is eliminated by ionexchange chromatography and the bulk of the remaining impurities are eliminated by gel filtration.

TABLE 1

Comparison of the N terminal Camel C_H2 and C_H3 sequences with the translated cDNA sequences of Camel immunoglobulins and with the corresponding human γ sequences. (Numbering according to Kabat et al (1987)(7).

```
                            250             260             270
Camel     γ3 28Kd   - L P G G P S V F V F P P K P K D V L S I X G X P - -    SEQ ID NO:54

Clone     # 72/1    - L P G G P S V F V F P T K P K D V L S I S G R P - -    SEQ ID NO:55

Clone     # 72/4    - L P G G P S V F V F P P K P K D V L S I S G R P - -    SEQ ID NO:56

Clone     # 72/29   - L L G G P S V F I F P P K P K D V L S I S G R P - -    SEQ ID NO:57

Human     γ1γ3      - L L G G P S V F L P P K P K D T L M I S R T P - -      SEQ ID NO:112

C_H2      γ2        - V A - G P S V F L P P K P K D T L M I S R T P - -
                    SEQ ID NO:113

γ4        - F L G G P S V F L P P K P K D T L M I S R T P - -      SEQ ID NO:114

C_H2|C_H3
                      360                 370
Camel     γ3 14Kd   - K|G Q T R E P Q V Y T L A P X R L E L - -               SEQ ID NO:54

Human     γ1        - K|G Q P R E P Q V Y T L P P S R D E L - -               SEQ ID NO:115

C_H2/C_H3 γ2,γ3     - K|G Q P R E P Q V Y T L P P S R E E M - -               SEQ ID NO:116

γ4        - K|G Q P R E P Q V Y T L P P S Q E E M - -               SEQ ID NO:117
```

TABLE 2

A comparison of N Terminal Fr 1 regions of Camel V_HH with a Human V_HIII subgroup protein and a mouse V_HIIIA subgroup protein.

```
                        10              20              30
Primer Derived      G G S V Q T G G S L R L S C E I S G L T F D  # 72/4            SEQ ID NO:1

G G S V Q T G G S L R L S C A V S G F S F S  # 72/3            SEQ ID NO:2

G G S E Q G G G S L R L S C A I S G Y T Y G  # 72/7            SEQ ID NO:3

G G S V Q P G G S L T L S C T V S G A T Y S  # 72/17           SEQ ID NO:4

G G S V Q A G G S L R L S C T G S G F P Y S  # 72/18           SEQ ID NO:5

D V Q L V A S       G G G S V G A G G S L R L S C T A S G D S F S  # 72/2         SEQ ID NO:58

E V K L V E S       G G G L V E P G G S L R L S C A T S G F T F S  Mouse V_IIIII_A SEQ ID NO:118

E V Q L L S       G G G L V Q P G G S L R L S C A A S G F T F S  Human V_HIII   SEQ ID NO:119
```

The invariable subgroup specific residues are grayed.

TABLE 3

Comparison of some Framework 4 residues found in the Camel V_H region with the Framework 4 residues corresponding to the consensus region of the Human and Mouse J minigenes.

| FrameWork 4 | | J Genes |
|---|---|---|
| Human | W G Q G T L V T V S S  SEQ ID NO:9 | J1, J4, J5 |
|  | W G R G T L V T V S S  SEQ ID NO:130 | J2 |

TABLE 3-continued

Comparison of some Framework 4 residues found in the Camel V$_H$ region with the Framework 4 residues corresponding to the consensus region of the Human and Mouse J minigenes.

FrameWork 4

|  |  |  |
|---|---|---|
|  | W G Q G T T V T V S S SEQ ID NO:120 | J6 |
|  | W G Q G T M V T V S S SEQ ID NO:121 | J3 |
| Murine | W G Q G T T L T V S S SEQ ID NO:122 | J1 |
|  | W G Q G T L V T V S S SEQ ID NO:19 | J2 |
|  | W G Q G T S V T V S A SEQ ID NO:123 | J3 |
|  | W G A G T T V T V S S SEQ ID NO:124 | J4 |

|  |  | cDNA Clones |
|---|---|---|
| Camel | W G Q G T Q V T V S S SEQ ID NO:8 | Clones |
|  | W G Q G T Q V T V S S SEQ ID NO:8 | #72/19 = #72/3 |
|  | W G Q G T L V T V S S SEQ ID NO:9 | 1 Clone |
|  | W G R G T Q V T V S S SEQ ID NO:59 | #72/24 |
|  | W G Q G T H V T V S S SEQ ID NO:60 | #72/21 |
|  | W G Q G I Q V T A S S SEQ ID NO:61 | #72/16 |

```
             d y y g s s - - - - - - - y - - f - - - - - d v W G A G T T V T V S S   SEQ ID NO:125  18 different-
                                                                                                    camel
         95       100 a b c d e f g h i j k - - - - 101     105      110                           camel
                                                                                                    VH region 1   a l q p g g y c g y g x - - - - - - - - - - - c l W G Q G T Q V T V S S   SEQ ID NO:13
 2   v s l m d r i s q h - - - - - - - - - - - - - g c R G Q G T Q V T V S L   SEQ ID NO:14
 3   v p e h l g p g a i l d l k k y - - - - - - k y W G Q G T Q V T V S S     SEQ ID NO:15
 4   f c y s t a g d g g s g e - - - - - - - - - m y W G Q G T Q V T V S S     SEQ ID NO:16
 7   e l s g g s c e l p l l f - - - - - - - - - d y W G Q G T Q V T V S S     SEQ ID NO:17
 9   d w k y w t c g a q t g g y f - - - - - - - g q W G Q G A Q V T V S S     SEQ ID NO:18
11   r l t e m g a c d a r w a t l a t r t f a y n y W G Q G T Q V T V S S     SEQ ID NO:19
13   q k k d r t r w a e p r e w - - - - - - - - n n W G Q G T Q V T A S S     SEQ ID NO:20
16   g s r f s s p v g s t s r l e s - s d y - - n y W G Q G I Q V T A S S     SEQ ID NO:21
17   a d p s i y y s i l x i e y - - - - - - - - k y W G Q G T Q V T V S S     SEQ ID NO:22
18   d s p c y m p t m p a p p i r d s f g w - - d d F G Q G T Q V T V S S     SEQ ID NO:23
19   t s s t y w y c t t a p y - - - - - - - - - n v W G Q G T Q V T V S S     SEQ ID NO:24
20   t e i e w y g c n l r t t f - - - - - - - - t r W G Q G T Q V T V S S     SEQ ID NO:25
21   n q l a g g w y l d p n y w l s v g a y - - a i W G Q G T H V T V S S     SEQ ID NO:26
24   r l t e m g a c d a r w a t l a t r t f a y n y W G R G T Q V T V S S     SEQ ID NO:27
25   d g w t r k e g g i g l p w s v q c e d g y n y W G Q G T Q V T V S S     SEQ ID NO:28
27   d s y p c h l l - - - - - - - - - - - - - - d v W G Q G T Q V T V S S     SEQ ID NO:29
29   v e y p i a d m c a - - - - - - - - - - - - r y G D P G T Q V T V S S     SEQ ID NO:30
```

TABLE 5

```
          10          20                       40
EVQLVESGGG LVQPGGGSLRL SCAASG SEQ ID NO:80 CDR1 WVRQA PGKGLEWVS SEQ ID NO:81 CDR2

GG SVQGGGSLRL SCAISG SEQ ID NO:84 CDR1 WFREG PGKEREGIA SEQ ID NO:85 CDR2

GG SVQAGGSLRL SCASSS SEQ ID NO:88 CDR1 WYRQA PGKEREFVS SEQ ID NO:89 CDR2

70         80          90                     110
RFTIS RDNSKNTLYL QMNSLRAEDTAVY YCAR SEQ ID NO:82 CDR3 WGQGTLVT VSS SEQ ID NO:83

RFTIS QDSTLKTMYL LMNNLKPEDTGTY YCAA SEQ ID NO:86 CDR3 WGQGTQVT VSS SEQ ID NO:91

RFTIS QDSAKNTVYL QMNSLKPEDTAMY YCKI SEQ ID NO:90 CDR3 WGQGTQVT VSS SEQ ID NO:87
```

|  | camel V$_H$ | hinge | C$_H$2 |
|---|---|---|---|
| camel | WGQGTQVT VSS | ———GTNEVCKCPKCP | APELPGG PSVFVFP SEQ ID NO:91 |
|  | WGQGTQVT VSS | — EPKIPQPQPKPQPQP | |
|  |  | QPQPKPQP | |
|  |  | KPEPECTCPKCP | APELLGG PSCFIFP SEQ ID NO:87 |
|  | human C$_H$1 | hinge | C$_H$2 |
| human gamma 3 | KVDKRV | ELKTPLGDTTHTCPRCP | |
|  |  | EPKCSDTPPPCPRCP | |
|  |  | EPKSCDTPPPCPRCP | APELLGG PSVFLFP SEQ ID NO:126 |
| human gamma 1 | KVDKK | —AEPKSCDKTHTCPPCP | APELLGG PSVFLFP SEQ ID NO:127 |
| human gamma 2 | KVKVTV | ———ERKCCVECPPCP | APPVAG- PSVFLFP SEQ ID NO:128 |
| human gamma 3 | KVDKRV | ———ESKYGPPCPSCP | APEFLGG PSVFLFP SEQ ID NO:129 |

REFERENCES

1. Ward, E. S., Gussow, D., Griffits, A. D., Jones, P. T. and Winter G. Nature 341, 544–546 (1989).
2. Ungar-Waron H., Eliase E., Gluckman A. and Trainin Z. Isr. J. Vet. Med., 43, 198–203 (1987).
3. Bajyana Songa E. and Hamers R., Ann. Soc. Belge Med. trop., 68, 233–240 (1988).
4. Edelman G. M., Olins D. E., Gally J. A. and Zinder N. D., Proc. Nat. Acad. Sc., 50, 753 (1963).
5. Franek F. and Nezlin R. S., Biokhimiya, 28, 193 (1963).
6. Roitt I. M., Brostof J. and Male D. K., Immunology, Gower Med. Pub. London. New-York, p.9.2. (1985).
7. Schiffer M., Girling R. L., Ely K. R. and Edmundson B., Biochemistry, 12, 4620–4631 (1973).
8. Fleischman J. B., Pain R. H. and Porter R. R., Arch. Biochem. Biophys, Suppl. 1, 174 (1962).
9. Roholt O., Onoue K. and Pressman D., PNAS 51, 173–178 (1964).
10. Seligmann M., Mihaesco E., Preud'homme J. L., Danon F. and Brouet J. C., Immunological Rev., 48, 145–167 (1979).
11. Henderschot L., Bole D., Kohler G. and Kearney J. F., The Journal of Cell Biology, 104, 761–767 (1987).
12. Henderschot L. M., The Journal of Cell Biology, 111, 829–837 (1990).
13. Hamers-Casterman, C., E. Wittouck, W. Van der Loo and R. Hamers, Journal of Immunogenetics, 6, 373–381 (1979).
14. Applied Biosystems—Ethanol Precipitation of Electro Eluted Electrodialysed Sample. Issue n* 27.
15. Maniatis, T. E. F. Fritsch and J. Sambrook, Molecular Cloning. A Laboratory Manual (1988).
16. Sastry et al., PNAS, 86, 5728, (1989).
17. Sanger, F., S. Nicklen and A. R. Coulson, Proc. Natl. Acad. Sci., U.S.A., 74, 5463–5467 (1977).
18. Kabat E. A., Tai Te Wu, M. Reid-Miller, H. M. Perry and K. S. Gottesman, U.S. Dpt of Health and Human Services, Public Health Service, National Institutes of Health (1987).
19. Valentine, R. C. and N. M. Geen, J. M. B., 27, 615–617 (1967).

We claim:

1. An immunoglobulin comprising two heavy polypeptide chains, each heavy chain consisting of a complete antigen binding site, said immunoglobulin containing a variable ($V_{HH}$) region and a constant region, said constant region being devoid of first constant domain $C_H1$, wherein the immunoglobulin is devoid of polypeptide light chains, wherein said immunoglobulin is obtainable by a process comprising the steps of:

obtaining a first DNA or cDNA sequence coding for a $V_{HH}$ domain or part thereof having a determined specificity against a given antigen and comprised between Xho and Spe sites, obtaining a second DNA or cDNA sequence coding for a $V_{HH}$ domain or part thereof, having a determined specificity different from the specificity of the first DNA or cDNA sequence and comprised between the Spe and EcoRI sites;

digesting an immuno PBS vector with EcoRI and XhoI restriction enzymes, ligating the obtained DNA or cDNA sequence coding for $V_{HH}$ domains so that the DNA or cDNA sequences are serially cloned in the vector;

transforming a host cell by transfection; and recovering the immunoglobulins.

2. The immunoglobulin of claim 1, wherein said host cell is an *E. coli* cell.

3. A $V_{HH}$ sequence of an immunoglobulin comprising two heavy polypeptide chains, each heavy chain consisting of a complete antigen binding site, said immunoglobulin containing a variable ($V_{HH}$) region and a constant region, said constant region being devoid of first constant domain $C_H1$, wherein the immunoglobulin is devoid of light chains, wherein said $V_{HH}$ sequence is obtained by a process comprising the steps of:

obtaining a DNA or cDNA sequence coding for a $V_{HH}$ domain or part thereof having a determined specificity against a given antigen and comprised in the framework sequences containing XhoI and SpeI restriction sites;

ligating the obtained DNA or cDNA sequences in a vector so that the DNA or cDNA is serially cloned in the vector;

transforming a host cell with the ligated vector, and recovering immunoglobulins containing said $V_{HH}$ sequence.

4. A $V_{HH}$ sequence of an immunoglobulin comprising two heavy polypeptide chains, each heavy chain consisting of a complete antigen binding site, said immunoglobulin containing a variable ($V_{HH}$) region and a constant region, said constant region being devoid of first constant domain $C_H1$, wherein the immunoglobulin is devoid of light chains, wherein said $V_{HH}$ sequence is obtained by a process comprising the steps of:

obtaining a DNA or cDNA sequence coding for a $V_{HH}$ domain or part thereof having a determined specificity against a given antigen and comprised in the framework sequences containing XhoI and SpeI restriction sites;

obtaining a second DNA or cDNA sequence coding for a $V_{HH}$ domain or part thereof having a determined specificity against a given antigen different from the specificity of the first DNA or cDNA sequence and comprised in the framework sequences containing XhoI and EcoRI restriction sites;

ligating the obtained DNA or cDNA sequences coding for the $V_{HH}$ sequences in a vector so that the DNA or cDNA sequences are serially cloned in the vector;

transforming a host cell with the ligated vector; and recovering immunoglobulins containing said $V_{HH}$ sequence.

5. An immunoglobulin comprising two heavy polypeptide chains, each heavy chain consisting of a complete antigen binding site, said immunoglobulin containing a variable ($V_{HH}$) region and a constant region, said constant region being devoid of first constant domain $C_H1$, wherein the immunoglobulin is devoid of light chains, wherein said immunoglobulin is obtained by a process comprising the steps of:

obtaining a first DNA or cDNA sequence coding for an immunoglobulin domain or part thereof having a determined specificity against a given antigen and comprised between the 5' primer located in the promoter, leader or framework sequences of the $V_{HH}$, and a 3' primer located in the hinge, $C_H2$ or $C_H3$ sequence of the $V_{HH}$ sequence;

obtaining a second DNA or cDNA sequence coding for a $V_{HH}$ domain or part therof having a determined specificity different from the specificity of the first DNA or cDNA sequence;

ligating the obtained DNA or cDNA sequences coding for the $V_{HH}$ sequences in a vector so that the DNA or cDNA sequences are serially cloned in the vector;

transforming a host cell with the ligated vector; and recovering said immunoglobulin.

6. A $V_{HH}$ sequence of an immunoglobulin comprising two heavy polypeptide chains each heavy chain consisting of a complete antigen binding site, said immunoglobulin containing a variable ($V_{HH}$) region and a constant region, said constant region being devoid of first constant domain $C_H1$, wherein the immunoglobulin is devoid of light chains, wherein said $V_{HH}$ sequence is obtained by a process comprising the steps of:

obtaining a DNA or cDNA sequence coding for a $V_{HH}$ domain or part thereof having a determined specificity against a given antigen and comprised between a 5' primer located in the promoter, leader or framework sequences of the $V_{HH}$, and a 3' primer located in the hinge, $C_H2$ or $C_H3$ sequence of the $V_{HH}$;

ligating the obtained DNA or cDNA sequences in a vector so that the DNA or cDNA sequences are serially cloned in the vector;

transforming a host cell with the ligated vector; and recovering immunoglobulins containing said $V_{HH}$ sequence.

7. A $V_{HH}$ sequence of an immunoglobulin comprising two heavy polypeptide chains each heavy chain consisting of a complete antigen binding site, said immunoglobulin containing a variable ($V_{HH}$) region and a constant region, said constant region being devoid of first constant domain $C_H1$, wherein the immunoglobulin is devoid of light chains, wherein said $V_{HH}$ sequence is obtained by a process comprising the steps of:

obtaining a first DNA or cDNA sequence coding for a $V_{HH}$ domain or part thereof having a determined specificity against a given antigen and comprised between a 5' primer located in the promoter, leader or framework sequences of the $V_{HH}$, and a 3' primer located in the hinge, $C_H2$ or $C_H3$ sequence of the $V_{HH}$;

obtaining a second DNA or cDNA sequence coding for a $V_{HH}$ domain or part thereof having a determined specificity against a given antigen different from the specificity of the first DNA or cDNA sequence and comprised between a 5' primer located in the promoter, leader or framework sequences of the $V_{HH}$, and a 3' primer located in the hinge, $C_H2$ or $C_H3$ sequence of the $V_{HH}$;

ligating the obtained DNA or cDNA sequences coding for the $V_{HH}$ sequences in a vector so that the DNA or cDNA sequences are serially cloned in the vector;

transforming a host cell with the ligated vector; and recovering immunoglobulins containing said $V_{HH}$ sequence.

8. An immunoglobulin according to claim 1 or claim 5, wherein the host cell is a eukaryotic cell.

9. A $V_{HH}$ sequence according to any one of claims 3–4 or 6–7, wherein the host cell is a eukaryotic cell.

10. An immunoglobulin according to claim 8, wherein the eukaryotic cell is selected from the group consisting of insect cells and mammalian cells.

11. An immunoglobulin according to claim 10, wherein the mammalian cells are selected from the group consisting of CHO cells and Simian cells.

12. A $V_{HH}$ sequence according to claim 9, wherein the eukaryotic cell is selected from the group consisting of insect cells and mammalian cells.

13. A $V_{HH}$ sequence according to claim 12, wherein the mammalian cells are selected from the group consisting of CHO cells and Simian cells.

* * * * *